US006514719B1

(12) United States Patent
Bird et al.

(10) Patent No.: US 6,514,719 B1
(45) Date of Patent: Feb. 4, 2003

(54) METHODS FOR IDENTIFYING COMPOUNDS THAT ALTER KINASE ACTIVITY

(75) Inventors: Timothy A. Bird, Bainbridge Island, WA (US); G. Duke Virca, Bellevue, WA (US); Unja Martin, Seattle, WA (US); Dirk M. Anderson, Seattle, WA (US)

(73) Assignee: Immunex Corporation, Seattle, WA (US)

( * ) Notice: Subject to any disclaimer, the term of this patent is extended or adjusted under 35 U.S.C. 154(b) by 0 days.

(21) Appl. No.: 09/579,664

(22) Filed: May 26, 2000

Related U.S. Application Data

(60) Provisional application No. 60/136,781, filed on May 28, 1999.

(51) Int. Cl.[7] .............................. C12Q 1/48; C12N 9/12; C12N 15/74; C12P 21/06; C07H 21/04
(52) U.S. Cl. ........................ 435/15; 435/194; 435/325; 435/252.3; 435/320.1; 435/69.1; 536/23.2
(58) Field of Search .......................... 435/15, 194, 325, 435/252.3, 320.1, 69.1; 536/23.2

(56) References Cited

FOREIGN PATENT DOCUMENTS

| WO | WO0006728 A3 | 2/2000 |
|---|---|---|
| WO | WO0006728 A2 | 2/2000 |
| WO | WO0129063 A2 | 4/2001 |
| WO | WO0138503 A2 | 5/2001 |
| WO | WO0142435 A2 | 6/2001 |
| WO | WO0153312 A1 | 7/2001 |
| WO | WO0153455 A2 | 7/2002 |

OTHER PUBLICATIONS

Cho et al., Swiss Prot accession No. Q63450, 1998.*
Cho et al., GenEMBL accession No. L26288, 1995.*
Dan, I. et al. (References 1 and 2), GenBank Accession No. AB035697, Apr. 2000.
Dan, I. et al. (Reference 1) and Watanabe, N.M. et al. (Reference 2) GenBank Accession No. AB041925, Apr. 2000.
Su, Y–C. et al., "NIK is a New Ste20–Related Kinase that Binds NCK and MEKK1 and Activates the SAPK/JNK Cascade via a Conserved Regulatory Domain," *Embo J.* 16(6):1279–1290, 1997.
Yao, Z. et al. "A Novel Human STE20–Related Protein Kinase, HGK, that Specifically Activates the c–Jun N–Terminal Kinase Signaling Pathway," *Bio Chem* 274(4):2118–2125, Jan. 22, 1999.
Saito, T. et al. (References 1 and 2), GenBank Accession No. AB026289, Oct. 1999.
National Cancer Institute, Cancer Genome Anatomy Project (CGAP), GenBank Accession No. AI469033, Mar. 1999.
Picciotto M.R. et al., "Calcium/Calmodulin–Dependent Protein Kinase I," *J Biol Chem* 268(35):26512–26521, Dec. 1993.
Hillier L, et al., GenBank Accession No. AA018361, Jul. 1996.
Ohara, O. et al.(Reference 1), and Nagase, T., et al., (Reference 2), GenBank Accession No. AB011123, Apr. 1998.
Fu, C.A. et al. "TNIK, a Novel Member of the Germinal Center Kinase Family that Activates the c–Jun N–Terminal Kinase Pathway and Regulates the Cytoskeleton," *J Biol Chem* 274(43):30729–30737, Oct. 1999.
Verploegen S. et al. (reference 1), and Verploegen S. and Coffer P.J. (reference 2), GenBank Accession No. AF286366, Aug. 2000.
Verploegen S. et al. "Identification and Characterization of CKLiK, a Novel Granulocyte Ca++/ Calmodulin–Dependent Kinase," *Blood* 96(9):215–3223, Nov. 2000.

* cited by examiner

*Primary Examiner*—Rebecca E. Prouty
*Assistant Examiner*—Delia Ramirez
(74) *Attorney, Agent, or Firm*—Suzanne A. Sprunger

(57) ABSTRACT

The invention is directed to purified and isolated novel murine and human kinase polypeptides, the nucleic acids encoding such polypeptides, processes for production of recombinant forms of such polypeptides, antibodies generated against these polypeptides, fragmented peptides derived from these polypeptides, and the uses of the above.

22 Claims, 6 Drawing Sheets

```
MGDPAPARSLDDIDLSALRDPAGIFELVEVVGNGTYGQVYKGRHVKTGQLAAIKVMDVTE
                        |     || |  | |           |||| |
                        o     og G  g v           oaoK o DEEEEIKQEINMLKKYSHHRNIATYYGAFIKKSPPGNDDQLWLVMEFCGAGSVTDLVKNT
        |  ||     |  || |   |           ||||||||       |
        E  oo     h  oo o   o           ooooo*oo       o KGNALKEDCIAYICREILRGLAHLHAHKVIHRDIKGQNVLLTENAEVKLVDFGVSAQLDR
    |      |   ||  ||||     |||||||  ||||     |||||||||
    o      o   *o  +ooh     oohrDok  Nooo     oko+Dfgo+

TVGRRNTFIGTPYWMAPEVIACDENPDATYDYRSDIWSLGITAIEMAEGAPPLCDMHPMR
         ||  | |||||         |    |||||||||| |     ||
         g+  o +pEoo         o    Doo+ogoooo o     po ALFLIPRNPPPRLKSKKWSKKFTDFIDTCLIKTYLSRPAGRLVPRSPGLQEFDIKLIDTV
 || |       |           ||   ||     | |                |
 oo o       o           oo   oo     R +                o

DLEGGPGTQFAL
```

FIGURE 1

```
MDEQSQGMQGPPVTQFQPQKALRPDMGYNTLANFRIEKKIGRGQFSEVYRASCLLDGV
                                |     ||| |      |
                                o     og G    g  v

PVALKKVQIFDLMDAKARADCIKEIDLLKQLNHPNVIKYYASFIEDNELNIVLELADAGD
|||| |                  |  ||    |  || |    |       ||||||||
oaoK o                  E  oo    h  oo o    o       ooooo*oo LSRMIKHFKKQKRLIPERTVWKYFVQLCSALDHMHSRRVMHRDIKPANVFITATGVVKLG
    |          |      |  ||  ||||    |||||||  ||||         ||||
    o          o      o  *o  +ooh    oohrDok  Nooo         oko+

DLGLGRFFSSKTTAAHSLVGTPYYMSPERIHENGYNFKSDIWSLGCLLYEMAALQSPFYG
|||||             ||   |  |||||      |    ||||||||||| |      ||
Dfgo+             g+   o  +pEoo      o    Doo+ogoooo o       po DKMNLYSLCKKIEQCDYPPLPSDHYSEELRQLVNICINPDPEKRPDIAYVYDVAKRMHAC
 || |         |             ||       ||       ||       |             |
 oo o         o             oo       oo       R +                     o

TAST
```

FIGURE 2

```
MARENGESSSSWKKQAEDIKKIFEFKETLGTGAFSEVVLAEEKATGKLFA
          |            || | | |                ||
          o           og G og v                oa

VKCIPKKALKGKESSIENEIAVLRKIKHENIVALEDIYESPNHLYLVMQL
|| |              | |    | ||  |         |
oK o              E o    h oo  o         o

VSGGELFDRIVEKGFYTEKDASTLIRQVLDAVYYLHRMGIVHRDLKPENL
    |         |  ||  || |||  ||||||||  ||
    o         o  *o  +o ooh   oohrDoK+  No LYYSQDEESKIMISDFGLSKMEGKGDVMSTACGTPGYVAPEVLAQKPYSK
||      | ||||||||              ||  | |||||       |
oo      oko+Dfgo+              g+   o +pEoo       o AVDCWSIGVIAYILLCGYPPFYDENDSKLFEQILKAEYEFDSPYWDDISD
|  ||||||||  |      ||       ||  |                |
Doo+ogoooo   o      po       oo  o                o SAKDFIRNLMEKDPNKRYTCEQAARHPWIAGDTALSKNIHESVSAQIRKN
||  |         ||        |
oo  oo        R +       o

FAKSKWRQAFNATAVVRHMRRLQLGSSLDSSNASVSSNLSLASQKDCASG

TFHAL
```

FIGURE 3

```
MESVALLQRPSQAPSASALASESARPLADGLIKSPKPLMKKQAVKRHHHKHNLRHRYEFL
                                                         |
                                                         o

ETLGKGTYGKVKKARESSGRLVAIKSIRKDKIKDEQDLLHIRREIEIMSSLNHPHIIAIH
|| | || |          |||| |                  | |       |  ||
 og G og v          oaoK o                   E  oo     h  oo EVFENSSKIVIVMEYASRGDLYDYISERPRLSERDARHFFRQIVSALHYCHQNGIVHRDL
   ||||  |||        |        |         |   ||  | |   |||||
 o    00000*oo       o        o         o  *o  +o  ooh   oohrDo KLENILLDANGNIKIADFGLSNLYHKGKFLQTFCGSPLYASPEIVNGKPYVGPEVDSWSL
|  ||||     ||||||||              ||  | |||||        |  |||
K+ Nooo     oko+Dfg+               g+   o  +pEoo       o   doo+o GVLLYILVHGTMPFDGQDHKTLVKQISNGAYREPPKPSDACGLIRWLLMVNPTRRATLED
|||||  |    ||        ||   |               ||  ||        | |
Goooo o      po        oo   o                oo  oo        R +

VASHWWVNWGYTTGVGEQEALREGGHPSGDFGRASMADWLRRSSRPLLENGAKVCSFFKQ
    |
    o

HVPGGGSTVPGLERQHSLKKSRKENDMAQNLQGDPAEDTSRPGKSSLKLPKGILKKKSS

TSSGEVQEDPQELRPVPDTPGQPVPAVSLLPRKGILKKSRQRESGYYSSPEPSESGELLD

ASDVFVSGDPVEQKSPQASGLLLHRKGILKLNGKFSRTALEGTTPSTFGSLDQLASSHPA

ARPSRPSGAVSEDSILSSESFDQLDLPERLPETPLRGCVSVDNLRGLEQPPSEGLKRWWQ

ESLGDSCFSLTDCQEVTAAYRQALGICSKLS
```

FIGURE 4

```
MAGPSWGLPRLDGFILTERLGSGTYATVYKAYAKKDTREVVAIKCVAKKSLNKASVENLLT
    |            | | |           |                  | | | |  |
    o           og G  g v                           oaoK o EIEIELKGIRHPHIVQLKDFQWDNDNIYLIMEFCAGGDLSRFIHTRRILPEKVARVFMQQLA
| ||       |  | | |  |         ||||||||        |     |      | ||
E  oo      h  oo o   o         ooooo*oo        o  o  o      o *o SALQFLHERNISHLDLKPQNILLSSLEKPHLKLADFGFAQHMSPWDEKHVLRGSPLYMAPE
|| |||     | ||||||  ||||         |||||||||              || |  |||
+o ooh     oohrDok+  Nooo         oko+Dfgo+              g+ o +pE MVCRRQYDARVDLWSVGVILYEALFGQPPFASRSFSELEEKIRSNRVIEVRLAGSRHPPGI
||    |    |||||||||| |         ||        |    |      |          |
oo    o    Doo+ogoooo-o         po        oo   o      o          oo EGLKAQKFVQHCSAGSGRFMAVGHVLWWKPRVWSVPEDPYQPRQATNDQAQSSHSPGLEAN
|              | |        |
oo             R +        o

THLIGD
```

FIGURE 5

MASDSPARSLDEIDLSALRDPAGIFELVELVGNGTYGQVYKGRHVKTGQLAAIKVMDVTG
             |       || |    ||               ||||  |
             o      og G    g v              oaoK  o DEEEEIKQEINMLKKYSHHRNIATYYGAFIKKNPPGMDDQLWLVMEFCGAGSVTDLIKNT
 |  ||     |  ||| |         |          ||||||||        |
 E  oo     h  oo o         o          ooooo*oo        o  o KGNTLKEEWIAYICREILRGLSHLHQHKVIHRDIKGQNVLLTENAEVKLVDFGVSAQLDR
 |         |   ||   ||   ||   |||||||| ||||      |||||||||
 o         o  *o   +o  ooh   oohrDok+ Nooo     oko+Dfgo+

TVGRRNTFIGTPYWMAPEVIACDENPDATYDFKSDLWSLGITAIEMAEGAPPLCDMHPMR
 ||     |  ||||||           |     ||||||||||| |          ||
 g+    o  +pEoo            o     Doo+ogoooo o         po ALFLIPRNPAPRLKSKKWSKKFQSFIESCLVKNHSQRPATEQLMKHPFIRDQPNERQVRI
|| |               |        ||    ||                     | |
oo  o              o        oo    oo                     R +

QLKDHIDRTKKKRGEKDETEYEYSGSEEEEEENDSGEPSSILNLPGESTLRRDFLRLQLA
     |
     o

NKERSEALRRQQLEQQQRENEEHKRQLLAERQKRIEEQKEQRRRLEEQQRREKELRKQQE
REQRRHYEEQMRREEERRRAEHEQEYIRRQLEEEQRQLEILQQQLLHEQALLLEYKRKQL
EEQRQAERLQRQLKQERDYLVSLQHQRQEQRPVEKKPLYHYKEGMSPSEKPAWAKEVEER
SRLNRQSSPAMPHKVANRISDPNLPPRSESFSISGVQPARTPPMLRPVDPQIPHLVAVKS
QGPALTASQSVHEQPTKGLSGFQEALNVTSHRVEMPRQNSDPTSENPPLPTRIEKFDRSS
WLRQEEDIPPKVPQRTTSISPALARKNSPGNGSALGPRLGSQPIRASNPDLRRTEPILES
PLQRTSSGSSSSSSTPSSQPSSQGGSQPGSQAGSSERTRVRANSKSEGSPVLPHEPAKVK
PEESRDITRPSRPASYKKAIDEDLTALAKELRELRIEETNRPMKKVTDYSSSSEESESSE
EEEEDGESETHDGTVAVSDIPRLIPTGAPGSNEQYNVGMVGTHGLETSHADSFSGSISRE
GTLMIRETSGEKKRSGHSDSNGFAGHINLPDLVQQSHSPAGTPTEGLGRVSTHSQEMDSG
TEYGMGSSTKASFTPFVDPRVYQTSPTDEDEEDEESSAAALFTSELLRQEQAKLNEARKI
SVVNVNPTNIRPHSDTPEIRKYKKRFNSEILCAALWGVNLLVGTENGLMLLDRSGQGKVY
NLINRRRFQQMDVLEGLNVLVTISGKKNKLRVYYLSWLRNRILHNDPEVEKKQGWITVGD
LEGCIHYKVVKYERIKFLVIALKNAVEIYAWAPKPYHKFMAFKSFADLQHKPLLVDLTVE
EGQRLKVIFGSHTGFHVIDVDSGNSYDIYIPSHIQGNITPHAIVILPKTDGMEMLVCYED
EGVYVNTYGRITKDVVLQWGEMPTSVAYIHSNQIMGWGEKAIEIRSVETGHLDGVFMHKR
AQRLKFLCERNDKVFFASVRSGGSSQVFFMTLNRNSMMNW

FIGURE 6

SEQUENCE LISTING

```
<160> NUMBER OF SEQ ID NOS: 36

<210> SEQ ID NO 1
<211> LENGTH: 896
<212> TYPE: DNA
<213> ORGANISM: Mus musculus

<400> SEQUENCE: 1
ttggaacgag acgacctgct cggcggcagc ggagtgagcg agccggagcg tgagtggccc      60
cgcggcggcc atgggcgacc cagcccccgc ccgcagcctg gacgacatcg acctgtctgc     120
cctgcgggac cctgcaggaa tctttgagct ggtggaggtg gttggcaatg gaacctatgg     180
acaggtatac aagggcggc acgtcaagac tgggcagctg gctgccatta aggtcatgga      240
tgtcacagag gatgaggagg aagagatcaa acaggaaatc aacatgttaa agaagtactc     300
tcaccatcgc aatattgcca cctactatgg ggcctttatc aagaagagcc ctcctgggaa     360
cgatgaccag ctctggctgg tgatggagtt ctgcggtgct ggttcagtga ccgacctggt     420
aaagaacaca aaagggaacg cactgaagga ggattgcatt gcttacatct gcagggagat     480
tctcaggggt cttgcccatc tccatgccca caaggtgatc cacagagata tcaagggaca     540
aaatgtgctg ctgacagaga atgctgaagt caagctagtg gattttgggg tgagtgctca     600
gctggaccgc actgtgggca ggcggaacac tttcattgga accccatact ggatggctcc     660
agaagtcatt gcctgtgacg agaacccga tgccacctat gactacagga gtgacatttg      720
gtctctagga atcacagcca ttgaaatggc agagggagcc ccccctctgt gtgacatgca     780
ccctatgcgg gccctcttcc tcatccctcg gaaccctccc cccaggctca gtcaaagaa      840 atggtctaag aagttcactg acttcatcga cacgtgtctc atcaagactt acctga         896

<210> SEQ ID NO 2
<211> LENGTH: 1060
<212> TYPE: DNA
<213> ORGANISM: Mus musculus

<400> SEQUENCE: 2
cggcgcctgc agtggcgcgg ggagaggcga tcggccccgg atcccgcagc cctgcagccc      60
gcgtagaccg agctgccccg gcgccccgaa tcctgaagtc ccagttgagt cagaatggat     120
gaacaatcac aaggaatgca agggccgccc gttactcagt tccagccaca gaaggcatta     180
cggccagata tgggctataa tactttagcc aacttccgaa tagaaaagaa aattggtcgt     240
```

-continued

| | |
|---|---|
| ggacaattta gtgaagttta tagagcatcc tgtctcttgg atggagtgcc ggtagcgtta | 300 |
| aaaaaagtac agatatttga tttaatggat gccaaagcac gtgctgattg tatcaaagaa | 360 |
| atagacctcc ttaagcaact caaccatcca aatgtaatta aatactatgc atcattcatt | 420 |
| gaggataatg agctgaacat agttttggag ttagcagatg ctggtgacct ctccagaatg | 480 |
| ataaagcact ttaagaaaca aaagaggcta atccctgaga gaaccgtttg gaaatacttc | 540 |
| gttcagctct gcagtgcact ggaccacatg cattctcgaa gagtcatgca cagagatata | 600 |
| aaaccagcta atgtgttcat tacagccact ggggtagtaa actcggaga ccttgggctt | 660 |
| ggtcggtttt tcagctccaa aaccacagct gcacattctt tagtgggtac accttactac | 720 |
| atgtctccag agaaataca tgaaaatgga tacaacttca agtctgacat ctggtctctt | 780 |
| ggctgtctgc tatatgagat ggctgcactg cagagtcctt tctacggcga caagatgaac | 840 |
| ttgtattctc tgtgtaagaa gatagagcag tgtgactacc cgcctctccc gtcagatcac | 900 |
| tattcggagg agctacgaca gctagttaat atatgcatca acccagatcc agagaagcga | 960 |
| cccgacatcg cctatgttta tgatgtggca aagaggatgc atgcatgtac cgcaagcacc | 1020 |
| taaactgtac aagatcctga agcaggtcgt ctcgttccaa | 1060 |

<210> SEQ ID NO 3
<211> LENGTH: 1694
<212> TYPE: DNA
<213> ORGANISM: Mus musculus

<400> SEQUENCE: 3

| | |
|---|---|
| tggaacgaga cgacctgctc cggagagcag tagaaattag agccagggag ggaccgcggc | 60 |
| ggcagcagcc aaggcgaaag aggaaactgc gaagaggaa gctctgcggc agcccgagcc | 120 |
| tccctgcgct ccgcatcctc ccgctccgca tcccggcgcc gggcatcccc cggagcccgc | 180 |
| gccgcgcctc cggcgcccct tccccagcgc aaccctcggc cgcccacag cattagtctg | 240 |
| ccatggcccg ggagaacggc gagagcagct cctcctggaa aaagcaagca gaagacatta | 300 |
| agaagatctt cgagttcaag gagaccctcg gaactgggc cttttctgaa gttgttttag | 360 |
| ccgaggagaa agctactggg aagctcttcg cagtgaagtg catcccgaag aaggcgctga | 420 |
| agggcaagga gagcagcatc gagaacgaga ttgccgtgct tagaaagatt aagcatgaaa | 480 |
| acattgttgc cttggaagat atttatgaaa gcccaaatca cctctacctg gtcatgcaac | 540 |
| ttgtgtctgg tggagaactc ttcgatcgga tagtggagaa ggggttttac acagagaaag | 600 |
| atgccagcac tctcatccgc caggtcctgg atgccgtata ctatctccac agaatgggca | 660 |
| ttgtccacag ggacctcaag ccggagaatc tcttatacta cagtcaagac gaggagtcca | 720 |
| aaataatgat cagtgacttt ggcttgtcga aaatggaggg caaaggagat gtgatgtcca | 780 |
| cggcctgcgg gaccccaggc tatgttgctc cggaagttct cgcccagaaa ccgtacagca | 840 |
| aagctgtgga ctgctggtcc atcggggtga tcgcctatat cttgctctgt ggttaccctc | 900 |
| cttttttatga tgaaaatgac tcgaagctgt tgaacagat cctcaaggca gaatatgagt | 960 |
| ttgattcccc ctactgggat gacatctccg actctgccaa agacttcatt cggaatctga | 1020 |
| tggagaaaga cccaaataaa gatacacttg tgagcaggc agctcgacac ccatggatg | 1080 |
| ctggtgacac agcccttagc aaaaacattc acgaatctgt cagtgcccag atccggaaga | 1140 |
| attttgcaaa gagcaaatgg agacaagcgt ttaacgccac ggcagtcgtg agacatatgc | 1200 |
| ggaggctcca gcttggcagc agcctggaca gttcaaatgc aagtgtctca gcaacctca | 1260 |
| gtttggccag ccaaaaagat tgtgcgtctg gcaccttcca cgctctgtag tttccttct | 1320 |

-continued

```
tcttcgtcgg gggtcgcagg attcggagct gagaggagac ccaggcccac cactgtgaca    1380
acagggcaca ctggaagcaa gtgacccggc tctggaggtg aacccagggg gcagggccg     1440
gggaaggaga agcccctggc cggagcagct cctgcatcag aaaccccacc caccctgcat    1500
ggtgcacctg cataggactg gaagatagaa ggttttttat ggccatattt tatactgcaa    1560
ttctgatgtg ttcatttctc acaaactgta ctgactgact caaggggagc tggcgtcacg    1620
ggatctggtg ctgtatataa gaatcttgca aagctctaac tgaatggacc ttctagcagg    1680
tcgtctcgtt ccaa                                                     1694
```

<210> SEQ ID NO 4
<211> LENGTH: 2902
<212> TYPE: DNA
<213> ORGANISM: Mus musculus

<400> SEQUENCE: 4

```
cactagtgga tccaaagaat tcggcacgag gcgtgctcgg gtgcggctgt gacctctgag      60
cccgcggctc agcgcgcgct gctactgctg cccgacccac tccacctcgc ggtccccgca     120
ccatggagtc ggtggcctta ctccagcgcc cgagccaggc tccctcggcc tccgccctgg     180
cctcggagag cgcccggccg ctgcggacg ggctcatcaa gtcgcctaaa cctctgatga     240
agaagcaggc ggtgaagcgg caccatcaca acacaacct gcggcaccgc tacgagttcc      300
tggagacgct gggcaagggc acctacggga aggtgaagaa ggcacgagag agctcggggc      360
gtctggtggc catcaagtcc atcaggaaag acaaaatcaa agatgagcag gatctgctgc     420
acatacggag ggagattgag atcatgtctt cactcaacca cccccacatc attgccatcc     480
atgaagtgtt tgagaatagc agcaagattg tgattgtcat ggagtatgcc agccgaggcg     540
atctgtatga ttacatcagt gagcggccac ggctgagtga gcgggacgcc aggcatttct     600
tccgacagat cgtgtctgcc ctgcactact gccaccagaa cgggatcgtt caccgagatc     660
tcaagctgga aaacatcctt ctagatgcca atggaaacat caagattgct gactttggcc     720
tctccaacct gtaccacaaa gcaagttcc tccagacgtt ctgtgggagc cctctctacg      780
cctcgcctga gatagtcaac gggaagccct atgtgggccc agaggtggac agctggtctc      840
tgggcgttct cctgtacatc ctggtgcatg gcaccatgcc ctttgacggg caggatcata      900
aaacactggt gaagcaaatc agtaacgggc ttaccgtga gccgcccaag ccgtccgatg      960
cctgtggcct gatccggtgg ctgttaatgg tgaaccccac ccgtcgggcc acactggagg    1020
atgtagccag tcattggtgg gtcaactggg gttacaccac cggagtcggg gaacaggaag    1080
ccctgcgtga gggtgggcac cctagtggtg actttggccg ggcctccatg gcggactggt    1140
tacgtcgctc ctcgcgcccc ctcctggaga atggagccaa ggtgtgcagc ttcttcaagc    1200
agcacgtgcc gggaggtgga agcactgtac ctgggctgga gcggcaacat tctcttaaga    1260
agtcccgaaa ggagaatgac atggctcaaa atctgcaagg tgacccggct gaggatacct    1320
cttctcgccc tggcaagagc agccttaagc ttccgaaagg cattctcaag aaaaagtcct    1380
ctacctcgtc aggggaggta caggaggacc ctcaggaact cagaccggtg cctgatactc    1440
cagggcagcc tgtccctgct gtatccctgc tcccaaggaa aggcatcctt aagaagtctc    1500
gacagcgtga atctggttac tactcctctc cagagcccag cgagtctggg gaactcttag    1560
acgccagtga tgtgtttgtg agtggggacc ccgtggagca gaagtctcca caggcttcag    1620
ggctcctcct ccaccgcaag ggcattctca aactcaatgg caagttctcc cgcacagcct    1680
```

-continued

| | |
|---|---|
| tagaaggcac taccctagc acctttggct ccctggacca actggcctcc tcccatcctg | 1740 |
| cagcccggcc cagccgcccc tcaggggctg tgagtgagga cagcatcctg tcctccgagt | 1800 |
| cctttgacca attggacttg cctgaacgtc ttcccgaaac cccactgagg ggctgtgtgt | 1860 |
| ctgtggacaa cctgaggggg cttgagcagc ctccctcaga aggtctgaag cgatggtggc | 1920 |
| aggaatcctt gggggatagc tgcttttctc tgacagactg ccaagaggtg actgcagcct | 1980 |
| acagacaagc cctaggaatc tgctcaaagc tcagctgagg aagggagatg gtgccctagt | 2040 |
| atggggtagg ctctgagagg gtttgcagag gaaccctggg tcggattcct ccagtgaata | 2100 |
| gagtacatca agggctctac gtctgcagcc tgactgaacc tgaaagatga gagaaatcgc | 2160 |
| attgatgtgg aaaggaatgg gaacccttgc tgcccgagtg ttatagtggg gtggcctgaa | 2220 |
| ggtgcctacc tcctttgtgc catgagtgtc acccatgaca tttcccaccc tgttctctgg | 2280 |
| ctgcaccttc acataagttt ctgtttccat caaccaccag ggttagaacc ctgacttcct | 2340 |
| gggaggtaat gtgtagtgac tgccattatt tagagaggaa acagcctctg gtttccatct | 2400 |
| ctgctgctgt gcatctcaaa gacctgggaa gactcggacc gctgtttgac ttcatctcaa | 2460 |
| ggggaccaga tgcccctgga ccccatctta gatctcagag acttgaacct tgaagctgtt | 2520 |
| cctagtaccc agatgtggat ggatgctctg tttctcaggc caacgggacc tagaatgtgc | 2580 |
| tgacttattt atttttttgt gattctcact tctgtttttt ggttttgtt tgtttgtttg | 2640 |
| tttttgtttt taagtgaatt ttgctgcttt caataatgtg aatgctgtgt tctggggaac | 2700 |
| tccactgtgc cactgaagtt tatgtacaga gaagtatttg caatgatgt ccctctattc | 2760 |
| aaggggggtg gggggcgtttt tcaaatgtat gtcttgagca ctgtctggat tgagtctcca | 2820 |
| gtcccttcac acccaaggct ggccaccctc cctcatcttc atctgtggcc aaaaaaaaa | 2880 |
| aaaaaaaaaa aaaaaaaaa aa | 2902 |

<210> SEQ ID NO 5
<211> LENGTH: 3228
<212> TYPE: DNA
<213> ORGANISM: Mus musculus

<400> SEQUENCE: 5

| | |
|---|---|
| tggatccaaa gaattcggca cgaggcggag tcccgcctcg ccgcccctcg agcgccccca | 60 |
| gcttctctgc tggccggaac ctgcaccccg aaccaggaag cacctggcgg cgggcgcggg | 120 |
| atggctgggc ccagctgggg tctccctcgg ctggacggtt tcatccttac cgagcgcctg | 180 |
| ggcagtggca cgtacgccac ggtgtacaag gcctacgcca agaaggatac tcgggaagtg | 240 |
| gtagccataa aatgcgtggc caagaagagt ctcaacaagg cgtcagtgga aaacctcctg | 300 |
| actgagattg agatcctcaa gggcattcgg caccccccata tcgtgcagct gaaagacttc | 360 |
| cagtgggaca atgacaatat ctacctcatc atggagttct gtgcagggggg tgacctgtct | 420 |
| cgcttcattc atacccgcag gatcctgcct gagaaggtgg cccgtgtttt catgcagcag | 480 |
| ttggctagtg ccctgcagtt cctgcatgaa cgaaacatct ctcacttgga tctgaaaccg | 540 |
| cagaacatcc tgctgagctc tttggagaag ccccacctga aactggcaga ctttggcttt | 600 |
| gcccagcaca tgtccccgtg ggacgaaaaa cacgtgctcc gtggctcccc gctctatatg | 660 |
| gctcctgaga tggtgtgtcg gcggcagtat gatgcgcgtg tggacctctg gtctgtgggg | 720 |
| gtgatcctgt acgaagccct ctttgggcag cccccctttg cctccagatc gttctcagag | 780 |
| ctagaagaaa agattcgcag caatcgggtg attgaggtgc gtctggcagg gtctaggcat | 840 |
| ccaccgggga ttgagggact caaggcccag aagtttgttc agcactgcag tgcaggctct | 900 |

```
gggcgtttca tggcagtggg gcatgttctg tggtggaagc ctagagtctg gtccgttcct      960
gaggatccat atcagccacg acaggcaaca aatgaccagg cccaatcttc ccatagtccg     1020
gggctggagg caaataccca tttgatagga gactgataaa ggatgcttgg ctctcttcct     1080
gcacatcacc gggacttgcc atgatccact cagattaccc acagcaaaca cgtaccctta     1140
tgggggttcc taacaggcct tgggctttgg gctcagatgt tggagccttc tgtgatgtgt     1200
ctctgctcta tgcctctgta gctccctctt cggccccaac tctccctaga ctgccgggac     1260
ctgttgcagc gacttctaga gcgggacccc gcccgtcgaa tctccttcaa ggacttcttt     1320
gcccatccct gggtggacct ggagcacatg cccagtgggg agagcctggc acaggcaagg     1380
gcccttgtgg tggaggctgt gaagaaggac caggagggga atgctgccgc tgccctgtcg     1440
ctctactgca aggctctgga cttctttgta cctgcgctac actgtgagaa ccaggccatt     1500
cctataacct gtgtgcagag gggggcagga gttgggtcag gctccccatt cagagcttag     1560
gggagatggt gcagaagatc aacgtggaac tgagtatctg aagattgcaa agggcttact     1620
gtggggtagg ctttcaggac agcatcctca tatgaaccct tcaccttctg cagacgaagt     1680
ggatgcccag aggaaggagg caattaaggc gaaggtggga cagtatgtgt cccgggcaga     1740
ggagctcaaa gccattgtct cctcctccaa tcaggccctg ctaagacagg gcacaactgt     1800
ccaagagctg cttcgaggct gctccctcac catgagcctt tactctcaca tcagagatgg     1860
cccgtgacaa accacgcctc ctggctgccc tggaagtggc ctcagctgcc ctggccaagg     1920
aggaggaagc tggcaaagag caggatgccc tggacctgta ccagcacagc ctcggggagc     1980
tgctagtgct gttggcagca gaggcccag gccgaaggcg ggagctcctt cacaccgagg      2040
ttcagaacct catggctcga gctgaatacc tgaaggagca gatcaagata agggagtctc     2100
actgggaagc ggagagtctg gacaaagagg ggctgtcgga gtctgttcgt agttcttgca     2160
cactgcagtg acaccggaag gagcagcgga tggagcacaa ccctagagag aagctgcatt     2220
accaactcag gttgacacct gcacacctgg gaccttcctg gacgagcagc tcccacatgc     2280
tggttcccag cattcctctg agtgttctcc acccttgggg cgtctggtgg caggtgtact     2340
aagctctggg agaattactt gaatgtgacc ttgtcattag gtgactgctg gtctaagcct     2400
gtccggcttc aggacaccat caccccgttg tgttttgttc tgcaaagagg acgtcatgcc     2460
tcttcaggac acttgctacc agacagctgc tgtacctggg ccacccctcc ctgggagcct     2520
ttattccaac cctactttt ttcttgcact ggaatgggac actcggatac cctcagggac      2580
tacctacctg acagtatgct ctcggctctc agacctctcc agtcttcctg cgagctcaga     2640
gctgccatcc ttttcagttc tttaagacaa tccttcatgc atgaaagtca tgcccttgt      2700 aaaggtggaa tacatgtgag aaccccagac cttccctgcc ttggcatgga ggagggtcc     2760 tcatacccc acttacagct ctctttgagg ggatatgcca cactagtcac atggtggacc      2820
ctgagctaga gctgggtctt ggctgggtct tcccctctgt cctattaagc tatggataca     2880
tccacagctt atccctgta tgagctggag aagaacttac gtatctggag ttactggaag      2940
attgctcttt tttttttttct tctttaaaca ccccctcccc caggtcatca tcttgtttca    3000
gatttttatt caaattctta ttgaaggctg attttttgaat aaggagcaga ggagctgttc    3060
tgccacaaat gacccccaaa tgacaggcac tgagactttc tttcttcctt ccttccttcc    3120
ttccttcctt ccttccttcc ttccttcctt ccttccttcc tttctttctt tctttctttc    3180
tttctttctt tctttctttc tttctttctt tcttccttct tccttcct              3228
```

<210> SEQ ID NO 6
<211> LENGTH: 1035
<212> TYPE: DNA
<213> ORGANISM: Homo sapiens

<400> SEQUENCE: 6

| | | | | | |
|---|---|---|---|---|---|
| cgcatgagga | cgcgagtgaa | atagaccaag | gtggaatttc | caagggaaaa | gcttcggggt | 60 |
| ggttttggtc | catttctcca | gcgaagaagt | agacatggcg | agcgactccc | cggctcgaag | 120 |
| cctggatgaa | atagatctct | cggctctgag | ggaccctgca | gggatctttg | aattggtgga | 180 |
| acttgttgga | aatggaacat | acgggcaagt | ttataagggt | cgtcatgtca | aaacgggcca | 240 |
| gcttgcagcc | atcaaggtta | tggatgtcac | aggggatgaa | gaggaagaaa | tcaaacaaga | 300 |
| aattaacatg | ttgaagaaat | attctcatca | ccggaatatt | gctacatact | atggtgcttt | 360 |
| tatcaaaaag | aacccaccag | gcatggatga | ccaactttgg | ttggtgatgg | agttttgtgg | 420 |
| tgctggctct | gtcaccgacc | tgatcaagaa | cacaaaaggt | aacacgttga | agaggagtg | 480 |
| gattgcatac | atctgcaggg | aaatcttacg | ggggctgagt | cacctgcacc | agcataaagt | 540 |
| gattcatcga | gatattaaag | gcaaaatgt | cttgctgact | gaaaatgcag | aagttaaact | 600 |
| agtggacttt | ggagtcagtg | ctcagcttga | tcgaacagtg | gcaggagga | atactttcat | 660 |
| tggaactccc | tactggatgg | caccagaagt | tattgcctgt | gatgaaaacc | cagatgccac | 720 |
| atatgatttc | aagagtgact | tgtggtcttt | gggtatcacc | gccattgaaa | tggcagaagg | 780 |
| tgctcccct | ctctgtgaca | tgcacccat | gagagctctc | ttcctcatcc | cccggaatcc | 840 |
| agcgcctcgg | ctgaagtcta | agaagtggtc | aaaaaaaatt | ccagtcattt | attgagagct | 900 |
| gcttggtaaa | gaatcacagc | cagcgaccag | caacagaaca | attgatgaag | catccatta | 960 |
| tacgagacca | acctaatgag | cgacaggtcc | gcattcaact | caaggaccat | attgatagaa | 1020 |
| caaagaagaa | gcgag | | | | | 1035 |

<210> SEQ ID NO 7
<211> LENGTH: 4083
<212> TYPE: DNA
<213> ORGANISM: Homo sapiens

<400> SEQUENCE: 7

| | | | | | |
|---|---|---|---|---|---|
| atggcgagcg | actccccggc | tcgaagcctg | gatgaaatag | atctctcggc | tctgagggac | 60 |
| cctgcaggga | tctttgaatt | ggtggaactt | gttggaaatg | gaacatacgg | gcaagtttat | 120 |
| aagggtcgtc | atgtcaaaac | gggccagctt | gcagccatca | aggttatgga | tgtcacaggg | 180 |
| gatgaagagg | aagaaatcaa | acaagaaatt | aacatgttga | agaaatattc | tcatccgg | 240 |
| aatattgcta | catactatgg | tgcttttatc | aaaaagaacc | caccaggcat | ggatgaccaa | 300 |
| ctttggttgg | tgatggagtt | ttgtggtgct | ggctctgtca | ccgacctgat | caagaacaca | 360 |
| aaaggtaaca | cgttgaaaga | ggagtggatt | gcatacatct | gcagggaaat | cttacggggg | 420 |
| ctgagtcacc | tgcaccagca | taagtgatt | catcgagata | ttaaagggca | aaatgtcttg | 480 |
| ctgactgaaa | atgcagaagt | taaactagtg | gactttggag | tcagtgctca | gcttgatcga | 540 |
| acagtgggca | ggaggaatac | tttcattgga | actccctact | ggatggcacc | agaagttatt | 600 |
| gcctgtgatg | aaaacccaga | tgccacatat | gatttcaaga | gtgacttgtg | gtctttgggt | 660 |
| atcaccgcca | ttgaaatggc | agaaggtgct | cccctctct | gtgacatgca | ccccatgaga | 720 |
| gctctcttcc | tcatccccg | gaatccagcg | cctcggctga | agtctaagaa | gtggtcaaaa | 780 |
| aaattccagt | catttattga | gagctgcttg | gtaaagaatc | acagccagcg | accagcaaca | 840 |

-continued

```
gaacaattga tgaagcatcc atttatacga gaccaaccta atgagcgaca ggtccgcatt    900
caactcaagg accatattga tagaacaaag aagaagcgag gagaaaaaga tgagacagag    960
tatgagtaca gtggaagtga ggaagaagag gaggagaatg actcaggaga gcccagctcc   1020
atcctgaatc tgccagggga gtcgacgctg cggagggact ttctgaggct gcagctggcc   1080
aacaaggagc gttctgaggc cctacggagg cagcagctgg agcagcagca gcggagaat    1140
gaggagcaca agcggcagct gctggccgag cgtcagaagc gcatcgagga gcagaaagag   1200
cagaggcggc ggctggagga gcaacaaagg cgagagaagg agctgcggaa gcagcaggag   1260
agggagcagc gccggcacta tgaggagcag atgcgccggg aggaggagag gaggcgtgcg   1320
gagcatgaac aggaatacat caggcgcacg ttagaggagg agcagagaca gttagagatc   1380
ttgcagcagc agctactgca tgaacaagct ctacttctgg aatataagcg caaacaattg   1440
gaagaacaga gacaagcaga aagactgcag aggcagctaa agcaagaaag agactactta   1500
gtttcccttc agcatcagcg gcaggagcag aggcctgtgg agaagaagcc actgtaccat   1560
tacaaagaag gaatgagtcc tagtgagaag ccagcatggg ccaaggaggt agaagaacgg   1620
tcaaggctca accggcaaag ttcccctgcc atgcctcaca aggttgccaa caggatatct   1680
gaccccaacc tgcccccaag gtcggagtcc ttcagcatta gtggagttca gcctgctcga   1740
acaccccca tgctcagacc agtcgatccc cagatcccac atctggtagc tgtaaaatcc   1800
cagggacctg ccttgaccgc ctcccagtca gtgcacgagc agcccacaaa gggcctctct   1860
gggtttcagg aggctctgaa cgtgacctcc caccgcgtgg agatgccacg ccagaactca   1920
gatcccacct cggaaaatcc tcctctcccc actcgcattg aaaagtttga ccgaagctct   1980
tggttacgac aggaagaaga cattccacca aaggtgcctc aaagaacaac ttctatatcc   2040
ccagcattag ccagaaagaa ttctcctggg aatggtagtg ctctgggacc cagactagga   2100
tctcaaccca tcagagcaag caaccctgat ctccggagaa ctgagcccat cttggagagc   2160
cccttgcaga ggaccagcag tggcagttcc tccagctcca gcacccctag ctcccagccc   2220
agctcccaag gaggctccca gcctggatca caagcaggat ccagtgaacg caccagagtt   2280
cgagccaaca gtaagtcaga aggatcacct gtgcttcccc atgagcctgc caaggtgaaa   2340
ccagaagaat ccagggacat tacccggccc agtcgaccag ctagctacaa aaaagctata   2400
gatgaggatc tgacggcatt agccaaagaa ctaagagaac tccggattga agaaacaaac   2460
cgcccaatga agaaggtgac tgattactcc tcctccagtg aggagtcaga agtagcgag   2520
gaagaggagg aagatggaga gagcgagacc catgatggga cagtggctgt cagcgacata   2580
cccagactga taccaacagg agctccaggc agcaacgagc agtacaatgt gggaatggtg   2640
gggacgcatg ggctggagac ctctcatgcg gacagtttca gcggcagtat ttcaagagaa   2700
ggaaccttga tgattagaga gacgtctgga gagaagaagc gatctggcca cagtgacagc   2760
aatggctttg ctggccacat caacctccct gacctggtgc agcagagcca ttctccagct   2820
ggaaccccga ctgagggact ggggcgcgtc tcaacccatt cccaggagat ggactctggg   2880
actgaatatg gcatggggag cagcaccaaa gcctccttca ccccctttgt ggaccccaga   2940
gtataccaga cgtctcccac tgatgaagat gaagaggatg aggaatcatc agccgcagct   3000
ctgtttacta gcgaacttct taggcaagaa caggccaaac tcaatgaagc aagaaagatt   3060
tcggtggtaa atgtaaaccc aaccaacatt cggcctcata gcgacacacc agaaatcaga   3120
aaatacaaga aacgattcaa ctcagaaata ctttgtgcag ctctgtgggg tgtaaacctt   3180
```

-continued

```
ctggtgggga ctgaaaatgg cctgatgctt ttggaccgaa gtgggcaagg caaagtctat   3240
aatctgatca accggaggcg atttcagcag atggatgtgc tagagggact gaatgtcctt   3300
gtgacaattt caggaaagaa gaataagcta cgagtttact atctttcatg gttaagaaac   3360
agaatactac ataatgaccc agaagtagaa aagaaacaag gctggatcac tgttggggac   3420
ttggaaggct gtatacatta taaagttgtt aaatatgaaa ggatcaaatt tttggtgatt   3480
gccttaaaga atgctgtgga aatatatgct tgggctccta aaccgtatca taaattcatg   3540

gcatttaagt cttttgcaga tctccagcac aagcctctgc tagttgatct cacggtagaa   3600
gaaggtcaaa gattaaaggt tatttttggt tcacacactg gtttccatgt aattgatgtt   3660
gattcaggaa actcttatga tatctacata ccatctcata ttcagggcaa tatcactcct   3720
catgctattg tcatcttgcc taaaacagat ggaatggaaa tgcttgtttg ctatgaggat   3780
gagggggtgt atgtaaacac ctatggccgg ataactaagg atgtggtgct ccaatgggga   3840
gaaatgccca cgtctgtggc ctacattcat tccaatcaga taatgggctg ggcgagaaa    3900
gctattgaga tccggtcagt ggaaacagga catttggatg gagtatttat gcataagcga   3960
gctcaaaggt taaagtttct atgtgaaaga aatgataagg tattttttgc atccgtgcga   4020
tctggaggaa gtagccaagt gtttttcatg accctcaaca gaaattccat gatgaactgg   4080
taa                                                                 4083
```

```

<210> SEQ ID NO 8
<211> LENGTH: 275
<212> TYPE: PRT
<213> ORGANISM: Mus musculus

<400> SEQUENCE: 8

Met Gly Asp Pro Ala Pro Ala Arg Ser Leu Asp Asp Ile Asp Leu Ser
1               5                   10                  15

Ala Leu Arg Asp Pro Ala Gly Ile Phe Glu Leu Val Glu Val Val Gly
            20                  25                  30

Asn Gly Thr Tyr Gly Gln Val Tyr Lys Gly Arg His Val Lys Thr Gly
        35                  40                  45

Gln Leu Ala Ala Ile Lys Val Met Asp Val Thr Glu Asp Glu Glu Glu
    50                  55                  60

Glu Ile Lys Gln Glu Ile Asn Met Leu Lys Lys Tyr Ser His His Arg
65                  70                  75                  80

Asn Ile Ala Thr Tyr Tyr Gly Ala Phe Ile Lys Lys Ser Pro Pro Gly
                85                  90                  95

Asn Asp Asp Gln Leu Trp Leu Val Met Glu Phe Cys Gly Ala Gly Ser
            100                 105                 110

Val Thr Asp Leu Val Lys Asn Thr Lys Gly Asn Ala Leu Lys Glu Asp
        115                 120                 125

Cys Ile Ala Tyr Ile Cys Arg Glu Ile Leu Arg Gly Leu Ala His Leu
    130                 135                 140

His Ala His Lys Val Ile His Arg Asp Ile Lys Gly Gln Asn Val Leu
145                 150                 155                 160

Leu Thr Glu Asn Ala Glu Val Lys Leu Val Asp Phe Gly Val Ser Ala
                165                 170                 175

Gln Leu Asp Arg Thr Val Gly Arg Arg Asn Thr Phe Ile Gly Thr Pro
            180                 185                 190

Tyr Trp Met Ala Pro Glu Val Ile Ala Cys Asp Glu Asn Pro Asp Ala
        195                 200                 205
```

Thr Tyr Asp Tyr Arg Ser Asp Ile Trp Ser Leu Gly Ile Thr Ala Ile
    210                 215                 220

Glu Met Ala Glu Gly Ala Pro Pro Leu Cys Asp Met His Pro Met Arg
225                 230                 235                 240

Ala Leu Phe Leu Ile Pro Arg Asn Pro Pro Arg Leu Lys Ser Lys
                245                 250                 255

Lys Trp Ser Lys Lys Phe Thr Asp Phe Ile Asp Thr Cys Leu Ile Lys
                260                 265                 270

Thr Tyr Leu
        275

<210> SEQ ID NO 9
<211> LENGTH: 302
<212> TYPE: PRT
<213> ORGANISM: Mus musculus

<400> SEQUENCE: 9

Met Asp Glu Gln Ser Gln Gly Met Gln Gly Pro Pro Val Thr Gln Phe
1               5                   10                  15

Gln Pro Gln Lys Ala Leu Arg Pro Asp Met Gly Tyr Asn Thr Leu Ala
                20                  25                  30

Asn Phe Arg Ile Glu Lys Lys Ile Gly Arg Gly Gln Phe Ser Glu Val
            35                  40                  45

Tyr Arg Ala Ser Cys Leu Leu Asp Gly Val Pro Val Ala Leu Lys Lys
        50                  55                  60

Val Gln Ile Phe Asp Leu Met Asp Ala Lys Ala Arg Ala Asp Cys Ile
65                  70                  75                  80

Lys Glu Ile Asp Leu Leu Lys Gln Leu Asn His Pro Asn Val Ile Lys
                85                  90                  95

Tyr Tyr Ala Ser Phe Ile Glu Asp Asn Glu Leu Asn Ile Val Leu Glu
            100                 105                 110

Leu Ala Asp Ala Gly Asp Leu Ser Arg Met Ile Lys His Phe Lys Lys
        115                 120                 125

Gln Lys Arg Leu Ile Pro Glu Arg Thr Val Trp Lys Tyr Phe Val Gln
    130                 135                 140

Leu Cys Ser Ala Leu Asp His Met His Ser Arg Arg Val Met His Arg
145                 150                 155                 160

Asp Ile Lys Pro Ala Asn Val Phe Ile Thr Ala Thr Gly Val Val Lys
                165                 170                 175

Leu Gly Asp Leu Gly Leu Gly Arg Phe Phe Ser Ser Lys Thr Thr Ala
            180                 185                 190

Ala His Ser Leu Val Gly Thr Pro Tyr Tyr Met Ser Pro Glu Arg Ile
        195                 200                 205

His Glu Asn Gly Tyr Asn Phe Lys Ser Asp Ile Trp Ser Leu Gly Cys
    210                 215                 220

Leu Leu Tyr Glu Met Ala Ala Leu Gln Ser Pro Phe Tyr Gly Asp Lys
225                 230                 235                 240

Met Asn Leu Tyr Ser Leu Cys Lys Lys Ile Glu Gln Cys Asp Tyr Pro
                245                 250                 255

Pro Leu Pro Ser Asp His Tyr Ser Glu Glu Leu Arg Gln Leu Val Asn
            260                 265                 270

Ile Cys Ile Asn Pro Asp Pro Glu Lys Arg Pro Asp Ile Ala Tyr Val
        275                 280                 285

Tyr Asp Val Ala Lys Arg Met His Ala Cys Thr Ala Ser Thr
    290                 295                 300

```
<210> SEQ ID NO 10
<211> LENGTH: 355
<212> TYPE: PRT
<213> ORGANISM: Mus musculus

<400> SEQUENCE: 10

Met Ala Arg Glu Asn Gly Glu Ser Ser Ser Trp Lys Lys Gln Ala
1               5                   10                  15

Glu Asp Ile Lys Lys Ile Phe Glu Phe Lys Glu Thr Leu Gly Thr Gly
                20                  25                  30

Ala Phe Ser Glu Val Val Leu Ala Glu Glu Lys Ala Thr Gly Lys Leu
            35                  40                  45

Phe Ala Val Lys Cys Ile Pro Lys Lys Ala Leu Lys Gly Lys Glu Ser
50                  55                  60

Ser Ile Glu Asn Glu Ile Ala Val Leu Arg Lys Ile Lys His Glu Asn
65                  70                  75                  80

Ile Val Ala Leu Glu Asp Ile Tyr Glu Ser Pro Asn His Leu Tyr Leu
                85                  90                  95

Val Met Gln Leu Val Ser Gly Gly Glu Leu Phe Asp Arg Ile Val Glu
                100                 105                 110

Lys Gly Phe Tyr Thr Glu Lys Asp Ala Ser Thr Leu Ile Arg Gln Val
            115                 120                 125

Leu Asp Ala Val Tyr Tyr Leu His Arg Met Gly Ile Val His Arg Asp
130                 135                 140

Leu Lys Pro Glu Asn Leu Leu Tyr Tyr Ser Gln Asp Glu Glu Ser Lys
145                 150                 155                 160

Ile Met Ile Ser Asp Phe Gly Leu Ser Lys Met Glu Gly Lys Gly Asp
                165                 170                 175

Val Met Ser Thr Ala Cys Gly Thr Pro Gly Tyr Val Ala Pro Glu Val
                180                 185                 190

Leu Ala Gln Lys Pro Tyr Ser Lys Ala Val Asp Cys Trp Ser Ile Gly
            195                 200                 205

Val Ile Ala Tyr Ile Leu Leu Cys Gly Tyr Pro Pro Phe Tyr Asp Glu
210                 215                 220

Asn Asp Ser Lys Leu Phe Glu Gln Ile Leu Lys Ala Glu Tyr Glu Phe
225                 230                 235                 240

Asp Ser Pro Tyr Trp Asp Asp Ile Ser Asp Ser Ala Lys Asp Phe Ile
                245                 250                 255

Arg Asn Leu Met Glu Lys Asp Pro Asn Lys Arg Tyr Thr Cys Glu Gln
                260                 265                 270

Ala Ala Arg His Pro Trp Ile Ala Gly Asp Thr Ala Leu Ser Lys Asn
            275                 280                 285

Ile His Glu Ser Val Ser Ala Gln Ile Arg Lys Asn Phe Ala Lys Ser
        290                 295                 300

Lys Trp Arg Gln Ala Phe Asn Ala Thr Ala Val Val Arg His Met Arg
305                 310                 315                 320

Arg Leu Gln Leu Gly Ser Ser Leu Asp Ser Ser Asn Ala Ser Val Ser
                325                 330                 335

Ser Asn Leu Ser Leu Ala Ser Gln Lys Asp Cys Ala Ser Gly Thr Phe
                340                 345                 350

His Ala Leu
        355
```

```
<210> SEQ ID NO 11
<211> LENGTH: 631
<212> TYPE: PRT
<213> ORGANISM: Mus musculus

<400> SEQUENCE: 11

Met Glu Ser Val Ala Leu Leu Gln Arg Pro Ser Gln Ala Pro Ser Ala
1               5                   10                  15

Ser Ala Leu Ala Ser Glu Ser Ala Arg Pro Leu Ala Asp Gly Leu Ile
            20                  25                  30

Lys Ser Pro Lys Pro Leu Met Lys Lys Gln Ala Val Lys Arg His His
        35                  40                  45

His Lys His Asn Leu Arg His Arg Tyr Glu Phe Leu Glu Thr Leu Gly
    50                  55                  60

Lys Gly Thr Tyr Gly Lys Val Lys Ala Arg Glu Ser Ser Gly Arg
65                  70                  75                  80

Leu Val Ala Ile Lys Ser Ile Arg Lys Asp Lys Ile Lys Asp Glu Gln
                85                  90                  95

Asp Leu Leu His Ile Arg Arg Glu Ile Glu Ile Met Ser Ser Leu Asn
            100                 105                 110

His Pro His Ile Ile Ala Ile His Glu Val Phe Glu Asn Ser Ser Lys
        115                 120                 125

Ile Val Ile Val Met Glu Tyr Ala Ser Arg Gly Asp Leu Tyr Asp Tyr
    130                 135                 140

Ile Ser Glu Arg Pro Arg Leu Ser Glu Arg Asp Ala Arg His Phe Phe
145                 150                 155                 160

Arg Gln Ile Val Ser Ala Leu His Tyr Cys His Gln Asn Gly Ile Val
                165                 170                 175

His Arg Asp Leu Lys Leu Glu Asn Ile Leu Leu Asp Ala Asn Gly Asn
            180                 185                 190

Ile Lys Ile Ala Asp Phe Gly Leu Ser Asn Leu Tyr His Lys Gly Lys
        195                 200                 205

Phe Leu Gln Thr Phe Cys Gly Ser Pro Leu Tyr Ala Ser Pro Glu Ile
    210                 215                 220

Val Asn Gly Lys Pro Tyr Val Gly Pro Glu Val Asp Ser Trp Ser Leu
225                 230                 235                 240

Gly Val Leu Leu Tyr Ile Leu Val His Gly Thr Met Pro Phe Asp Gly
                245                 250                 255

Gln Asp His Lys Thr Leu Val Lys Gln Ile Ser Asn Gly Ala Tyr Arg
            260                 265                 270

Glu Pro Pro Lys Pro Ser Asp Ala Cys Gly Leu Ile Arg Trp Leu Leu
        275                 280                 285

Met Val Asn Pro Thr Arg Arg Ala Thr Leu Glu Asp Val Ala Ser His
    290                 295                 300

Trp Trp Val Asn Trp Gly Tyr Thr Thr Gly Val Gly Glu Gln Glu Ala
305                 310                 315                 320

Leu Arg Glu Gly Gly His Pro Ser Gly Asp Phe Gly Arg Ala Ser Met
                325                 330                 335

Ala Asp Trp Leu Arg Arg Ser Ser Arg Pro Leu Leu Glu Asn Gly Ala
            340                 345                 350

Lys Val Cys Ser Phe Phe Lys Gln His Val Pro Gly Gly Gly Ser Thr
        355                 360                 365

Val Pro Gly Leu Glu Arg Gln His Ser Leu Lys Lys Ser Arg Lys Glu
    370                 375                 380
```

-continued

```
Asn Asp Met Ala Gln Asn Leu Gln Gly Asp Pro Ala Glu Asp Thr Ser
385                 390                 395                 400

Ser Arg Pro Gly Lys Ser Ser Leu Lys Leu Pro Lys Gly Ile Leu Lys
                405                 410                 415

Lys Lys Ser Ser Thr Ser Ser Gly Glu Val Gln Glu Asp Pro Gln Glu
            420                 425                 430

Leu Arg Pro Val Pro Asp Thr Pro Gly Gln Pro Val Pro Ala Val Ser
                435                 440                 445

Leu Leu Pro Arg Lys Gly Ile Leu Lys Lys Ser Arg Gln Arg Glu Ser
        450                 455                 460

Gly Tyr Tyr Ser Ser Pro Glu Pro Ser Glu Ser Gly Glu Leu Leu Asp
465                 470                 475                 480

Ala Ser Asp Val Phe Val Ser Gly Asp Pro Val Glu Gln Lys Ser Pro
                485                 490                 495

Gln Ala Ser Gly Leu Leu Leu His Arg Lys Gly Ile Leu Lys Leu Asn
            500                 505                 510

Gly Lys Phe Ser Arg Thr Ala Leu Glu Gly Thr Thr Pro Ser Thr Phe
        515                 520                 525

Gly Ser Leu Asp Gln Leu Ala Ser Ser His Pro Ala Ala Arg Pro Ser
530                 535                 540

Arg Pro Ser Gly Ala Val Ser Glu Asp Ser Ile Leu Ser Ser Glu Ser
545                 550                 555                 560

Phe Asp Gln Leu Asp Leu Pro Glu Arg Leu Pro Glu Thr Pro Leu Arg
                565                 570                 575

Gly Cys Val Ser Val Asp Asn Leu Arg Gly Leu Glu Gln Pro Pro Ser
            580                 585                 590

Glu Gly Leu Lys Arg Trp Trp Gln Glu Ser Leu Gly Asp Ser Cys Phe
        595                 600                 605

Ser Leu Thr Asp Cys Gln Glu Val Thr Ala Ala Tyr Arg Gln Ala Leu
            610                 615                 620

Gly Ile Cys Ser Lys Leu Ser
625                 630

<210> SEQ ID NO 12
<211> LENGTH: 311
<212> TYPE: PRT
<213> ORGANISM: Mus musculus

<400> SEQUENCE: 12

Met Ala Gly Pro Ser Trp Gly Leu Pro Arg Leu Asp Gly Phe Ile Leu
1               5                   10                  15

Thr Glu Arg Leu Gly Ser Gly Thr Tyr Ala Thr Val Tyr Lys Ala Tyr
                20                  25                  30

Ala Lys Lys Asp Thr Arg Glu Val Val Ala Ile Lys Cys Val Ala Lys
            35                  40                  45

Lys Ser Leu Asn Lys Ala Ser Val Glu Asn Leu Leu Thr Glu Ile Glu
        50                  55                  60

Ile Leu Lys Gly Ile Arg His Pro His Ile Val Gln Leu Lys Asp Phe
65                  70                  75                  80

Gln Trp Asp Asn Asp Asn Ile Tyr Leu Ile Met Glu Phe Cys Ala Gly
                85                  90                  95

Gly Asp Leu Ser Arg Phe Ile His Thr Arg Arg Ile Leu Pro Glu Lys
            100                 105                 110

Val Ala Arg Val Phe Met Gln Gln Leu Ala Ser Ala Leu Gln Phe Leu
        115                 120                 125
```

```
His Glu Arg Asn Ile Ser His Leu Asp Leu Lys Pro Gln Asn Ile Leu
    130                 135                 140

Leu Ser Ser Leu Glu Lys Pro His Leu Lys Leu Ala Asp Phe Gly Phe
145                 150                 155                 160

Ala Gln His Met Ser Pro Trp Asp Glu Lys His Val Leu Arg Gly Ser
                165                 170                 175

Pro Leu Tyr Met Ala Pro Glu Met Val Cys Arg Arg Gln Tyr Asp Ala
            180                 185                 190

Arg Val Asp Leu Trp Ser Val Gly Val Ile Leu Tyr Glu Ala Leu Phe
        195                 200                 205

Gly Gln Pro Pro Phe Ala Ser Arg Ser Phe Ser Glu Leu Glu Glu Lys
    210                 215                 220

Ile Arg Ser Asn Arg Val Ile Glu Val Arg Leu Ala Gly Ser Arg His
225                 230                 235                 240

Pro Pro Gly Ile Glu Gly Leu Lys Ala Gln Lys Phe Val Gln His Cys
                245                 250                 255

Ser Ala Gly Ser Gly Arg Phe Met Ala Val Gly His Val Leu Trp Trp
            260                 265                 270

Lys Pro Arg Val Trp Ser Val Pro Glu Asp Pro Tyr Gln Pro Arg Gln
        275                 280                 285

Ala Thr Asn Asp Gln Ala Gln Ser Ser His Ser Pro Gly Leu Glu Ala
    290                 295                 300

Asn Thr His Leu Ile Gly Asp
305                 310

<210> SEQ ID NO 13
<211> LENGTH: 266
<212> TYPE: PRT
<213> ORGANISM: Homo sapiens

<400> SEQUENCE: 13

Met Ala Ser Asp Ser Pro Ala Arg Ser Leu Asp Glu Ile Asp Leu Ser
1               5                   10                  15

Ala Leu Arg Asp Pro Ala Gly Ile Phe Glu Leu Val Glu Leu Val Gly
                20                  25                  30

Asn Gly Thr Tyr Gly Gln Val Tyr Lys Gly Arg His Val Lys Thr Gly
            35                  40                  45

Gln Leu Ala Ala Ile Lys Val Met Asp Val Thr Gly Asp Glu Glu Glu
    50                  55                  60

Glu Ile Lys Gln Glu Ile Asn Met Leu Lys Lys Tyr Ser His His Arg
65                  70                  75                  80

Asn Ile Ala Thr Tyr Tyr Gly Ala Phe Ile Lys Lys Asn Pro Pro Gly
                85                  90                  95

Met Asp Asp Gln Leu Trp Leu Val Met Glu Phe Cys Gly Ala Gly Ser
            100                 105                 110

Val Thr Asp Leu Ile Lys Asn Thr Lys Gly Asn Thr Leu Lys Glu Glu
        115                 120                 125

Trp Ile Ala Tyr Ile Cys Arg Glu Ile Leu Arg Gly Leu Ser His Leu
    130                 135                 140

His Gln His Lys Val Ile His Arg Asp Ile Lys Gly Gln Asn Val Leu
145                 150                 155                 160

Leu Thr Glu Asn Ala Glu Val Lys Leu Val Asp Phe Gly Val Ser Ala
                165                 170                 175

Gln Leu Asp Arg Thr Val Gly Arg Arg Asn Thr Phe Ile Gly Thr Pro
```

```
                    180                 185                 190
Tyr Trp Met Ala Pro Glu Val Ile Ala Cys Asp Glu Asn Pro Asp Ala
            195                 200                 205

Thr Tyr Asp Phe Lys Ser Asp Leu Trp Ser Leu Gly Ile Thr Ala Ile
    210                 215                 220

Glu Met Ala Glu Gly Ala Pro Pro Leu Cys Asp Met His Pro Met Arg
225                 230                 235                 240

Ala Leu Phe Leu Ile Pro Arg Asn Pro Ala Pro Arg Leu Lys Ser Lys
                245                 250                 255

Lys Trp Ser Lys Lys Ile Pro Val Ile Tyr
                260                 265

<210> SEQ ID NO 14
<211> LENGTH: 1360
<212> TYPE: PRT
<213> ORGANISM: Homo sapiens

<400> SEQUENCE: 14

Met Ala Ser Asp Ser Pro Ala Arg Ser Leu Asp Glu Ile Asp Leu Ser
1               5                   10                  15

Ala Leu Arg Asp Pro Ala Gly Ile Phe Glu Leu Val Glu Leu Val Gly
            20                  25                  30

Asn Gly Thr Tyr Gly Gln Val Tyr Lys Gly Arg His Val Lys Thr Gly
        35                  40                  45

Gln Leu Ala Ala Ile Lys Val Met Asp Val Thr Gly Asp Glu Glu Glu
    50                  55                  60

Glu Ile Lys Gln Glu Ile Asn Met Leu Lys Lys Tyr Ser His His Arg
65                  70                  75                  80

Asn Ile Ala Thr Tyr Tyr Gly Ala Phe Ile Lys Lys Asn Pro Pro Gly
                85                  90                  95

Met Asp Asp Gln Leu Trp Leu Val Met Glu Phe Cys Gly Ala Gly Ser
            100                 105                 110

Val Thr Asp Leu Ile Lys Asn Thr Lys Gly Asn Thr Leu Lys Glu Glu
        115                 120                 125

Trp Ile Ala Tyr Ile Cys Arg Glu Ile Leu Arg Gly Leu Ser His Leu
    130                 135                 140

His Gln His Lys Val Ile His Arg Asp Ile Lys Gly Gln Asn Val Leu
145                 150                 155                 160

Leu Thr Glu Asn Ala Glu Val Lys Leu Val Asp Phe Gly Val Ser Ala
                165                 170                 175

Gln Leu Asp Arg Thr Val Gly Arg Arg Asn Thr Phe Ile Gly Thr Pro
            180                 185                 190

Tyr Trp Met Ala Pro Glu Val Ile Ala Cys Asp Glu Asn Pro Asp Ala
        195                 200                 205

Thr Tyr Asp Phe Lys Ser Asp Leu Trp Ser Leu Gly Ile Thr Ala Ile
    210                 215                 220

Glu Met Ala Glu Gly Ala Pro Pro Leu Cys Asp Met His Pro Met Arg
225                 230                 235                 240

Ala Leu Phe Leu Ile Pro Arg Asn Pro Ala Pro Arg Leu Lys Ser Lys
                245                 250                 255

Lys Trp Ser Lys Lys Phe Gln Ser Phe Ile Glu Ser Cys Leu Val Lys
            260                 265                 270

Asn His Ser Gln Arg Pro Ala Thr Glu Gln Leu Met Lys His Pro Phe
        275                 280                 285
```

```
Ile Arg Asp Gln Pro Asn Glu Arg Gln Val Arg Ile Gln Leu Lys Asp
    290                 295                 300

His Ile Asp Arg Thr Lys Lys Arg Gly Glu Lys Asp Thr Glu
305                 310                 315                 320

Tyr Glu Tyr Ser Gly Ser Glu Glu Glu Glu Asn Asp Ser Gly
                    325                 330                 335

Glu Pro Ser Ser Ile Leu Asn Leu Pro Gly Glu Ser Thr Leu Arg Arg
                340                 345                 350

Asp Phe Leu Arg Leu Gln Leu Ala Asn Lys Glu Arg Ser Glu Ala Leu
                355                 360                 365

Arg Arg Gln Gln Leu Glu Gln Gln Arg Glu Asn Glu His Lys
370                 375                 380

Arg Gln Leu Leu Ala Glu Arg Gln Lys Arg Ile Glu Glu Gln Lys Glu
385                 390                 395                 400

Gln Arg Arg Arg Leu Glu Glu Gln Arg Arg Glu Lys Glu Leu Arg
                405                 410                 415

Lys Gln Gln Glu Arg Glu Gln Arg Arg His Tyr Glu Glu Gln Met Arg
                420                 425                 430

Arg Glu Glu Arg Arg Arg Ala Glu His Glu Gln Glu Tyr Ile Arg
    435                 440                 445

Arg Gln Leu Glu Glu Gln Arg Gln Leu Glu Ile Leu Gln Gln Gln
    450                 455                 460

Leu Leu His Glu Gln Ala Leu Leu Glu Tyr Lys Arg Lys Gln Leu
465                 470                 475                 480

Glu Glu Gln Arg Gln Ala Glu Arg Leu Gln Arg Gln Leu Lys Gln Glu
                485                 490                 495

Arg Asp Tyr Leu Val Ser Leu Gln His Gln Arg Gln Glu Gln Arg Pro
                500                 505                 510

Val Glu Lys Lys Pro Leu Tyr His Tyr Lys Glu Gly Met Ser Pro Ser
                515                 520                 525

Glu Lys Pro Ala Trp Ala Lys Glu Val Glu Arg Ser Arg Leu Asn
    530                 535                 540

Arg Gln Ser Ser Pro Ala Met Pro His Lys Val Ala Asn Arg Ile Ser
545                 550                 555                 560

Asp Pro Asn Leu Pro Pro Arg Ser Glu Ser Phe Ser Ile Ser Gly Val
                565                 570                 575

Gln Pro Ala Arg Thr Pro Pro Met Leu Arg Pro Val Asp Pro Gln Ile
                580                 585                 590

Pro His Leu Val Ala Val Lys Ser Gln Gly Pro Ala Leu Thr Ala Ser
        595                 600                 605

Gln Ser Val His Glu Gln Pro Thr Lys Gly Leu Ser Gly Phe Gln Glu
    610                 615                 620

Ala Leu Asn Val Thr Ser His Arg Val Glu Met Pro Arg Gln Asn Ser
625                 630                 635                 640

Asp Pro Thr Ser Glu Asn Pro Pro Leu Pro Thr Arg Ile Glu Lys Phe
                645                 650                 655

Asp Arg Ser Ser Trp Leu Arg Gln Glu Glu Asp Ile Pro Pro Lys Val
                660                 665                 670

Pro Gln Arg Thr Thr Ser Ile Ser Pro Ala Leu Ala Arg Lys Asn Ser
        675                 680                 685

Pro Gly Asn Gly Ser Ala Leu Gly Pro Arg Leu Gly Ser Gln Pro Ile
    690                 695                 700

Arg Ala Ser Asn Pro Asp Leu Arg Arg Thr Glu Pro Ile Leu Glu Ser
```

-continued

```
                705                 710                 715                 720
Pro Leu Gln Arg Thr Ser Ser Gly Ser Ser Ser Ser Ser Thr Pro
                725                 730                 735
Ser Ser Gln Pro Ser Ser Gln Gly Gly Ser Gln Pro Gly Ser Gln Ala
                740                 745                 750
Gly Ser Ser Glu Arg Thr Arg Val Arg Ala Asn Ser Lys Ser Glu Gly
                755                 760                 765
Ser Pro Val Leu Pro His Glu Pro Ala Lys Val Lys Pro Glu Glu Ser
        770                 775                 780
Arg Asp Ile Thr Arg Pro Ser Arg Pro Ala Ser Tyr Lys Lys Ala Ile
785                 790                 795                 800
Asp Glu Asp Leu Thr Ala Leu Ala Lys Glu Leu Arg Glu Leu Arg Ile
                805                 810                 815
Glu Glu Thr Asn Arg Pro Met Lys Lys Val Thr Asp Tyr Ser Ser Ser
                820                 825                 830
Ser Glu Glu Ser Glu Ser Ser Glu Glu Glu Glu Asp Gly Glu Ser
        835                 840                 845
Glu Thr His Asp Gly Thr Val Ala Val Ser Asp Ile Pro Arg Leu Ile
        850                 855                 860
Pro Thr Gly Ala Pro Gly Ser Asn Glu Gln Tyr Asn Val Gly Met Val
865                 870                 875                 880
Gly Thr His Gly Leu Glu Thr Ser His Ala Asp Ser Phe Ser Gly Ser
                885                 890                 895
Ile Ser Arg Glu Gly Thr Leu Met Ile Arg Glu Thr Ser Gly Glu Lys
                900                 905                 910
Lys Arg Ser Gly His Ser Asp Ser Asn Gly Phe Ala Gly His Ile Asn
                915                 920                 925
Leu Pro Asp Leu Val Gln Gln Ser His Ser Pro Ala Gly Thr Pro Thr
        930                 935                 940
Glu Gly Leu Gly Arg Val Ser Thr His Ser Gln Glu Met Asp Ser Gly
945                 950                 955                 960
Thr Glu Tyr Gly Met Gly Ser Ser Lys Ala Ser Phe Thr Pro Phe
                965                 970                 975
Val Asp Pro Arg Val Tyr Gln Thr Ser Pro Thr Asp Glu Asp Glu Glu
                980                 985                 990
Asp Glu Glu Ser Ser Ala Ala Ala Leu Phe Thr Ser Glu Leu Leu Arg
        995                 1000                1005
Gln Glu Gln Ala Lys Leu Asn Glu Ala Arg Lys Ile Ser Val Val
        1010                1015                1020
Asn Val Asn Pro Thr Asn Ile Arg Pro His Ser Asp Thr Pro Glu
        1025                1030                1035
Ile Arg Lys Tyr Lys Lys Arg Phe Asn Ser Glu Ile Leu Cys Ala
        1040                1045                1050
Ala Leu Trp Gly Val Asn Leu Leu Val Gly Thr Glu Asn Gly Leu
        1055                1060                1065
Met Leu Leu Asp Arg Ser Gly Gln Gly Lys Val Tyr Asn Leu Ile
        1070                1075                1080
Asn Arg Arg Arg Phe Gln Gln Met Asp Val Leu Glu Gly Leu Asn
        1085                1090                1095
Val Leu Val Thr Ile Ser Gly Lys Lys Asn Lys Leu Arg Val Tyr
        1100                1105                1110
Tyr Leu Ser Trp Leu Arg Asn Arg Ile Leu His Asn Asp Pro Glu
        1115                1120                1125
```

-continued

```
Val Glu Lys Lys Gln Gly Trp Ile Thr Val Gly Asp Leu Glu Gly
    1130                1135                1140
Cys Ile His Tyr Lys Val Val Lys Tyr Glu Arg Ile Lys Phe Leu
    1145                1150                1155
Val Ile Ala Leu Lys Asn Ala Val Glu Ile Tyr Ala Trp Ala Pro
    1160                1165                1170
Lys Pro Tyr His Lys Phe Met Ala Phe Lys Ser Phe Ala Asp Leu
    1175                1180                1185
Gln His Lys Pro Leu Leu Val Asp Leu Thr Val Glu Glu Gly Gln
    1190                1195                1200
Arg Leu Lys Val Ile Phe Gly Ser His Thr Gly Phe His Val Ile
    1205                1210                1215
Asp Val Asp Ser Gly Asn Ser Tyr Asp Ile Tyr Ile Pro Ser His
    1220                1225                1230
Ile Gln Gly Asn Ile Thr Pro His Ala Ile Val Ile Leu Pro Lys
    1235                1240                1245
Thr Asp Gly Met Glu Met Leu Val Cys Tyr Glu Asp Glu Gly Val
    1250                1255                1260
Tyr Val Asn Thr Tyr Gly Arg Ile Thr Lys Asp Val Val Leu Gln
    1265                1270                1275
Trp Gly Glu Met Pro Thr Ser Val Ala Tyr Ile His Ser Asn Gln
    1280                1285                1290
Ile Met Gly Trp Gly Glu Lys Ala Ile Glu Ile Arg Ser Val Glu
    1295                1300                1305
Thr Gly His Leu Asp Gly Val Phe Met His Lys Arg Ala Gln Arg
    1310                1315                1320
Leu Lys Phe Leu Cys Glu Arg Asn Asp Lys Val Phe Phe Ala Ser
    1325                1330                1335
Val Arg Ser Gly Gly Ser Ser Gln Val Phe Phe Met Thr Leu Asn
    1340                1345                1350
Arg Asn Ser Met Met Asn Trp
    1355                1360

<210> SEQ ID NO 15
<211> LENGTH: 25
<212> TYPE: DNA
<213> ORGANISM: Artificial Sequence
<220> FEATURE:
<223> OTHER INFORMATION: oligonucleotide primer

<400> SEQUENCE: 15
atggcgagcg actccccggc tcgaa                                           25

<210> SEQ ID NO 16
<211> LENGTH: 29
<212> TYPE: DNA
<213> ORGANISM: Artificial Sequence
<220> FEATURE:
<223> OTHER INFORMATION: oligonucleotide primer

<400> SEQUENCE: 16
ccagttcatc atggaatttc tgttgaggg                                       29

<210> SEQ ID NO 17
<211> LENGTH: 7
<212> TYPE: PRT
<213> ORGANISM: Artificial Sequence
<220> FEATURE:
```

<223> OTHER INFORMATION: peptide

<400> SEQUENCE: 17

Leu Arg Arg Ala Ser Leu Gly
1               5

<210> SEQ ID NO 18
<211> LENGTH: 13
<212> TYPE: PRT
<213> ORGANISM: Artificial Sequence
<220> FEATURE:
<223> OTHER INFORMATION: peptide

<400> SEQUENCE: 18

Arg Lys Ile Ser Ala Ser Glu Phe Asp Arg Pro Leu Arg
1               5                   10

<210> SEQ ID NO 19
<211> LENGTH: 18
<212> TYPE: PRT
<213> ORGANISM: Artificial Sequence
<220> FEATURE:
<223> OTHER INFORMATION: peptide

<400> SEQUENCE: 19

Lys Lys Arg Phe Ser Phe Lys Lys Ser Phe Lys Leu Ser Gly Phe Ser
1               5                   10                  15

Phe Lys

<210> SEQ ID NO 20
<211> LENGTH: 9
<212> TYPE: PRT
<213> ORGANISM: Artificial Sequence
<220> FEATURE:
<223> OTHER INFORMATION: peptide

<400> SEQUENCE: 20

Gln Lys Arg Pro Ser Gln Arg Ser Lys
1               5

<210> SEQ ID NO 21
<211> LENGTH: 13
<212> TYPE: PRT
<213> ORGANISM: Artificial Sequence
<220> FEATURE:
<223> OTHER INFORMATION: peptide

<400> SEQUENCE: 21

Lys Lys Ala Leu Arg Arg Gln Glu Thr Val Asp Ala Leu
1               5                   10

<210> SEQ ID NO 22
<211> LENGTH: 14
<212> TYPE: PRT
<213> ORGANISM: Artificial Sequence
<220> FEATURE:
<223> OTHER INFORMATION: peptide

<400> SEQUENCE: 22

Pro Leu Ala Arg Thr Leu Ser Val Ala Gly Leu Pro Gly Lys
1               5                   10

<210> SEQ ID NO 23
<211> LENGTH: 10
<212> TYPE: PRT
<213> ORGANISM: Artificial Sequence

```
<220> FEATURE:
<223> OTHER INFORMATION: peptide

<400> SEQUENCE: 23

Arg Arg Arg Asp Asp Asp Ser Asp Asp Asp
 1               5                  10

<210> SEQ ID NO 24
<211> LENGTH: 8
<212> TYPE: PRT
<213> ORGANISM: Artificial Sequence
<220> FEATURE:
<223> OTHER INFORMATION: peptide
<221> NAME/KEY: MOD_RES
<222> LOCATION: (1)..(1)
<223> OTHER INFORMATION: ACETYLATION

<400> SEQUENCE: 24

Ser Pro Gly Arg Arg Arg Arg Lys
 1               5

<210> SEQ ID NO 25
<211> LENGTH: 10
<212> TYPE: PRT
<213> ORGANISM: Artificial Sequence
<220> FEATURE:
<223> OTHER INFORMATION: peptide

<400> SEQUENCE: 25

Pro Lys Thr Pro Lys Lys Ala Lys Lys Leu
 1               5                  10

<210> SEQ ID NO 26
<211> LENGTH: 9
<212> TYPE: PRT
<213> ORGANISM: Artificial Sequence
<220> FEATURE:
<223> OTHER INFORMATION: peptide

<400> SEQUENCE: 26

Ala Pro Arg Thr Pro Gly Gly Arg Arg
 1               5

<210> SEQ ID NO 27
<211> LENGTH: 20
<212> TYPE: PRT
<213> ORGANISM: Artificial Sequence
<220> FEATURE:
<223> OTHER INFORMATION: peptide

<400> SEQUENCE: 27

Glu Ala Ala Glu Ala Glu Pro Ala Glu Pro Ser Ser Pro Ala Ala Glu
 1               5                  10                  15

Ala Glu Gly Ala
            20

<210> SEQ ID NO 28
<211> LENGTH: 12
<212> TYPE: PRT
<213> ORGANISM: Artificial Sequence
<220> FEATURE:
<223> OTHER INFORMATION: peptide

<400> SEQUENCE: 28

Leu Met Glu Cys Arg Asn Ser Pro Val Ala Lys Thr
 1               5                  10
```

<210> SEQ ID NO 29
<211> LENGTH: 18
<212> TYPE: PRT
<213> ORGANISM: Artificial Sequence
<220> FEATURE:
<223> OTHER INFORMATION: peptide

<400> SEQUENCE: 29

Arg Arg Lys Asp Leu His Asp Asp Glu Glu Asp Glu Ala Met Ser Ile
1               5                   10                  15

Thr Ala

<210> SEQ ID NO 30
<211> LENGTH: 15
<212> TYPE: PRT
<213> ORGANISM: Artificial Sequence
<220> FEATURE:
<223> OTHER INFORMATION: peptide

<400> SEQUENCE: 30

Leu Ser Ser Leu Arg Ala Ser Thr Ser Lys Ser Gly Gly Gln Lys
1               5                   10                  15

<210> SEQ ID NO 31
<211> LENGTH: 13
<212> TYPE: PRT
<213> ORGANISM: Artificial Sequence
<220> FEATURE:
<223> OTHER INFORMATION: peptide

<400> SEQUENCE: 31

Lys Lys Arg Pro Gln Arg Ala Thr Ser Asn Val Phe Ser
1               5                   10

<210> SEQ ID NO 32
<211> LENGTH: 18
<212> TYPE: PRT
<213> ORGANISM: Artificial Sequence
<220> FEATURE:
<223> OTHER INFORMATION: peptide

<400> SEQUENCE: 32

Lys Lys Lys Leu Pro Ala Thr Gly Asp Tyr Met Asn Met Ser Pro Val
1               5                   10                  15

Gly Asp

<210> SEQ ID NO 33
<211> LENGTH: 11
<212> TYPE: PRT
<213> ORGANISM: Artificial Sequence
<220> FEATURE:
<223> OTHER INFORMATION: peptide

<400> SEQUENCE: 33

Lys Lys Lys Lys Glu Glu Ile Tyr Phe Phe Phe
1               5                   10

<210> SEQ ID NO 34
<211> LENGTH: 17
<212> TYPE: PRT
<213> ORGANISM: Artificial Sequence
<220> FEATURE:
<223> OTHER INFORMATION: peptide

<400> SEQUENCE: 34

```
Ser Gly Gln Leu Ile Asp Ser Met Ala Asn Ser Phe Val Gly Thr Arg
1               5                   10                  15
Ser

<210> SEQ ID NO 35
<211> LENGTH: 12
<212> TYPE: PRT
<213> ORGANISM: Artificial Sequence
<220> FEATURE:
<223> OTHER INFORMATION: peptide

<400> SEQUENCE: 35

Glu Ala Ile Tyr Ala Ala Pro Phe Ala Lys Lys Lys
1               5                   10

<210> SEQ ID NO 36
<211> LENGTH: 7
<212> TYPE: PRT
<213> ORGANISM: Artificial Sequence
<220> FEATURE:
<223> OTHER INFORMATION: peptide

<400> SEQUENCE: 36

Tyr Ile Tyr Gly Ser Phe Lys
1               5
```

METHODS FOR IDENTIFYING COMPOUNDS THAT ALTER KINASE ACTIVITY

This application claims the priority of provisional application U.S. Ser. No. 60/136,781, filed May 28, 1999, which is incorporated by reference herein.

BACKGROUND OF THE INVENTION

1. Field of the Invention

The invention is directed to purified and isolated novel murine and human kinase polypeptides and fragments thereof, the nucleic acids encoding such polypeptides, processes for production of recombinant forms of such polypeptides, fragmented peptides derived from these polypeptides, antibodies generated against these polypeptides, methods of identifying activators and inhibitors of the activity of these kinases, and therapeutic and diagnostic uses thereof.

2. Background

Cells respond to external signals and internal signals, such as those produced by disease conditions, by activating cellular signaling pathways. Cellular signaling often involves a molecular activation cascade, during which a receptor propagates a ligand-receptor mediated signal by specifically activating intracellular protein kinases which phosphorylate target substrates. These substrates can themselves be kinases which become activated following phosphorylation.

The eukaryotic protein kinases make up a large and rapidly expanding family of proteins related on the basis of homologous catalytic domains. Spurred by the development of gene cloning and sequencing methodologies, distinct protein kinase genes have been identified from a wide selection of invertebrates and lower eukaryotes, including Drosophila, *Caenorhabditis elegans,* Aplysia, Hydra, Dictyostelium, and budding (*Saccharomyces cerevisiae*) and fission (*Schizosaccharomyces pombe*) yeast. Homologous genes have also been identified in higher plants. Protein kinases, however, are not limited to the eukaryotes. Enzyme activities have been well documented in prokaryotes, but the prokaryotic protein kinase genes are not obviously similar to those of the eukaryotes.

Given the important function of kinases in general, there is a need in the art for additional members of the kinase family. In addition, in view of the continuing interest in protein research, the discovery, identification, and roles of new proteins, such as protein kinases, are at the forefront of modem molecular biology and biochemistry. Despite the growing body of knowledge, there is still a need in the art for the identity and function of proteins having kinase activities. In addition, because there is an unmet need for therapeutic compounds which modulate kinase activity and because protein kinases are useful biochemical reagents, there is also need in the art for the continued discovery of unique members of the protein kinase family and potential therapeutic targets thereof.

SUMMARY OF THE INVENTION

The invention aids in fulfilling these various needs in the art by providing isolated murine and human kinase nucleic acids and polypeptides encoded by these nucleic acids. Particular embodiments of the invention are directed to isolated murine and human kinase nucleic acid molecules comprising the DNA sequences of SEQ ID NOs:1–7 and isolated murine and human kinase nucleic acid molecules encoding the amino acid sequences of SEQ ID NOs:8–14, as well as nucleic acid molecules complementary to these sequences. Both single-stranded and double-stranded RNA and DNA nucleic acid molecules are encompassed by the invention, as well as nucleic acid molecules that hybridize to a denatured, double-stranded DNA comprising all or a portion of SEQ ID NOs:1–7. Also encompassed are isolated nucleic acid molecules that are derived by in vitro mutagenesis of nucleic acid molecules comprising sequences of SEQ ID NOs:1–7, that are degenerate from nucleic acid molecules comprising sequences of SEQ ID NOs:1–7, and that are allelic variants of DNA of the invention. The invention also encompasses recombinant vectors that direct the expression of these nucleic acid molecules and host cells stably or transiently transformed or transfected with these vectors.

In addition, the invention encompasses methods of using the nucleic acids noted above to identify nucleic acids encoding proteins having kinase activity and to study cell signal transduction.

The invention also encompasses the use of sense or antisense oligonucleotides from the nucleic acid of SEQ ID NOs:1–7 to inhibit the expression of the polynucleotide encoded by the kinase genes.

The invention also encompasses isolated polypeptides and fragments thereof encoded by these nucleic acid molecules including soluble polypeptide portions of SEQ ID NOs:8–14. The invention further encompasses methods for the production of these polypeptides, including culturing a host cell under conditions promoting expression and recovering the polypeptide from the culture medium. Especially, the expression of these polypeptides in bacteria, yeast, plant, insect, and animal cells is encompassed by the invention.

In general, the polypeptides of the invention can be used to study cellular processes such as signal transduction and to screen for compounds which modulate kinase activity which may have therapeutic potential. In addition, these polypeptides can be used to identify proteins associated with the polypeptides of the invention.

In addition, the invention includes assays utilizing these polypeptides to screen for potential inhibitors of activity associated with polypeptide counter-structure molecules, and methods of using these inhibitors as therapeutic agents for the treatment of cancer and other proliferative diseases and diseases mediated by polypeptide counter-structure molecules. Further, methods of using these polypeptides in the design of inhibitors thereof are also an aspect of the invention.

The invention further provides a method for using these polypeptides as molecular weight markers that allow the estimation of the molecular weight of a protein or a fragmented protein, as well as a method for the visualization of the molecular weight markers of the invention thereof using electrophoresis. The invention further encompasses methods for using the polypeptides of the invention as markers for determining the isoelectric point of an unknown protein, as well as controls for establishing the extent of fragmentation of a protein.

Further encompassed by this invention are kits to aid in these determinations.

Further encompassed by this invention is the use of the kinase nucleic acid sequences, predicted amino acid sequences of the polypeptide or fragments thereof, or a combination of the predicted amino acid sequences of the polypeptide and fragments thereof for use in searching an electronic database to aid in the identification of sample nucleic acids and/or proteins.

Isolated polyclonal or monoclonal antibodies that bind to these polypeptides are also encompassed by the invention, in addition the use of these antibodies to aid in purifying the murine and human kinase polypeptides.

Also encompassed by the invention is a method of designing an inhibitor of the kinase polypeptide of the invention, the method comprising the steps of determining the three-dimensional structure of such polypeptide, analyzing the three-dimensional structure for the likely binding sites of substrates, synthesizing a molecule that incorporates a predicted reactive site, and determining the polypeptide-inhibiting activity of the molecule.

Another aspect of the invention is a method for identifying compounds that activate or inhibit kinase activity comprising:

(a) bringing a test compound into contact with the polypeptide of the invention and a substrate; and (b) determining whether the test compound activates or inhibits the kinase activity of said polypeptide. In a preferred embodiment of this method, the test compound is brought into contact with the polypeptide in a cell containing at least one recombinant vector that directs the expression of at least one polynucleotide encoding said polypeptide.

Another aspect of the invention is a method for inhibiting the kinase activity of the polypeptide of the invention comprising forming a mixture of the polypeptide, a substrate, and a compound, wherein the compound blocks the binding of the polypeptide with the substrate.

BRIEF DESCRIPTION OF THE FIGURES

FIGS. 1–6 each depict an alignment of the amino acid sequence of a kinase of the invention (top line) with the conserved amino acid residues of the family of protein serine/threonine kinases (bottom line). Invariant residues are shown in UPPER CASE letters, nearly-invariant residues as lower case, conserved hydrophobic residues as (o), conserved polar residues as (*), and conserved small residues with near neutral polarity as (+).

FIG. 1 presents the amino acid sequence alignment of the consensus protein serine/threonine kinase sequence with MDCK-1.

FIG. 2 presents the amino acid sequence alignment of the consensus protein serine/threonine kinase sequence with MDCK-2.

FIG. 3 presents the amino acid sequence alignment of the consensus protein serine/threonine kinase sequence with MDCK-3.

FIG. 4 presents the amino acid sequence alignment of the consensus protein serine/threonine kinase sequence with SK-1.

FIG. 5 presents the amino acid sequence alignment of the consensus protein serine/threonine kinase sequence with MLSK-2.

FIG. 6 presents the amino acid sequence alignment of the consensus protein serine/threonine kinase sequence with LNRK-1.

DETAILED DESCRIPTION OF THE INVENTION

The molecules encompassed in the invention include the following nucleotide and amino acid sequences:

| Kinase: | DNA Sequence: | Protein Sequence: |
|---|---|---|
| MDCK-1 | SEQ ID NO:1 | SEQ ID NO:8 |
| MDCK-2 | SEQ ID NO:2 | SEQ ID NO:9 |
| MDCK-3 | SEQ ID NO:3 | SEQ ID NO:10 |
| MLSK-1 | SEQ ID NO:4 | SEQ ID NO:11 |
| MLSK-2 | SEQ ID NO:5 | SEQ ID NO:12 |
| ss4694 | SEQ ID NO:6 | SEQ ID NO:13 |
| LNRK-I | SEQ ID NO:7 | SEQ ID NO:14 |
| LNRK-1 primers | SEQ ID NO:15 and SEQ ID NO:16 | |

The discovery of the nucleic acids of the invention enables the construction of expression vectors comprising nucleic acid sequences encoding polypeptides; host cells transfected or transformed with the expression vectors; isolated and purified biologically active polypeptides and fragments thereof; the use of the nucleic acids or oligonucleotides thereof as probes to identify nucleic acid encoding proteins having kinase activity; the use of single-stranded sense or antisense oligonucleotides from the nucleic acids to inhibit expression of polynucleotides encoded by the kinase genes of the invention; the use of such polypeptides and soluble fragments to function as kinases; the use of such polypeptides and fragmented peptides as molecular weight markers; the use of such polypeptides and fragmented peptides as controls for peptide fragmentation, and kits comprising these reagents; the use of such polypeptides and fragments thereof to generate antibodies; and the use of antibodies to purify the human and murine kinase polypeptides.

Nucleic Acid Molecules

In a particular embodiment, the invention relates to certain isolated nucleotide sequences that are free from contaminating endogenous material. A "nucleotide sequence" refers to a polynucleotide molecule in the form of a separate fragment or as a component of a larger nucleic acid construct. The nucleic acid molecule has been derived from DNA or RNA isolated at least once in substantially pure form and in a quantity or concentration enabling identification, manipulation, and recovery of its component nucleotide sequences by standard biochemical methods (such as those outlined in Sambrook et al., *Molecular Cloning: A Laboratory Manual*, 2nd sed., Cold Spring Harbor Laboratory, Cold Spring Harbor, N.Y. (1989)). Such sequences are preferably provided and/or constructed in the form of an open reading frame uninterrupted by internal non-translated sequences, or introns, that are typically present in eukaryotic genes. Sequences of non-translated DNA can be present 5' or 3' from an open reading frame, where the same do not interfere with manipulation or expression of the coding region.

Nucleic acid molecules of the invention include DNA in both single-stranded and double-stranded form, as well as the RNA complement thereof. DNA includes, for example, cDNA, genomic DNA, chemically synthesized DNA, DNA amplified by PCR, and combinations thereof. Genomic DNA may be isolated by conventional techniques, e.g., using the cDNA of SEQ ID NOs:1–7, or a suitable fragment thereof, as a probe.

The DNA molecules of the invention include full length genes as well as polynucleotides and fragments thereof. Other embodiments include DNA encoding a soluble form of the protein.

The nucleic acids of the invention are preferentially derived from murine and human sources, but the invention includes those derived from other sources, as well.

Preferred Sequences

Particularly preferred nucleotide sequences of the invention are SEQ ID NOs:1–7, as set forth above. The sequences set forth in SEQ ID NOs:1–3 are Murine Dendritic Cell Kinases (MDCK) 1 to 3, respectively. SEQ ID NOs:4–5 are Murine Lymph node Stromal cell Kinases (MLSK) 1 and 2. Finally, SEQ ID NO:6 is from human dendritic cells and is called SS-4694. This sequence was utilized to clone full length SEQ ID NO:7, called Large NIK-Related Kinase (LNRK) 1.

Clones having the nucleotide sequences of SEQ ID NOs:1–7 were isolated as described in Example 1. The sequences of amino acids encoded by the DNAs of SEQ ID NOs:1–7 are shown in SEQ ID NOs:8–14. As set forth in detail below, the amino acid sequences for MDCK-1 (SEQ ID NO:8), MDCK-2 (SEQ ID NO:9), MDCK-3 (SEQ ID NO:10), MLSK-1 (SEQ ID NO:11), MLSK-2 (SEQ ID NO:12), ss4694(SEQ ID NO:13), and LNRK-1 (SEQ ID NO:14) identify the polynucleotides as a member of the kinase superfamily.

Particularly preferred polynucleotides that encode the kinases of the invention and which comprise certain nucleotide sequences of SEQ ID NOs:1–7 are as follows:

nucleotides 71–893 of SEQ ID NO:1 (MDCK-1);

nucleotides 115–1020, 136–1020, and 190–1020 of SEQ ID NO:2 (MDCK-2);

nucleotides 243–1307 of SEQ ID NO:3 (MDCK-3);

nucleotides 123–2015 of SEQ ID NO:4 (MLSK-1);

nucleotides 121–1053 of SEQ ID NO:5 (MLSK-2);

nucleotides 95–892 of SEQ ID NO:6 (ss4694); and nucleotides 1–4080 of SEQ ID NO:7 (LNRK-1).

Additional Sequences

Due to the known degeneracy of the genetic code, wherein more than one codon can encode the same amino acid, a DNA sequence can vary from that shown in SEQ ID NOs:1–7 and still encode a polypeptide having the amino acid sequence of SEQ ID NOs:8–14. Such variant DNA sequences can result from silent mutations (e.g., occurring during PCR amplification), or can be the product of deliberate mutagenesis of a native sequence.

The invention thus provides isolated DNA sequences encoding polypeptides of the invention, selected from: (a) DNAs comprising the nucleotide sequence of SEQ ID NOs:1–7; (b) DNAs encoding the polypeptides of SEQ ID NOs:8–14; (c) DNA capable of hybridization to a DNA of (a) or (b) under conditions of moderate stringency and which encodes polypeptides of the invention; (d) DNA capable of hybridization to a DNA of (a) or (b) under conditions of high stringency and which encodes polypeptides of the invention, and (e) DNA which is degenerate as a result of the genetic code to a DNA defined in (a), (b), (c), or (d) and which encode polypeptides of the invention. Of course, polypeptides encoded by such DNA sequences are encompassed by the invention.

As used herein, conditions of moderate stringency can be readily determined by those having ordinary skill in the art based on, for example, the length of the DNA. The basic conditions are set forth by Sambrook et al. *Molecular Cloning: A Laboratory Manual,* 2 ed. Vol. 1, pp. 1.101–104, Cold Spring Harbor Laboratory Press, (1989), and include use of a prewashing solution for the nitrocellulose filters 5× SSC, 0.5% SDS, 1.0 mM EDTA (pH 8.0), hybridization conditions of about 50% formamide, 6× SSC at about 42° C. (or other similar hybridization solution, such as Stark's solution, in about 50% formamide at about 42° C.), and washing conditions of about 60° C., 0.5× SSC, 0.1% SDS.

Conditions of high stringency can also be readily determined by the skilled artisan based on, for example, the length of the DNA. Generally, such conditions are defined as hybridization conditions as above, and with washing at approximately 68° C., 0.2× SSC, 0.1% SDS. The skilled artisan will recognize that the temperature and wash solution salt concentration can be adjusted as necessary according to factors such as the length of the probe. Preferred hybridizing polynucleotides are those that are at least 25%, more preferably 50%, and most preferably 75% of the length of the polynucleotide to which they hybridize.

Also included as an embodiment of the invention is DNA encoding polypeptide fragments and polypeptides comprising inactivated N-glycosylation site(s), inactivated protease processing site(s), or conservative amino acid substitution (s), as described below.

In another embodiment, the nucleic acid molecules of the invention also comprise nucleotide sequences that are at least 80% identical to a native sequence. Also contemplated are embodiments in which a nucleic acid molecule comprises a sequence that is at least 90% identical, at least 95% identical, at least 98% identical, at least 99% identical, or at least 99.9% identical to a native sequence.

The percent identity may be determined by visual inspection and mathematical calculation. Alternatively, the percent identity of two nucleic acid sequences can be determined by comparing sequence information using the GAP computer program, version 6.0 described by Devereux et al. (*Nucl. Acids Res.* 12:387, 1984) and available from the University of Wisconsin Genetics Computer Group (UWGCG). The preferred default parameters for the GAP program include: (1) a unary comparison matrix (containing a value of 1 for identities and 0 for non-identities) for nucleotides, and the weighted comparison matrix of Gribskov and Burgess, *Nucl. Acids Res.* 14:6745, 1986, as described by Schwartz and Dayhoff, eds., *Atlas of Protein Sequence and Structure,* National Biomedical Research Foundation, pp. 353–358, 1979; (2) a penalty of 3.0 for each gap and an additional 0.10 penalty for each symbol in each gap; and (3) no penalty for end gaps. Other programs used by one skilled in the art of sequence comparison may also be used.

The invention also provides isolated nucleic acids useful in the production of polypeptides. Such polypeptides may be prepared by any of a number of conventional techniques. A DNA sequence encoding a kinase polypeptide of the invention, or desired fragment thereof, may be subcloned into an expression vector for production of the polypeptide or fragment. The DNA sequence advantageously is fused to a sequence encoding a suitable leader or signal peptide. Alternatively, the desired fragment may be chemically synthesized using known techniques. DNA fragments also may be produced by restriction endonuclease digestion of a full length cloned DNA sequence, and isolated by electrophoresis on agarose gels. If necessary, oligonucleotides that reconstruct the 5' or 3' terminus to a desired point may be ligated to a DNA fragment generated by restriction enzyme digestion. Such oligonucleotides may additionally contain a restriction endonuclease cleavage site upstream of the desired coding sequence, and position an initiation codon (ATG) at the N-terminus of the coding sequence.

The well-known polymerase chain reaction (PCR) procedure also may be employed to isolate and amplify a DNA sequence encoding a desired protein fragment. Oligonucleotides that define the desired termini of the DNA fragment are employed as 5' and 3' primers. The oligonucleotides may additionally contain recognition sites for restriction endonucleases, to facilitate insertion of the amplified DNA fragment into an expression vector. PCR techniques are described in Saiki et al., *Science* 239:487 (1988); *Recombinant DNA Methodology,* Wu et al., eds., Academic Press, Inc., San Diego (1989), pp. 189–196; and *PCR Protocols: A Guide to Methods and Applications,* Innis et al., eds., Academic Press, Inc. (1990).

Polypeptides and Fragments Thereof

The invention encompasses polypeptides and fragments thereof in various forms, including those that are naturally occurring or produced through various techniques such as procedures involving recombinant DNA technology. Such forms include, but are not limited to, derivatives, variants, and oligomers, as well as fusion proteins or fragments thereof.

Polypeptides and Fragments Thereof

The polypeptides of the invention include full length proteins encoded by the nucleic acid sequences set forth above. Particularly preferred polypeptides comprise the amino acid sequences of SEQ ID NOs:8–14 as follows:

amino acids 1–275, 25–275, 140–226, and 149–175 of SEQ ID NO:8 (MDCK-1);

amino acids 1–302, 8–302, 26–302, 34–295, 60–229, 157–183, and 198–229 of SEQ ID NO:9 (MDCK-2);

amino acids 1–355, 23–279, 124–221, 134–169, and 183–214 of SEQ ID NO:10 (MDCK-3);

amino acids 1–631, 57–309, 129–254, 175–200, and 215–247 of SEQ ID NO:11 (MLSK-1);

amino acids 1–311, 14–271, 41–213, 124–161, and 175–206 of SEQ ID NO:12 (MLSK-2);

amino acids 1–266, 1–261, 25–258, 101–233, 149–175, and 190–226 of SEQ ID NO:13 (ss4694); and amino acids 1–1360, 25–306, 25–258, 101–233, 149–175, and 190–226 of SEQ ID NO:14 (LNRK-1).

As set forth in FIGS. 1–6, alignments of the polypeptide sequences of the invention (SEQ ID NOs:8–12 and 14) with the conserved residues of the family of protein serine/threonine kinases indicate that the polypeptides of the invention are serine/threonine kinases. The homology studies described below for each of these six sequences provide additional support for their activity as serine/threonine kinases.

MDCK-1

As noted above, three of the cDNAs (MDCK-1, MDCK-2 and MDCK-3) were isolated from murine (*Mus musculus* C57 Black6) dendritic cells. MDCK-1 (SEQ ID NO:1) encodes an open reading frame (nucleotides 71–1009) which commences with an ATG coding for a methionine residue and ends with an in-frame stop codon. In addition, the predicted polypeptide of MDCK-1 (SEQ ID NO:8, 275 amino acids) contains a canonical protein serine/threonine kinase domain from amino acid residues 25 to 296.

In initial searches of public databases using the BLAST algorithm, it was found that MDCK-1 closely resembles the following GenBank entries: Accession #AF096300, HPK/GCK-like kinase (HGK) [Homo sapiens] (85% amino acid identity, 248 out of 291 amino acid residues); Accession #U88984, Nck-interacting kinase (NIK) [Mus musculus] (83% amino acid identity, 243 out of 291 amino acid residues); Accession #AB01123, KIAA0551 protein [Homo sapiens] (85% amino acid identity, 225 out of 264 amino acid residues). A search of the Derwent GeneSeq patent database using the BLAST algorithm revealed: Human protein kinase SOK-1 (Ste20 oxidant stress response kinase protein) which has 46% amino acid identity with MDCK-1 and Human protein kinase HPK, which has 44% amino acid identity with MDCK-1. In the kinase domain, the strongest homology of MDCK-1 was found to be with human HPK/GCK-like kinase HGK (Accession AF096300, 85% amino acid identity) and murine NIK (Accession U88984, 83% amino acid identity) although there are close similarities with a number of other members of a growing subfamily of kinases collectively termed the GC-kinases (for Germinal Center Kinases).

In more recent searches of public databases using BLAST, the following Genbank protein sequences were found to have even greater sequence similarity to the MDCK-1 polypeptide: Accession #AB035697, Misshapen/NIKs-related kinase MINK-1 [Mus musculus] (100% amino acid identity, 275 of 275 residues); Accession #AB041925, GCK family kinase MINK-2 [Mus musculus] (100% amino acid identity, 275 of 275 residues); Accession #AB035698, Misshapen/NIKs-related kinase MINK-1 [Homo sapiens] (99% amino acid identity, 274 of 275 residues); Accession #AB041926, GCK family kinase MINK-2 [Homo sapiens] (99% amino acid identity, 274 of 275 residues). MINK is a novel GCK family kinase that is most abundant in brain. Its expression is up-regulated in the course of the postnatal development of mouse cerebrum. MINK is an upstream activator of the stress-activated protein kinase cascade. MINK-2 is an alternatively spliced form of MINK-1; a splicing cassette consisting of 24 bp encoding a 6 amino acid polypeptide is inserted. MINK-2 is more abundant than MINK-1 in mouse brain. The search of the Derwent GeneSeq patent database using the BLAST algorithm revealed: Accession #Y55931, Human ZC1 protein (91% amino acid identity, 251 of 275 residues); Accession #Y55954, Mouse STE20-related protein kinase NIK protein (89% amino acid identity, 246 of 275 residues); Accession #Y55933, Human ZC3 protein (98% amino acid identity, 236 of 240 residues); Accession #Y55953, Nematode STE20-related protein kinase ZC504.4 protein (82% amino acid identity, 221 of 268 residues; and Accession #Y55932, Human ZC2 protein. protein (90% amino acid identity, 216 of 239 residues).

MDCK-1 is clearly a member of the GCK family which includes the NcK interacting kinase family (NIK). GCK kinases are a subfamily of the Sterile20 (STE-20) protein kinases. This family of kinases are involved as upstream activators of the Jun terminal kinases (JNK's) which are characteristically activated in response to a variety of cellular stresses. The properties of these kinases were recently reviewed [Kyriakis J M, 1999, Signaling by the germinal center kinase family of protein kinases, *J. Biol. Chem.* 274(9): 5259–62; which is incorporated by reference herein]. The sequence of the MDCK-1 polypeptide indicates that it may be a truncated version of murine MINK; however, MDCK-1 protein contains an intact kinase domain and is predicted to form a catalytically functional kinase when expressed in host cells, and therefore can be used to modulate or regulate these pathways in disease conditions, and to identify activators and inhibitors of these pathways.

MDCK-2

The MDCK-2 cDNA was isolated from murine dendritic cells. Nucleotides 115–1020 of MDCK-2 (SEQ ID NO:2) encode an open reading frame with three possible in-frame initiator methionines at amino acid residues 1, 8, and 26. All three of these methionine residues are upstream of the first kinase subdomain. Any one or more of them could be the physiologically relevant initiator Met; however, amino acid sequence similarity to human NEK5 protein suggests that the methionine at the first position is the initiator Met residue. SEQ ID NO:9 shows the open reading frame with a predicted polypeptide of 304 amino acids. Like MDCK-1, MDCK-2 contains a canonical protein serine/threonine kinase domain (amino acid residues 34–295 of SEQ ID NO:9).

In initial searches of the public databases using the BLAST algorithm it was found that MDCK-2 most closely resembles a GenBank entry: Accession #Z50873. MDCK-2 demonstrated 77% amino acid amino acid identity (189 out of 245 residues) to this putative kinase from *Caenorhabditis elegans*. MDCK-2 also appeared related to the NEK (NIMA-related protein kinase) family of kinases. A BLAST search of the Derwent patent database indicated a human kinase called HPK-1 has 85% amino acid amino acid identity with MDCK-2 protein over a 232 amino acid span.

In more recent searches of the public databases using BLAST, the following Genbank protein sequence was found to have sequence similarity to the MDCK-2 polypeptide: Accession #AB026289, protein kinase SID6-1512 [Homo sapiens] (81% amino acid identity, 238 of 291 residues). The search of the Derwent GeneSeq patent database using the BLAST algorithm revealed: Accession #Y59143, Human serine/threonine kinase, NEK5 protein (97% amino acid identity, 295 of 302 residues). MDCK-2 appears to be the murine homologue of human NEK5, and there are several other NEKs that are closely related to MDCK-2. The NEKs were named based on their relationship with the NIMA family (NIMA-related kinase), which are proteins that regulate mitosis and mitogenesis.

MDCK-3

MDCK-3 was isolated from murine dendritic cells and encodes an open reading frame of 355 amino acids (nucleotides 243–1310 of SEQ ID NO:3) which contains a canonical serine/threonine kinase domain (amino acid residues 23–279 of SEQ ID NO:10 and FIG. 3).

Initial searches of available protein sequence databases revealed that MDCK-3 had not previously been described. The closest homolog in these databases was rat calcium/calmodulin-dependent kinase 1 (Genbank accession Q63450) which shares 77.7% sequence amino acid identity with MDCK-3.

In more recent searches of the public databases using BLAST, the following Genbank protein sequences were found to have sequence similarity to the MDCK-3 polypeptide: Accession #AAA66944, CaM-like protein kinase [Rattus norvegicus] (84% amino acid identity, 266 of 314 residues); Accession #AAA99458, cam kinase I [Homo sapiens] (84% amino acid identity, 265 of 314 residues); and Accession #AAA19670, protein kinase I [Rattus norvegicus] (83% amino acid identity, 263 of 314 residues). The search of the Derwent GeneSeq patent database using the BLAST algorithm revealed additional calcium/calmodulin-dependent protein kinases as having similarity to MDCK-3, but none that shared more than 70% amino acid sequence amino acid identity with MDCK-3. From these results it is clear that MDCK-3 is a member of the Ca2+/calmodulin-dependent kinase family.

MDCK-3 RNA has been found to be expressed in certain cancer cell lines, but not in others (see the table below); thus, MDCK-3 may be useful as a marker for the presence certain cancer types, such as colon cancer or ovarian cancer.

| Cancer Cell Line: | Cancer Type: | MDCK-3 Expression: |
| --- | --- | --- |
| Colo205 | colon carcinoma | + |
| HT29 | colon carcinoma | + |
| IGROV-1 | ovarian carcinoma | + |
| MDA231 | breast adenocarcinoma | + |
| Jurkat | T-cell leukemia | – |
| MALME-3M | melanoma | – |
| WM9 | melanoma | – |

-continued

| Cancer Cell Line: | Cancer Type: | MDCK-3 Expression: |
| --- | --- | --- |
| WM-35 | melanoma | – |
| WM164 | melanoma | – |
| WM-3211 | melanoma | + |

MDCK-3 RNA has also been demonstrated to be regulated in response to dendritic cell maturation and/or activation, as described in Example 7.

MLSK-1

Two additional clones, MLSK-1 and MLSK-2, were isolated from murine lymph node stromal cells. MLSK-1 (SEQ ID NO:11) contains an open reading frame encoded by nucleotides 123–2015 of SEQ ID NO:4, which commences with an ATG coding for a methionine residue and ends with an in-frame stop codon. The predicted 631 amino acid sequence (SEQ ID NO:11) contains a canonical protein serine/threonine kinase domain at residues 57 to 309.

In initial searches of public databases using the BLAST algorithm it was found that MLSK-1 most closely resembles (61.5% amino acid identity, 281 of 452 residues) a putative human protein called KIAA0537 (GenBank accession #AB011109), which also appears to encode a protein kinase. MLSK-1 is not likely to simply be the murine homolog of KIAA0537, however, since there is an example of a publicly-available human EST (AI469033) that shares a higher percentage amino acid identity (87%) with MLSK-1 over 477 predicted residues than does KIAA0537. Generally, MLSK-1 most closely resembles a subset of the protein kinase superfamily known as the adenosine monophosphate (AMP) kinases (AMPK's). More recent database searches have not revealed any sequences more similar to MLSK-1.

As described in Example 8, we have expressed an active form of MLSK-1 and shown that when over-expressed in COS cells it activates the MAP kinase signaling pathway as evidenced by the generation of phosphorylated forms of ERK (Extracellularly Regulated Kinase), and therefore is likely involved in a pathway regulating mitogenesis. Overexpression of MLSK-1 had no effect on the stress-activated kinase pathway, as it did not result in activation of either JNK nor p38 kinases.

As described in Example 9, assays to determine whether MLSK-1 could activate the transcription factor AP-1 were performed. AP-1 is a transcription factor known to be involved in the JNK and p38 signaling pathways. MLSK-1 was co-transfected with an AP-1-luciferase construct into COS-7 cells in a standard AP-1-luciferase reporter assay. The overexpression of MLSK-1 did not activate AP-1 using this assay system.

We obtained some preliminary data on MLSK-1 substrate specificity using a PhosphoSpots™ assay, as described in Example 5. This is a membrane which has coupled to it 20 different peptide sequences that are known to have sites recognized by known kinases. MLSK-1 added phosphate residues to a number of peptide substrates recognized by kinases, and in particular those such as protein kinase C, p34 cdc2 kinase, and one of the p42/p44 MAP kinase substrates.

MLSK-2

In MLSK-2, nucleotides 121 to 1053 of SEQ ID NO:5 encode an open reading frame which ends with an in-frame stop codon. The predicted polypeptide of 311 amino acids of SEQ ID NO:12 contains a methionine at position 1 from which translation is presumably initiated. The sequence C-terminal to this methionine contains little more than a canonical protein serine/threonine kinase domain. There are currently no close homologs of MLSK-2 in the protein sequence databases. There are two publicly-available human ESTs (GenBank Accession numbers AA018361 and AI333117) that are highly similar to regions of MLSK-2 (88% identical over 156 predicted residues, and 97% identical over 116 residues, respectively), implying a high degree of sequence conservation of this kinase.

In more recent searches of the public databases using BLAST, the following Genbank protein sequence was found to have sequence similarity to the MLSK-2 polypeptide: Accession #AL117482 hypothetical protein [Homo sapiens] (92% amino acid identity, 205 of 221 residues). The search of the Derwent GeneSeq patent database using the BLAST algorithm revealed: Accession #Y27057, Human protein kinase HKPM-6 (97% amino acid identity, 199 of 205 residues); and Accession #Y23755, Protein involved in eliciting a signal in HH-PTC, human homologue of the Drosophila fused gene (95% amino acid identity, 196 of 206 residues).

As with MLSK-1, we have expressed an active form of MLSK-2 and shown that when over-expressed in COS cells it activates the MAP kinase signaling pathway as evidenced by the generation of phosphorylated forms of ERK. Overexpression of MLSK-2 had no effect on the stress-activated kinase pathway, i.e it did not activate either JNK nor p38 kinases. (See Example 8 below.)

As was done with MLSK-1, assays to determine whether MLSK-2 could activate the transcription factor AP-1 were performed. MLSK-2 was co-transfected with an AP-1-luciferase construct into COS-7 cells in a standard AP-1-luciferase reporter assay. The overexpression of MLSK-2 did not activate AP-1 using this assay system. (See Example 9 below.)

ss4694 and LNRK-1

A protein serine/threonine kinase was isolated from human dendritic cells, beginning with a novel protein serine/threonine kinase called ss4694 (SEQ ID NO:6); the nucleotide sequence of which codes for a methionine followed by an open reading frame of 261 amino acids (SEQ ID NO:13). Included in this open reading frame are conserved motifs found in all protein kinases. The predicted amino acids 27 through 257 of SEQ ID NO:13 are identical to the N-terminal 230 amino acids of an incomplete protein kinase KIAA0551 (GenBank Accession #AB011123). In fact, ss4694 provides the missing 27 amino-acid N-terminal region of KIAA051. This is significant because this N-terminal sequence cannot be found in any public database at this time. By combining the two sequences ss4694 and KIAA0551, a full-length transcript of 4.08 kb can be predicted as shown in SEQ ID NO:7. The translation of this sequence, which we call LNRK-1 (Large NIK-Related Kinase-1), is shown as SEQ ID:14.

By using PCR primers based upon the sequence of ss4694, it was determined by performing an RT-PCR assay (as described in Example 7 below) that the kinase was expressed at relatively high levels in human spleen. 5' and 3' flanking PCR primers (5' primer: ATGGCGAGCGACTC-CCCGGCTCGAA (SEQ ID NO:15); 3' primer: CCAGT-TCATCATGGAATTTCTGTTGAGGG (SEQ ID NO:16)) were then designed based upon the predicted full-length sequence of LNRK-1 and were used to amplify a 4.08 kb cDNA from a Clontech Marathon-ready human spleen cDNA library. Sequencing of this PCR product confirmed its identity with the sequence predicted for LNKR-1.

In initial searches of the public databases, the strongest homology in the kinase domain of LNRK-1 is with murine NIK (GenBank Accession #U88984) and human HPK/GCK-like kinase HGK (GenBank Accession #AF096300). There are also close similarities to a number of other members of a growing family of kinases collectively termed the GC-kinases (Germinal Center Kinases) (Kyrakis, J M, 1999, Signaling by the germinal center kinase family of protein kinases, *J Biol Chem* 274(9): 5259–62). Generally these kinases are implicated as upstream activators of the Jun terminal kinases (JNK's) which are characteristically activated in response to a variety of cellular stresses.

In more recent searches of the public databases using BLAST, the following Genbank protein sequence was found to have sequence similarity to the LNRK-1 polypeptide: Accession #AF172264, Traf2 and NCK interacting kinase, splice variant 1 [Homo sapiens] (100% amino acid identity, 1360 of 1360 residues). The search of the Derwent GeneSeq patent database using the BLAST algorithm revealed: Accession #Y55932, Human ZC2 (92% amino acid identity, 927 of 1002 residues). LNRK-1 is identical to one of the eight splice variants identified for the Traf2 and Nck interacting kinase "TNIK" of GenBank Accession #AF172264. The ZC2 protein of GeneSeq Accession #Y55932 appears to be identical or at least related to another of these "TNIK" splice variants. TNIK is described as a Novel Germinal Center Kinase Family Member That Activates The JNK Pathway and Regulates The Cytoskeleton (Fu et al., 1999, *J. Biol. Chem.* 274 (43): 30729–30737; which is incorporated by reference herein).

We have assayed the tissue-specific expression for LNRK-1 as reported in Example 7, and found roughly equivalent ubiquitous expression of it with slightly higher levels in PBL and slightly lower levels in kidney, skeletal muscle, and small intestine.

Fragments

The invention also provides polypeptides and fragments of the kinase domain of polypeptides of the invention that retain a desired biological activity. Particular embodiments are directed to polypeptide fragments that retain the ability to bind a "binding partner" or native cognates, substrates, or counter-structure molecules. Such a fragment may be a soluble polypeptide. In another embodiment, the polypeptides and fragments advantageously include regions that are conserved in the kinase family.

Also provided herein are polypeptide fragments comprising at least 10, at least 20, or at least 30, contiguous amino acids of the sequence of SEQ ID NOs:8–14. Fragments derived from different domains find use in studies of signal transduction, and in regulating cellular processes associated with transduction of biological signals. Polypeptide fragments also may be employed as immunogens, in generating antibodies.

Variants

Naturally occurring variants as well as derived variants of the polypeptides and fragments are provided herein.

Variants may exhibit amino acid sequences that are at least 80% identical. Also contemplated are embodiments in which a polypeptide or fragment comprises an amino acid sequence that is at least 90% identical, at least 95% identical, at least 98% identical, at least 99% identical, or at least 99.9% identical to the preferred polypeptide or fragment thereof. Percent identity may be determined by visual inspection and mathematical calculation. Alternatively, the percent identity of two protein sequences can be determined by comparing sequence information using the GAP computer program, based on the algorithm of Needleman and Wunsch (J. Mol. Bio. 48:443, 1970) and available from the University of Wisconsin Genetics Computer Group (UWGCG). The preferred default parameters for the GAP program include: (1) a scoring matrix, blosum62, as described by Henikoff and Henikoff (Proc. Natl. Acad. Sci. USA 89:10915, 1992); (2) a gap weight of 12; (3) a gap length weight of 4; and (4) no penalty for end gaps. Other programs used by one skilled in the art of sequence comparison may also be used.

The variants of the invention include, for example, those that result from alternate mRNA splicing events or from proteolytic cleavage. Alternate splicing of mRNA may, for example, yield a truncated but biologically active protein, such as a naturally occurring soluble form of the protein. Variations attributable to proteolysis include, for example, differences in the N- or C-termini upon expression in different types of host cells, due to proteolytic removal of one or more terminal amino acids from the protein (generally from 1–5 terminal amino acids). Proteins in which differences in amino acid sequence are attributable to genetic polymorphism (allelic variation among individuals producing the protein) are also contemplated herein.

Additional variants within the scope of the invention include polypeptides that may be modified to create derivatives thereof by forming covalent or aggregative conjugates with other chemical moieties, such as glycosyl groups, lipids, phosphate, acetyl groups and the like. Covalent derivatives may be prepared by linking the chemical moieties to functional groups on amino acid side chains or at the N-terminus or C-terminus of a polypeptide. Conjugates comprising diagnostic (detectable) or therapeutic agents attached thereto are contemplated herein, as discussed in more detail below.

Other derivatives include covalent or aggregative conjugates of the polypeptides with other proteins or polypeptides, such as by synthesis in recombinant culture as N-terminal or C-terminal fusions. Examples of fusion proteins are discussed below in connection with oligomers. Further, fusion proteins can comprise peptides added to facilitate purification and identification. Such peptides include, for example, poly-His or the antigenic identification peptides described in U.S. Pat. No. 5,011,912 and in Hopp et al., *Bio/Technology* 6:1204, 1988. One such peptide is the FLAG® peptide which is highly antigenic and provides an epitope reversibly bound by a specific monoclonal antibody, enabling rapid assay and facile purification of expressed recombinant protein. A murine hybridoma designated 4E11 produces a monoclonal antibody that binds the FLAG® peptide in the presence of certain divalent metal cations, as described in U.S. Pat. No. 5,011,912, hereby incorporated by reference. The 4E11 hybridoma cell line has been deposited with the American Type Culture Collection under accession no. HB 9259. Monoclonal antibodies that bind the FLAG® peptide are available from Eastman Kodak Co., Scientific Imaging Systems Division, New Haven, Conn.

Among the variant polypeptides provided herein are variants of native polypeptides that retain the native biological activity or the substantial equivalent thereof. One example is a variant that binds with essentially the same binding affinity as does the native form. Binding affinity can be measured by conventional procedures, e.g., as described in U.S. Pat. No. 5,512,457 and as set forth below.

Variants include polypeptides that are substantially homologous to the native form, but which have an amino acid sequence different from that of the native form because of one or more deletions, insertions or substitutions. Particular embodiments include, but are not limited to, polypeptides that comprise from one to ten deletions, insertions or substitutions of amino acid residues, when compared to a native sequence.

A given amino acid may be replaced, for example, by a residue having similar physiochemical characteristics. Examples of such conservative substitutions include substitution of one aliphatic residue for another, such as Ile, Val, Leu, or Ala for one another; substitutions of one polar residue for another, such as between Lys and Arg, Glu and Asp, or Gln and Asn; or substitutions of one aromatic residue for another, such as Phe, Trp, or Tyr for one another. Other conservative substitutions, e.g., involving substitutions of entire regions having similar hydrophobicity characteristics, are well known.

Similarly, the DNAs of the invention include variants that differ from a native DNA sequence because of one or more deletions, insertions or substitutions, but that encode a biologically active polypeptide.

The invention further includes polypeptides of the invention with or without associated native-pattern glycosylation. Polypeptides expressed in yeast or mammalian expression systems (e.g., COS-1 or COS-7 cells) can be similar to or significantly different from a native polypeptide in molecular weight and glycosylation pattern, depending upon the choice of expression system. Expression of polypeptides of the invention in bacterial expression systems, such as *E. coli*, provides non-glycosylated molecules. Further, a given preparation may include multiple differentially glycosylated species of the protein. Glycosyl groups can be removed through conventional methods, in particular those utilizing glycopeptidase. In general, glycosylated polypeptides of the invention can be incubated with a molar excess of glycopeptidase (Boehringer Mannheim).

Correspondingly, similar DNA constructs that encode various additions or substitutions of amino acid residues or sequences, or deletions of terminal or internal residues or sequences are encompassed by the invention. For example, N-glycosylation sites in the polypeptide extracellular domain can be modified to preclude glycosylation, allowing expression of a reduced carbohydrate analog in mammalian and yeast expression systems. N-glycosylation sites in eukaryotic polypeptides are characterized by an amino acid triplet Asn-X-Y, wherein X is any amino acid except Pro and Y is Ser or Thr. Appropriate substitutions, additions, or deletions to the nucleotide sequence encoding these triplets will result in prevention of attachment of carbohydrate residues at the Asn side chain. Alteration of a single nucleotide, chosen so that Asn is replaced by a different amino acid, for example, is sufficient to inactivate an N-glycosylation site. Alternatively, the Ser or Thr can by replaced with another amino acid, such as Ala. Known procedures for inactivating N-glycosylation sites in proteins include those described in U.S. Pat. No. 5,071,972 and EP 276,846, hereby incorporated by reference.

In another example of variants, sequences encoding Cys residues that are not essential for biological activity can be altered to cause the Cys residues to be deleted or replaced with other amino acids, preventing formation of incorrect intramolecular disulfide bridges upon folding or renaturation.

Other variants are prepared by modification of adjacent dibasic amino acid residues, to enhance expression in yeast systems in which KEX2 protease activity is present. EP 212,914 discloses the use of site-specific mutagenesis to inactivate KEX2 protease processing sites in a protein. KEX2 protease processing sites are inactivated by deleting, adding or substituting residues to alter Arg-Arg, Arg-Lys, and Lys-Arg pairs to eliminate the occurrence of these adjacent basic residues. Lys-Lys pairings are considerably less susceptible to KEX2 cleavage, and conversion of Arg- Lys or Lys-Arg to Lys-Lys represents a conservative and preferred approach to inactivating KEX2 sites.

Production of Polypeptides and Fragments Thereof

Expression, isolation and purification of the polypeptides and fragments of the invention may be accomplished by any suitable technique, including but not limited to the following:

Expression Systems

The present invention provides recombinant cloning and expression vectors containing DNA, as well as host cell containing the recombinant vectors. Expression vectors comprising DNA may be used to prepare the polypeptides or fragments of the invention encoded by the DNA. A method for producing polypeptides comprises culturing host cells transformed with a recombinant expression vector encoding the polypeptide, under conditions that promote expression of the polypeptide, then recovering the expressed polypeptides from the culture. The skilled artisan will recognize that the procedure for purifying the expressed polypeptides will vary according to such factors as the type of host cells employed, and whether the polypeptide is membrane-bound or a soluble form that is secreted from the host cell.

Any suitable expression system may be employed. The vectors include a DNA encoding a polypeptide or fragment of the invention, operably linked to suitable transcriptional or translational regulatory nucleotide sequences, such as those derived from a mammalian, microbial, viral, or insect gene. Examples of regulatory sequences include transcriptional promoters, operators, or enhancers, an mRNA ribosomal binding site, and appropriate sequences which control transcription and translation initiation and termination. Nucleotide sequences are operably linked when the regulatory sequence functionally relates to the DNA sequence. Thus, a promoter nucleotide sequence is operably linked to a DNA sequence if the promoter nucleotide sequence controls the transcription of the DNA sequence. An origin of replication that confers the ability to replicate in the desired host cells, and a selection gene by which transformants are identified, are generally incorporated into the expression vector.

In addition, a sequence encoding an appropriate signal peptide (native or heterologous) can be incorporated into expression vectors. A DNA sequence for a signal peptide (secretory leader) may be fused in frame to the nucleic acid sequence of the invention so that the DNA is initially transcribed, and the mRNA translated, into a fusion protein comprising the signal peptide. A signal peptide that is functional in the intended host cells promotes extracellular secretion of the polypeptide. The signal peptide is cleaved from the polypeptide upon secretion of polypeptide from the cell.

The skilled artisan will also recognize that the position(s) at which the signal peptide is cleaved may differ from that predicted by computer program, and may vary according to such factors as the type of host cells employed in expressing a recombinant polypeptide. A protein preparation may include a mixture of protein molecules having different N-terminal amino acids, resulting from cleavage of the signal peptide at more than one site.

Suitable host cells for expression of polypeptides include prokaryotes, yeast or higher eukaryotic cells. Mammalian or insect cells are generally preferred for use as host cells. Appropriate cloning and expression vectors for use with bacterial, fungal, yeast, and mammalian cellular hosts are described, for example, in Pouwels et al. *Cloning Vectors: A Laboratory Manual,* Elsevier, N.Y., (1985). Cell-free translation systems could also be employed to produce polypeptides using RNAs derived from DNA constructs disclosed herein.

Prokaryotic Systems

Prokaryotes include gram-negative or gram-positive organisms. Suitable prokaryotic host cells for transformation include, for example, *E. coli, Bacillus subtilis, Salmonella typhimurium,* and various other species within the genera Pseudomonas, Streptomyces, and Staphylococcus. In a prokaryotic host cell, such as *E. coli,* a polypeptide may include an N-terminal methionine residue to facilitate expression of the recombinant polypeptide in the prokaryotic host cell. The N-terminal Met may be cleaved from the expressed recombinant polypeptide.

Expression vectors for use in prokaryotic host cells generally comprise one or more phenotypic selectable marker genes. A phenotypic selectable marker gene is, for example, a gene encoding a protein that confers antibiotic resistance or that supplies an autotrophic requirement. Examples of useful expression vectors for prokaryotic host cells include those derived from commercially available plasmids such as the cloning vector pBR322 (ATCC 37017). pBR322 contains genes for ampicillin and tetracycline resistance and thus provides simple means for identifying transformed cells. An appropriate promoter and a DNA sequence are inserted into the pBR322 vector. Other commercially available vectors include, for example, pKK223-3 (Pharmacia Fine Chemicals, Uppsala, Sweden) and pGEM1 (Promega Biotec, Madison, Wis., USA).

Promoter sequences commonly used for recombinant prokaryotic host cell expression vectors include β-lactamase (penicillinase), lactose promoter system (Chang et al., *Nature* 275:615, 1978; and Goeddel et al., *Nature* 281:544, 1979), tryptophan (trp) promoter system (Goeddel et al., *Nucl. Acids Res.* 8:4057, 1980; and EP-A-36776) and tac promoter (Maniatis, *Molecular Cloning: A Laboratory Manual,* Cold Spring Harbor Laboratory, p. 412, 1982). A particularly useful prokaryotic host cell expression system employs a phage $\lambda P_L$ promoter and a cI857ts thermolabile repressor sequence. Plasmid vectors available from the American Type Culture Collection which incorporate derivatives of the $\lambda P_L$ promoter include plasmid pHUB2 (resident in *E. coli* strain JMB9, ATCC 37092) and pPLc28 (resident in *E. coli* RR1, ATCC 53082).

Yeast Systems

Alternatively, the polypeptides may be expressed in yeast host cells, preferably from the Saccharomyces genus (e.g., *S. cerevisiae*). Other genera of yeast, such as Pichia or Kluyveromyces, may also be employed. Yeast vectors will often contain an origin of replication sequence from a 2μ yeast plasmid, an autonomously replicating sequence (ARS), a promoter region, sequences for polyadenylation, sequences for transcription termination, and a selectable marker gene. Suitable promoter sequences for yeast vectors include, among others, promoters for metallothionein, 3-phosphoglycerate kinase (Hitzeman et al., *J. Biol. Chem.* 255:2073, 1980) or other glycolytic enzymes (Hess et al., *J. Adv. Enzyme Reg.* 7:149, 1968; and Holland et al., *Biochem.* 17:4900, 1978), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phospho-glucose isomerase, and glucokinase. Other suitable vectors and promoters for use in yeast expression are further described in Hitzeman, EPA-73,657. Another alternative is the glucose-repressible ADH2 promoter described by Russell et al. (*J. Biol. Chem.* 258:2674, 1982) and Beier et al. (*Nature* 300:724, 1982). Shuttle vectors replicable in both yeast and *E. coli* may be constructed by inserting DNA sequences from pBR322 for selection and replication in *E. coli* (Amp$^r$ gene and origin of replication) into the above-described yeast vectors.

The yeast α-factor leader sequence may be employed to direct secretion of the polypeptide. The α-factor leader sequence is often inserted between the promoter sequence and the structural gene sequence. See, e.g., Kurjan et al., *Cell* 30:933, 1982 and Bitter et al., *Proc. Natl. Acad. Sci. USA* 81:5330, 1984. Other leader sequences suitable for facilitating secretion of recombinant polypeptides from yeast hosts are known to those of skill in the art. A leader sequence may be modified near its 3' end to contain one or more restriction sites. This will facilitate fusion of the leader sequence to the structural gene.

Yeast transformation protocols are known to those of skill in the art. One such protocol is described by Hinnen et al., *Proc. Natl. Acad. Sci. USA* 75:1929, 1978. The Hinnen et al. protocol selects for Trp$^+$ transformants in a selective medium, wherein the selective medium consists of 0.67% yeast nitrogen base, 0.5% casamino acids, 2% glucose, 10 mg/ml adenine and 20 mg/ml uracil.

Yeast host cells transformed by vectors containing an ADH2 promoter sequence may be grown for inducing expression in a "rich" medium. An example of a rich medium is one consisting of 1% yeast extract, 2% peptone, and 1% glucose supplemented with 80 mg/ml adenine and 80 mg/ml uracil. Derepression of the ADH2 promoter occurs when glucose is exhausted from the medium.

Mammalian or Insect Systems

Mammalian or insect host cell culture systems also may be employed to express recombinant polypeptides. Bacculovirus systems for production of heterologous proteins in insect cells are reviewed by Luckow and Summers, *Bio/Technology* 6:47 (1988). Established cell lines of mammalian origin also may be employed. Examples of suitable mammalian host cell lines include the COS-7 line of monkey kidney cells (ATCC CRL 1651) (Gluzman et al., *Cell* 23:175, 1981), L cells, C127 cells, 3T3 cells (ATCC CCL 163), Chinese hamster ovary (CHO) cells, HeLa cells, and BHK (ATCC CRL 10) cell lines, and the CV1/EBNA cell line derived from the African green monkey kidney cell line CV1 (ATCC CCL 70) as described by McMahan et al. (*EMBO J.* 10: 2821, 1991).

Established methods for introducing DNA into mammalian cells have been described (Kaufman, R. J., *Large Scale Mammalian Cell Culture,* 1990, pp. 15–69). Additional protocols using commercially available reagents, such as Lipofectamine lipid reagent (Gibco/BRL) or Lipofectamine-Plus lipid reagent, can be used to transfect cells (Felgner et al., *Proc. Natl. Acad. Sci. USA* 84:7413–7417, 1987). In addition, electroporation can be used to transfect mammalian cells using conventional procedures, such as those in Sambrook et al. (*Molecular Cloning: A Laboratory Manual,* 2 ed. Vol. 1–3, Cold Spring Harbor Laboratory Press, 1989). Selection of stable transformants can be performed using methods known in the art, such as, for example, resistance to cytotoxic drugs. Kaufman et al., *Meth. in Enzymology* 185:487–511, 1990, describes several selection schemes, such as dihydrofolate reductase (DHFR) resistance. A suitable host strain for DHFR selection can be CHO strain DX-B11, which is deficient in DHFR (Urlaub and Chasin, *Proc. Natl. Acad. Sci. USA* 77:4216–4220, 1980). A plasmid expressing the DHFR cDNA can be introduced into strain DX-B11, and only cells that contain the plasmid can grow in the appropriate selective media. Other examples of selectable markers that can be incorporated into an expression vector include cDNAs conferring resistance to antibiotics, such as G418 and hygromycin B. Cells harboring the vector can be selected on the basis of resistance to these compounds.

Transcriptional and translational control sequences for mammalian host cell expression vectors can be excised from viral genomes. Commonly used promoter sequences and enhancer sequences are derived from polyoma virus, adenovirus 2, simian virus 40 (SV40), and human cytomegalovirus. DNA sequences derived from the SV40 viral genome, for example, SV40 origin, early and late promoter, enhancer, splice, and polyadenylation sites can be used to provide other genetic elements for expression of a structural gene sequence in a mammalian host cell. Viral early and late promoters are particularly useful because both are easily obtained from a viral genome as a fragment, which can also contain a viral origin of replication (Fiers et al., *Nature* 273:113, 1978; Kaufman, *Meth. in Enzymology,* 1990). Smaller or larger SV40 fragments can also be used, provided the approximately 250 bp sequence extending from the Hind III site toward the Bgl I site located in the SV40 viral origin of replication site is included.

Additional control sequences shown to improve expression of heterologous genes from mammalian expression vectors include such elements as the expression augmenting sequence element (EASE) derived from CHO cells (Morris et al., *Animal Cell Technology,* 1997, pp. 529–534 and PCT Application WO 97/25420) and the tripartite leader (TPL) and VA gene RNAs from Adenovirus 2 (Gingeras et al., *J. Biol. Chem.* 257:13475–13491, 1982). The internal ribosome entry site (IRES) sequences of viral origin allows dicistronic mRNAs to be translated efficiently (Oh and Sarnow, *Current Opinion in Genetics and Development* 3:295–300, 1993; Ramesh et al., *Nucleic Acids Research* 24:2697–2700, 1996). Expression of a heterologous cDNA as part of a dicistronic mRNA followed by the gene for a selectable marker (e.g. DHFR) has been shown to improve transfectability of the host and expression of the heterologous cDNA (Kaufman, *Meth. in Enzymology,* 1990). Exemplary expression vectors that employ dicistronic mRNAs are pTR-DC/GFP described by Mosser et al., *Biotechniques* 22:150–161, 1997, and p2A5I described by Morris et al., *Animal Cell Technology,* 1997, pp. 529–534.

A useful high expression vector, pCAVNOT, has been described by Mosley et al., *Cell* 59:335–348, 1989. Other expression vectors for use in mammalian host cells can be constructed as disclosed by Okayama and Berg (*Mol. Cell. Biol.* 3:280, 1983). A useful system for stable high level expression of mammalian cDNAs in C127 murine mammary epithelial cells can be constructed substantially as described by Cosman et al. (*Mol. Immunol.* 23:935, 1986). A useful high expression vector, PMLSV N1/N4, described by Cosman et al., *Nature* 312:768, 1984, has been deposited as ATCC 39890. Additional useful mammalian expression vectors are described in EP-A-0367566, and in WO 91/18982, incorporated by reference herein. In yet another alternative, the vectors can be derived from retroviruses.

Additional useful expression vectors, pFLAG® and pDC311, can also be used. FLAG® technology is centered on the fusion of a low molecular weight (1 kD), hydrophilic, FLAG® marker peptide to the N-terminus of a recombinant protein expressed by pFLAG® expression vectors. pDC311 is another specialized vector used for expressing proteins in CHO cells. pDC311 is characterized by a bicistronic sequence containing the gene of interest and a dihydrofolate reductase (DHFR) gene with an internal ribosome binding site for DHFR translation, an expression augmenting sequence element (EASE), the human CMV promoter, a tripartite leader sequence, and a polyadenylation site.

Regarding signal peptides that may be employed, the native signal peptide may be replaced by a heterologous signal peptide or leader sequence, if desired. The choice of signal peptide or leader may depend on factors such as the type of host cells in which the recombinant polypeptide is to be produced. To illustrate, examples of heterologous signal peptides that are functional in mammalian host cells include the signal sequence for interleukin-7 (IL-7) described in U.S. Pat. 4,965,195; the signal sequence for interleukin-2 receptor described in Cosman et al., Nature 312:768 (1984); the interleukin-4 receptor signal peptide described in EP 367,566; the type I interleukin-1 receptor signal peptide described in U.S. Pat. No. 4,968,607; and the type II interleukin-1 receptor signal peptide described in EP 460, 846.

Purification

The invention also includes methods of isolating and purifying the polypeptides and fragments thereof.

Isolation and Purification

The "isolated" polypeptides or fragments thereof encompassed by this invention are polypeptides or fragments that are not in an environment identical to an environment in which it or they can be found in nature. The "purified" polypeptides or fragments thereof encompassed by this invention are essentially free of association with other proteins or polypeptides, for example, as a purification product of recombinant expression systems such as those described above or as a purified product from a non-recombinant source such as naturally occurring cells and/or tissues.

In one preferred embodiment, the purification of recombinant polypeptides or fragments can be accomplished using fusions of polypeptides or fragments of the invention to another polypeptide to aid in the purification of polypeptides or fragments of the invention. Such fusion partners can include the poly-His or other antigenic identification peptides described above as well as the Fc moieties described previously.

With respect to any type of host cell, as is known to the skilled artisan, procedures for purifying a recombinant polypeptide or fragment will vary according to such factors as the type of host cells employed and whether or not the recombinant polypeptide or fragment is secreted into the culture medium.

In general, the recombinant polypeptide or fragment can be isolated from the host cells if not secreted, or from the medium or supernatant if soluble and secreted, followed by one or more concentration, salting-out, ion exchange, hydrophobic interaction, affinity purification or size exclusion chromatography steps. As to specific ways to accomplish these steps, the culture medium first can be concentrated using a commercially available protein concentration filter, for example, an Amicon or Millipore Pellicon ultrafiltration unit. Following the concentration step, the concentrate can be applied to a purification matrix such as a gel filtration medium. Alternatively, an anion exchange resin can be employed, for example, a matrix or substrate having pendant diethylaminoethyl (DEAE) groups. The matrices can be acrylamide, agarose, dextran, cellulose or other types commonly employed in protein purification. Alternatively, a cation exchange step can be employed. Suitable cation exchangers include various insoluble matrices comprising sulfopropyl or carboxymethyl groups. In addition, a chromatofocusing step can be employed. Alternatively, a hydrophobic interaction chromatography step can be employed. Suitable matrices can be phenyl or octyl moieties bound to resins. In addition, affinity chromatography with a matrix which selectively binds the recombinant protein can be employed. Examples of such resins employed are lectin columns, dye columns, and metal-chelating columns. Finally, one or more reversed-phase high performance liquid chromatography (RP-HPLC) steps employing hydrophobic RP-HPLC media, (e.g., silica gel or polymer resin having pendant methyl, octyl, octyldecyl or other aliphatic groups) can be employed to further purify the polypeptides. Some or all of the foregoing purification steps, in various combinations, are well known and can be employed to provide an isolated and purified recombinant protein.

It is also possible to utilize an affinity column comprising a polypeptide-binding protein of the invention, such as a monoclonal antibody generated against polypeptides of the invention, to affinity-purify expressed polypeptides. These polypeptides can be removed from an affinity column using conventional techniques, e.g., in a high salt elution buffer and then dialyzed into a lower salt buffer for use or by changing pH or other components depending on the affinity matrix utilized, or be competitively removed using the naturally occurring substrate of the affinity moiety, such as a polypeptide derived from the invention.

In this aspect of the invention, polypeptide-binding proteins, such as the anti-polypeptide antibodies of the invention or other proteins that may interact with the polypeptide of the invention, can be bound to a solid phase support such as a column chromatography matrix or a similar substrate suitable for identifying, separating, or purifying cells that express polypeptides of the invention on their surface. Adherence of polypeptide-binding proteins of the invention to a solid phase contacting surface can be accomplished by any means, for example, magnetic microspheres can be coated with these polypeptide-binding proteins and held in the incubation vessel through a magnetic field. Suspensions of cell mixtures are contacted with the solid phase that has such polypeptide-binding proteins thereon. Cells having polypeptides of the invention on their surface bind to the fixed polypeptide-binding protein and unbound cells then are washed away. This affinity-binding method is useful for purifying, screening, or separating such polypeptide-expressing cells from solution. Methods of releasing positively selected cells from the solid phase are known in the art and encompass, for example, the use of enzymes. Such enzymes are preferably non-toxic and non-injurious to the cells and are preferably directed to cleaving the cell-surface binding partner.

Alternatively, mixtures of cells suspected of containing polypeptide-expressing cells of the invention first can be incubated with a biotinylated polypeptide-binding protein of the invention. Incubation periods are typically at least one hour in duration to ensure sufficient binding to polypeptides of the invention. The resulting mixture then is passed through a column packed with avidin-coated beads, whereby the high affinity of biotin for avidin provides the binding of the polypeptide-binding cells to the beads. Use of avidin-coated beads is known in the art. See Berenson, et al. *J. Cell. Biochem.*, 10D:239 (1986). Wash of unbound material and the release of the bound cells is performed using conventional methods.

The desired degree of purity depends on the intended use of the protein. A relatively high degree of purity is desired when the polypeptide is to be administered in vivo, for example. In such a case, the polypeptides are purified such that no protein bands corresponding to other proteins are detectable upon analysis by SDS-polyacrylamide gel electrophoresis (SDS-PAGE). It will be recognized by one skilled in the pertinent field that multiple bands corresponding to the polypeptide may be visualized by SDS-PAGE, due to differential glycosylation, differential post-translational processing, and the like. Most preferably, the polypeptide of the invention is purified to substantial homogeneity, as indicated by a single protein band upon analysis by SDS-PAGE. The protein band may be visualized by silver staining, Coomassie blue staining, or (if the protein is radiolabeled) by autoradiography.

Use of Nucleic Acid or Oligonucleotides of the Invention

In addition to being used to express polypeptides as described above, the nucleic acids of the invention, including DNA, RNA, mRNA and oligonucleotides thereof can be used as probes to study signal transduction and to identify nucleic acid encoding proteins having kinase activity; as diagnostic disease markers; and as single-stranded sense or antisense oligonucleotides to inhibit expression of polypeptide encoded by the genes of the invention.

Probes

Among the uses of nucleic acids of the invention is the use of fragments as probes or primers. Such fragments generally comprise at least about 17 contiguous nucleotides of a DNA sequence. In other embodiments, a DNA fragment comprises at least 30, or at least 60, contiguous nucleotides of a DNA sequence.

Because homologs of SEQ ID NOs:1–7 from other mammalian species are contemplated herein, probes based on the DNA sequence of SEQ ID NOs:1–7 may be used to screen cDNA libraries derived from other mammalian species, using conventional cross-species hybridization techniques.

Using knowledge of the genetic code in combination with the amino acid sequences set forth above, sets of degenerate oligonucleotides can be prepared. Such oligonucleotides are useful as primers, e.g., in polymerase chain reactions (PCR), whereby DNA fragments are isolated and amplified.

Chromosome Mapping

All or a portion of the nucleic acids of SEQ ID NO:1–7, including oligonucleotides, can be used by those skilled in the art using well-known techniques to identify the human chromosome, and the specific locus thereof. Useful techniques include, but are not limited to, using the sequence or portions, including oligonucleotides, as a probe in various well-known techniques such as radiation hybrid mapping (high resolution), in situ hybridization to chromosome spreads (moderate resolution), and Southern blot hybridization to hybrid cell lines containing individual human chromosomes (low resolution).

For example, chromosomes can be mapped by radiation hybridization. First, PCR is performed using the Whitehead Institute/MYI Center for Genome Research Genebridge4 panel of 93 radiation hybrids (www-genome.wi.mit.edu/ftp/distribution/human_STS_releases/july97/rhmap/genebridge4.html). Primers are used which lie within a putative exon of the gene of interest and which amplify a product from human genomic DNA, but do not amplify hamster genomic DNA. The results of the PCRs are converted into a data vector that is submitted to the Whitehead/MIT Radiation Mapping site on the internet (http://www-seq.wi.mit.edu). The data is scored and the chromosomal assignment and placement relative to known Sequence Tag Site (STS) markers on the radiation hybrid map is provided. The following web site provides additional information about radiation hybrid mapping: http://www-genome.wi.mit.edu/ftp/distribution/human_STS_releases/july97/07-97.INTRO.html).

Sense-Antisense

Other useful fragments of the nucleic acids include antisense or sense oligonucleotides comprising a single-stranded nucleic acid sequence (either RNA or DNA) capable of binding to target mRNA (sense) or DNA (antisense) sequences. Antisense or sense oligonucleotides, according to the present invention, comprise a fragment of DNA (SEQ ID NOs:1–7). Such a fragment generally comprises at least about 14 nucleotides, preferably from about 14 to about 30 nucleotides. The ability to derive an antisense or a sense oligonucleotide, based upon a cDNA sequence encoding a given protein is described in, for example, Stein and Cohen (*Cancer Res.* 48:2659, 1988) and van der Krol et al. (*BioTechniques* 6:958, 1988).

Binding of antisense or sense oligonucleotides to target nucleic acid sequences results in the formation of duplexes that block or inhibit protein expression by one of several means, including enhanced degradation of the mRNA by RNAseH, inhibition of splicing, premature termination of transcription or translation, or by other means. The antisense oligonucleotides thus may be used to block expression of proteins. Antisense or sense oligonucleotides further comprise oligonucleotides having modified sugar-phosphodiester backbones (or other sugar linkages, such as those described in WO91/06629) and wherein such sugar linkages are resistant to endogenous nucleases. Such oligonucleotides with resistant sugar linkages are stable in vivo (i.e., capable of resisting enzymatic degradation) but retain sequence specificity to be able to bind to target nucleotide sequences.

Other examples of sense or antisense oligonucleotides include those oligonucleotides which are covalently linked to organic moieties, such as those described in WO 90/10448, and other moieties that increases affinity of the oligonucleotide for a target nucleic acid sequence, such as poly-(L-lysine). Further still, intercalating agents, such as ellipticine, and alkylating agents or metal complexes may be attached to sense or antisense oligonucleotides to modify binding specificities of the antisense or sense oligonucleotide for the target nucleotide sequence.

Antisense or sense oligonucleotides may be introduced into a cell containing the target nucleic acid sequence by any gene transfer method, including, for example, lipofection, $CaPO_4$-mediated DNA transfection, electroporation, or by using gene transfer vectors such as Epstein-Barr virus.

Sense or antisense oligonucleotides also may be introduced into a cell containing the target nucleotide sequence by formation of a conjugate with a ligand binding molecule, as described in WO 91/04753. Suitable ligand binding molecules include, but are not limited to, cell surface receptors, growth factors, other cytokines, or other ligands that bind to cell surface receptors. Preferably, conjugation of the ligand binding molecule does not substantially interfere with the ability of the ligand binding molecule to bind to its corresponding molecule or receptor, or block entry of the sense or antisense oligonucleotide or its conjugated version into the cell.

Alternatively, a sense or an antisense oligonucleotide may be introduced into a cell containing the target nucleic acid sequence by formation of an oligonucleotide-lipid complex, as described in WO 90/10448. The sense or antisense oligonucleotide-lipid complex is preferably dissociated within the cell by an endogenous lipase.

Use of Kinase Polypeptides and Fragmented Polypeptides

Uses include, but are not limited to, the following:

Identifying molecules that modulate kinase activity and cellular responses

Purifying proteins and measuring activity thereof

Research Reagents

Molecular weight and Isoelectric focusing markers

Controls for peptide fragmentation

Identification of unknown proteins

Preparation of Antibodies

Therapeutic Compounds

Identifying molecules that modulate kinase activity and cellular responses

Cellular signaling often involves a molecular activation cascade, during which a receptor propagates a ligand-receptor mediated signal by specifically activating intracellular kinases which phosphorylate target substrates. These substrates can themselves be kinases which become activated following phosphorylation. Alternatively, they can be adaptor molecules that facilitate down stream signaling through protein-protein interaction following phosphorylation. Regardless of the nature of the substrate molecule(s), expressed functionally active versions of the polypeptides of the invention, for example the kinase domain, can be used in assays to identify molecules that modulate the recognition and activation of substrate(s) by the kinases. These assays include, without limitation, the yeast 1,- 2-, or 3-hybrid assays, or an assay of binding that measures changes in the surface plasmon resonance of a bound molecule (using for example an instrument from BIAcore), or other assays designed for high-throughput screening. Other assays that may be used to identify activators and inhibitors of the kinases of the invention are described without limitation in the Examples below. In this way, these novel kinases can be used in assay methods to identify novel molecules that can modulate the activity of signal transduction pathways and affect the cellular response to external and internal signals.

The purpose of such an assay is to identify substances which modulate substrate phosphorylation. Such inhibitory or activating substances could serve as lead compounds in the development of pharmaceuticals for the treatment of, for example, autoimmune disease, rheumatoid and other inflammatory conditions, cancer, viral infections, asthma, transplant rejection, infectious or neoplastic diseases in which there is a disregulation of processes mediated by the kinase. It is conceivable that compounds which activate or inhibit the kinases of the invention could have merit as more general modulators of the class of protein kinases which mediate signaling, including (but not limited to) those mentioned herein. Examples of compounds that may modulate kinase activity include but are not limited to catalytically inactive, truncated, or otherwise mutated form of a kinase, preferably a kinase of the present invention; and numerous chemical classes, particularly organic compounds; preferably small organic compounds and are obtained from a wide variety of sources including libraries of synthetic or natural compounds. Preferred modulators of kinase activity are orally active in mammalian hosts. For diagnostic uses, the kinase modulators or other binding agents are frequently labeled, such as with fluorescent, radioactive, chemiluminescent, or other easily detectable molecules, either conjugated directly to the binding agent or conjugated to a probe specific for the binding agent.

Purification Reagents

Each of the polypeptides of the invention finds use as a protein purification reagent. For example, the polypeptides may be used to purify binding partner proteins. In particular embodiments, a polypeptide (in any form described herein that is capable of binding a binding partner) is attached to a solid support by conventional procedures. As one example, affinity chromatography columns containing functional groups that will react with functional groups on amino acid side chains of proteins are available (Pharmacia Biotech, Inc., Piscataway, N.J.).

The polypeptide also finds use in identifying cells that express binding partner proteins. Polypeptides are bound to a solid phase such as a column chromatography matrix or a similar suitable substrate. For example, magnetic microspheres can be coated with the polypeptides and held in an incubation vessel through a magnetic field. Suspensions of cell lysates containing expressed binding partner protein are contacted with the solid phase having the polypeptides thereon. Binding partner proteins from cells expressing the binding partner bind to the fixed polypeptides, and unbound protein is washed away.

Alternatively, the polypeptides can be conjugated to a detectable moiety, then incubated with cell lysates to be tested for binding partner expression. After incubation, unbound labeled matter is removed and the presence or absence of the detectable moiety is determined.

In a further alternative, mixtures of cell lysates suspected of containing binding partner protein are incubated with biotinylated polypeptides of the invention. Incubation periods are typically at least one hour in duration to ensure sufficient binding. The resulting mixture then is passed through a column packed with avidin-coated beads, whereby the high affinity of biotin for avidin provides binding of the desired cells to the beads. Procedures for using avidin-coated beads are known (see Berenson, et al. *J. Cell. Biochem.*, 10D:239, 1986). Washing to remove unbound material, and the release of the bound cells, are performed using conventional methods.

Measuring Activity

Polypeptides also find use in measuring the biological activity of binding partner protein in terms of their binding affinity. The polypeptides thus may be employed by those conducting "quality assurance" studies, e.g., to monitor shelf life and stability of protein under different conditions. For example, the polypeptides may be employed in a binding affinity study to measure the biological activity of a binding partner protein that has been stored at different temperatures, or produced in different cell types. The proteins also may be used to determine whether biological activity is retained after modification of a binding partner protein (e.g., chemical modification, truncation, mutation, etc.). The binding affinity of the modified binding partner protein is compared to that of an unmodified binding partner protein to detect any adverse impact of the modifications on biological activity of binding partner. The biological activity of a binding partner protein thus can be ascertained before it is used in a research study, for example.

In particularly preferred embodiments, the isolated kinase polypeptide fragments can be used to assay protein kinase activity.

Research Agents

Another embodiment of the invention is the use of isolated kinase polypeptides of the invention, fusion proteins, or a fragment thereof containing the isolated protein kinase domain in in vitro or in vivo assays to determine protein kinase activity. A hallmark of protein kinases is their ability to phosphorylate other proteins and to auto-phosphorylate. Therefore, in one aspect of the invention, the isolated polypeptides with kinase activity can be used in assays to phosphorylate target proteins, radiolabel target proteins with $^{32}P$, and identify proteins having phosphatase activity. Exemplary methods of phosphorylation assays set forth above are disclosed in U.S. Pat. No. 5,447,860 which is incorporated herein by reference. In addition to full length polypeptides, the invention also includes the isolated active kinase domains of kinases which can function as reagents in kinase assays.

Kinase assays are typically carried out by combining a kinase of the invention, or an active kinase domain, with radiolabeled ATP ($\gamma^{32}$P-ATP) and a peptide or protein substrate in a buffer solution. The peptide substrates generally range from 8 to 30 amino acids in length or the substrate may also be a protein known to be phosphorylated readily by a kinase of the invention. Many such general kinase substrates are known, e.g. α or β casein, histone H1, myelin basic protein, etc. After incubation of this reaction mixture at 20–37° C. for a suitable time, the kinase mediated transfer of radioactive phosphate from ATP to the substrate protein or substrate peptide can be determined by methods well known in the art, such as, for example, spotting the radioactive products onto phosphocellulose paper, followed by washing and liquid scintillation counting, gel electrophoresis followed by autoradiography, and scintillation proximity assay.

Another embodiment of the invention relates to the study of cell signal transduction. The kinases of the invention, like other kinases, could play a central role in immune responses or other cellular process which include cellular signal transduction. As such, alterations in the expression and/or activation of the kinases can have profound effects on a plethora of cellular processes. Expression of cloned kinases, functionally inactive mutants thereof, or the kinase domain can be used to identify the role a particular protein plays in mediating specific signaling events.

Cellular signaling often involves a molecular activation cascade, during which a receptor propagates a ligand-receptor mediated signal by specifically activating intracellular kinases which phosphorylate target substrates. These substrates can themselves be kinases which become activated following phosphorylation. Alternatively, they can be adaptor molecules that facilitate down stream signaling through protein-protein interaction following phosphorylation. Regardless of the nature of the substrate molecule(s), expressed functionally active versions of the polypeptides of the invention, for example the kinase domain, can be used in assays such as the yeast 2-hybrid assay to identify what substrate(s) were recognized and activated by the kinase binding partner(s). As such, these novel kinases can be used as reagents to identify novel molecules involved in signal transduction pathways.

More specifically, MDCK-1 and LNRK-1, with their strong homologies to human HPK/GCK-like kinase HGK and murine NIK and similarities to other members of the GC (for Germinal Center) kinase family, may be implicated as upstream activators of the Jun terminal kinases. Because JNKs are characteristically activated in response to a variety of cellular signals, MDCK-1 and LNRK-1 (as cDNA, polypeptides, or antibodies) may be used for the study of signal transduction cascades in tissues where the kinases are expressed.

Molecular Weight, Isoelectric Point Markers

The polypeptides of the present invention can be subjected to fragmentation into smaller peptides by chemical and enzymatic means, and the peptide fragments so produced can be used in the analysis of other proteins or polypeptides. For example, such peptide fragments can be used as peptide molecular weight markers, peptide isoelectric point markers, or in the analysis of the degree of peptide fragmentation. Thus, the invention also includes these polypeptides and peptide fragments, as well as kits to aid in the determination of the apparent molecular weight and isoelectric point of an unknown protein and kits to assess the degree of fragmentation of an unknown protein.

Although all methods of fragmentation are encompassed by the invention, chemical fragmentation is a preferred embodiment, and includes the use of cyanogen bromide to cleave under neutral or acidic conditions such that specific cleavage occurs at methionine residues (E. Gross, *Methods in Enz.* 11:238–255, 1967). This can further include additional steps, such as a carboxymethylation step to convert cysteine residues to an unreactive species.

Enzymatic fragmentation is another preferred embodiment, and includes the use of a protease such as Asparaginylendo-peptidase, Arginylendo-peptidase, Achromobacter protease I, Trypsin, *Staphlococcus aureus* V8 protease, Endoproteinase Asp-N, or Endoproteinase Lys-C under conventional conditions to result in cleavage at specific amino acid residues. Asparaginylendo-peptidase can cleave specifically on the carboxyl side of the asparagine residues present within the polypeptides of the invention. Arginylendo-peptidase can cleave specifically on the carboxyl side of the arginine residues present within these polypeptides. Achromobacter protease I can cleave specifically on the carboxyl side of the lysine residues present within the polypeptides (Sakiyama and Nakat, U.S. Pat. No. 5,248,599; T. Masaki et al., *Biochim. Biophys. Acta* 660:44–50, 1981; T. Masaki et al., *Biochim. Biophys. Acta* 660:51–55, 1981). Trypsin can cleave specifically on the carboxyl side of the arginine and lysine residues present within polypeptides of the invention. Enzymatic fragmentation may also occur with a protease that cleaves at multiple amino acid residues. For example, *Staphlococcus aureus* V8 protease can cleave specifically on the carboxyl side of the aspartic and glutamic acid residues present within polypeptides (D. W. Cleveland, *J. Biol. Chem.* 3:1102–1106, 1977). Endoproteinase Asp-N can cleave specifically on the amino side of the asparagine residues present within polypeptides. Endoproteinase Lys-C can cleave specifically on the carboxyl side of the lysine residues present within polypeptides of the invention. Other enzymatic and chemical treatments can likewise be used to specifically fragment these polypeptides into a unique set of specific peptides.

Of course, the peptides and fragments of the polypeptides of the invention can also be produced by conventional recombinant processes and synthetic processes well known in the art. With regard to recombinant processes, the polypeptides and peptide fragments encompassed by invention can have variable molecular weights, depending upon the host cell in which they are expressed.

The molecular weight of these polypeptides can also be varied by fusing additional peptide sequences to both the amino and carboxyl terminal ends of polypeptides of the invention. Fusions of additional peptide sequences at the amino and carboxyl terminal ends of polypeptides of the invention can be used to enhance expression of these polypeptides or aid in the purification of the protein. In addition, fusions of additional peptide sequences at the amino and carboxyl terminal ends of polypeptides of the invention will alter some, but usually not all, of the fragmented peptides of the polypeptides generated by enzymatic or chemical treatment. Of course, mutations can be introduced into polypeptides of the invention using routine and known techniques of molecular biology. For example, a mutation can be designed so as to eliminate a site of proteolytic cleavage by a specific enzyme or a site of cleavage by a specific chemically induced fragmentation procedure. The elimination of the site will alter the peptide fingerprint of polypeptides of the invention upon fragmentation with the specific enzyme or chemical procedure.

Because the unique amino acid sequence of each fragment specifies a molecular weight, these fragments can thereafter serve as molecular weight markers using such analysis techniques to assist in the determination of the molecular weight of an unknown protein, polypeptides or fragments thereof. The molecular weight markers of the invention serve particularly well as molecular weight markers for the estimation of the apparent molecular weight of proteins that have similar apparent molecular weights and, consequently, allow increased accuracy in the determination of apparent molecular weight of proteins.

When the invention relates to the use of fragmented peptide molecular weight markers, those markers are preferably at least 10 amino acids in size. More preferably, these fragmented peptide molecular weight markers are between 10 and 100 amino acids in size. Even more preferable are fragmented peptide molecular weight markers between 10 and 50 amino acids in size and especially between 10 and 35 amino acids in size. Most preferable are fragmented peptide molecular weight markers between 10 and 20 amino acids in size.

Among the methods for determining molecular weight are sedimentation, gel electrophoresis, chromatography, and mass spectrometry. A particularly preferred embodiment is denaturing polyacrylamide gel electrophoresis (U. K. Laemmli, *Nature* 227:680–685, 1970). Conventionally, the method uses two separate lanes of a gel containing sodium dodecyl sulfate and a concentration of acrylamide between 6–20%. The ability to simultaneously resolve the marker and the sample under identical conditions allows for increased accuracy. It is understood, of course, that many different techniques can be used for the determination of the molecular weight of an unknown protein using polypeptides of the invention, and that this embodiment in no way limits the scope of the invention.

Each unglycosylated polypeptide or fragment thereof has a pI that is intrinsically determined by its unique amino acid sequence (which pI can be estimated by the skilled artisan using any of the computer programs designed to predict pI values currently available, calculated using any well-known amino acid pKa table, or measured empirically). Therefore these polypeptides and fragments thereof can serve as specific markers to assist in the determination of the isoelectric point of an unknown protein, polypeptide, or fragmented peptide using techniques such as isoelectric focusing. These polypeptide or fragmented peptide markers serve particularly well for the estimation of apparent isoelectric points of unknown proteins that have apparent isoelectric points close to that of the polypeptide or fragmented peptide markers of the invention.

The technique of isoelectric focusing can be further combined with other techniques such as gel electrophoresis to simultaneously separate a protein on the basis of molecular weight and charge. The ability to simultaneously resolve these polypeptide or fragmented peptide markers and the unknown protein under identical conditions allows for increased accuracy in the determination of the apparent isoelectric point of the unknown protein. This is of particular interest in techniques, such as two dimensional electrophoresis (T. D. Brock and M. T. Madigan, *Biology of Microorganisms* 76–77 (Prentice Hall, 6d ed. 1991)), where the nature of the procedure dictates that any markers should be resolved simultaneously with the unknown protein. In addition, with such methods, these polypeptides and fragmented peptides thereof can assist in the determination of both the isoelectric point and molecular weight of an unknown protein or fragmented peptide.

Polypeptides and fragmented peptides can be visualized using two different methods that allow a discrimination between the unknown protein and the molecular weight markers. In one embodiment, the polypeptide and fragmented peptide molecular weight markers of the invention can be visualized using antibodies generated against these markers and conventional immunoblotting techniques. This detection is performed under conventional conditions that do not result in the detection of the unknown protein. It is understood that it may not be possible to generate antibodies against all polypeptide fragments of the invention, since small peptides may not contain immunogenic epitopes. It is further understood that not all antibodies will work in this assay; however, those antibodies which are able to bind polypeptides and fragments of the invention can be readily determined using conventional techniques.

The unknown protein is also visualized by using a conventional staining procedure. The molar excess of unknown protein to polypeptide or fragmented peptide molecular weight markers of the invention is such that the conventional staining procedure predominantly detects the unknown protein. The level of these polypeptide or fragmented peptide molecular weight markers is such as to allow little or no detection of these markers by the conventional staining method. The preferred molar excess of unknown protein to polypeptide molecular weight markers of the invention is between 2 and 100,000 fold. More preferably, the preferred molar excess of unknown protein to these polypeptide molecular weight markers is between 10 and 10,000 fold and especially between 100 and 1,000 fold.

It is understood of course that many techniques can be used for the determination and detection of molecular weight and isoelectric point of an unknown protein, polypeptides, and fragmented peptides thereof using these polypeptide molecular weight markers and peptide fragments thereof and that these embodiments in no way limit the scope of the invention.

In another embodiment, the analysis of the progressive fragmentation of the polypeptides of the invention into specific peptides (D. W. Cleveland et al., *J. Biol. Chem.* 252:1102–1106, 1977), such as by altering the time or temperature of the fragmentation reaction, can be used as a control for the extent of cleavage of an unknown protein. For example, cleavage of the same amount of polypeptide and unknown protein under identical conditions can allow for a direct comparison of the extent of fragmentation. Conditions that result in the complete fragmentation of the polypeptide can also result in complete fragmentation of the unknown protein.

As to the specific use of the polypeptides and fragmented peptides of the invention as molecular weight markers, the fragmentation of the polypeptide of SEQ ID NOs:8–14 with cyanogen bromide generates a unique set of fragmented peptide molecular weight markers (See Tables I–VI). The distribution of methionine residues determines the number of amino acids in each peptide and the unique amino acid composition of each peptide determines its molecular weight.

TABLE I

Cleavage of MDCK-1 with cyanogen bromide

| Position | From–To | Molecular Weight |
|---|---|---|
| 1 | 1–1 | 149.2 |
| 8 | 237–239 | 383.5 |
| 7 | 227–236 | 1003.1 |
| 3 | 57–72 | 1951.0 |
| 6 | 196–226 | 3459.7 |
| 4 | 73–105 | 3892.5 |
| 2 | 2–56 | 5810.6 |

TABLE I-continued

Cleavage of MDCK-1 with cyanogen bromide

| Position | From–To | Molecular Weight |
|---|---|---|
| 9 | 240–313 | 8251.6 |
| 5 | 106–195 | 10037.5 |

TABLE II

Cleavage of MDCK-2 with cyanogen bromide

| Position | From–To | Molecular Weight |
|---|---|---|
| 1 | 1–1 | 149.2 |
| 12 | 296–303 | 671.7 |
| 7 | 153–158 | 784.9 |
| 2 | 2–8 | 793.8 |
| 10 | 230–241 | 1327.5 |
| 3 | 9–26 | 2038.4 |
| 9 | 204–229 | 3102.5 |
| 6 | 123–152 | 3744.5 |
| 8 | 159–203 | 4838.6 |
| 4 | 27–71 | 5089.9 |
| 5 | 72–122 | 5790.5 |
| 11 | 242–295 | 6385.2 |

TABLE III

Cleavage of MDCK-3 with cyanogen bromide

| Position | From–To | Molecular Weight |
|---|---|---|
| 1 | 1–1 | 149.2 |
| 6 | 172–178 | 734.8 |
| 5 | 163–171 | 997.2 |
| 4 | 139–162 | 2878.2 |
| 9 | 320–355 | 3709.0 |
| 3 | 99–138 | 4662.3 |
| 8 | 261–319 | 6794.6 |
| 7 | 179–260 | 9284.3 |
| 2 | 2–98 | 10881.4 |

TABLE IV

Cleavage of MLSK-1 with cyanogen bromide

| Position | From–To | Molecular Weight |
|---|---|---|
| 1 | 1–1 | 149.2 |
| 4 | 109–133 | 2815.3 |
| 2 | 2–39 | 3888.4 |
| 6 | 253–289 | 4182.8 |
| 7 | 290–336 | 5186.6 |
| 8 | 337–387 | 5736.5 |
| 3 | 40–108 | 8283.6 |
| 5 | 134–252 | 13554.3 |
| 9 | 388–631 | 26152.9 |

TABLE V

Cleavage of MLSK-2 with cyanogen bromide

| Position | From–To | Molecular Weight |
|---|---|---|
| 1 | 1–1 | 149.2 |
| 6 | 181–184 | 446.5 |
| 5 | 165–180 | 1915.2 |
| 3 | 92–118 | 3149.7 |
| 8 | 265–311 | 5276.8 |
| 4 | 119–164 | 5279.1 |

TABLE V-continued

Cleavage of MLSK-2 with cyanogen bromide

| Position | From–To | Molecular Weight |
|---|---|---|
| 7 | 185–264 | 9036.3 |
| 2 | 2–91 | 10174.7 |

TABLE VI

Cleavage of LNRK-1 with cyanogen bromide

| Position | From–To | Molecular Weight |
|---|---|---|
| 11 | 285–431 | 18345.0 |
| 17 | 824–879 | 5992.1 |
| 12 | 432–525 | 12060.5 |
| 3 | 57–72 | 1879.0 |
| 13 | 526–551 | 2971.3 |
| 25 | 1253–1254 | 278.3 |
| 20 | 958–965 | 858.9 |
| 1 | 1–1 | 149.2 |
| 31 | 1358–1358 | 149.2 |
| 30 | 1351–1357 | 834.9 |
| 19 | 905–957 | 5627.1 |
| 9 | 237–239 | 383.5 |
| 32 | 1359–1360 | 318.3 |
| 18 | 880–904 | 2576.8 |
| 8 | 227–236 | 1003.1 |
| 22 | 1070–1091 | 2693.1 |
| 5 | 98–105 | 1019.2 |
| 27 | 1283–1295 | 1460.7 |
| 28 | 1296–1317 | 2431.7 |
| 29 | 1318–1350 | 3877.5 |
| 26 | 1255–1282 | 3280.7 |
| 14 | 552–584 | 3584.0 |
| 4 | 73–97 | 2935.4 |
| 15 | 585–635 | 5487.2 |
| 7 | 196–226 | 3415.7 |
| 16 | 636–823 | 20422.3 |
| 2 | 2–56 | 5858.6 |
| 10 | 240–284 | 5311.2 |
| 21 | 966–1069 | 11599.8 |
| 6 | 106–195 | 10251.7 |
| 24 | 1181–1252 | 7943.0 |
| 23 | 1092–1180 | 10501.4 |

In addition, the preferred purified polypeptide of the invention (SEQ ID NOs:8–14) have calculated molecular weights in the absence of glycosylation as follows:

TABLE VII

| Polypeptide | Daltons |
|---|---|
| MDCK-1 (SEQ ID NO:8) | $M_r$~34,813 and |
| MDCK-2 (SEQ ID NO:9) | $M_r$~34,537 (from MET 3) |
|  | $M_r$~33,761 (from MET 10) |
|  | $M_r$~31,740 (from MET 28) |
| MDCK-3 (SEQ ID NO:10) | $M_r$~39,947 |
| MLSK-1 (SEQ ID NO:11) | $M_r$~69,806 |
| MLSK-2 (SEQ ID NO:13) | $M_r$~39,477 |
| SS4694 (SEQ ID NO:13) | $M_r$~29,954 |
| LNRK-1 (SEQ ID NO:14) | $M_r$~154,943 |

Finally, as to the kits that are encompassed by the invention, the constituents of such kits can be varied, but typically contain the polypeptide and fragmented peptide molecular weight markers. Also, such kits can contain the polypeptides wherein a site necessary for fragmentation has been removed. Furthermore, the kits can contain reagents for the specific cleavage of the polypeptide and the unknown protein by chemical or enzymatic cleavage. Kits can further contain antibodies directed against polypeptides or fragments thereof of the invention.

Identification of Unknown Proteins

As set forth above, a polypeptide or peptide fingerprint can be entered into or compared to a database of known proteins to assist in the identification of the unknown protein using mass spectrometry (W. J. Henzel et al., Proc. Natl. Acad. Sci. USA 90:5011–5015, 1993; D. Fenyo et al., Electrophoresis 19:998–1005, 1998). A variety of computer software programs to facilitate these comparisons are accessible via the Internet, such as Protein Prospector (Internet site: prospector.uscf.edu), MultiIdent (Internet site: www.expasy.ch/sprot/multiident.html), PeptideSearch (Internet site:www.mann.emblheiedelberg.de...deSearch/ FR_PeptideSearch Form.html), and ProFound (Internet site: www.chait-sgi.rockefeller.edu/cgi-bin/ prot-id-frag.html). These programs allow the user to specify the cleavage agent and the molecular weights of the fragmented peptides within a designated tolerance. The programs compare observed molecular weights to predicted peptide molecular weights derived from sequence databases to assist in determining the identity of the unknown protein.

In addition, a polypeptide or peptide digest can be sequenced using tandem mass spectrometry (MS/MS) and the resulting sequence searched against databases (J. K. Eng, et al., J. Am. Soc. Mass Spec. 5:976–989 (1994); M. Mann and M. Wilm, Anal. Chem. 66:43904399 (1994); J. A. Taylor and R. S. Johnson, Rapid Comm. Mass Spec.11: 1067–1075 (1997)). Searching programs that can be used in this process exist on the Internet, such as Lutefisk 97 (Internet site: www.lsbc.com:70/Lutefisk97.html), and the Protein Prospector, Peptide Search and ProFound programs described above.

Therefore, adding the sequence of a gene and its predicted protein sequence and peptide fragments to a sequence database can aid in the identification of unknown proteins using mass spectrometry.

Antibodies

Antibodies that are immunoreactive with the polypeptides of the invention are provided herein. Such antibodies specifically bind to the polypeptides via the antigen-binding sites of the antibody (as opposed to non-specific binding). Thus, the polypeptides, fragments, variants, fusion proteins, etc., as set forth above may be employed as "immunogens" in producing antibodies immunoreactive therewith. More specifically, the polypeptides, fragment, variants, fusion proteins, etc. contain antigenic determinants or epitopes that elicit the formation of antibodies.

These antigenic determinants or epitopes can be either linear or conformational (discontinuous). Linear epitopes are composed of a single section of amino acids of the polypeptide, while conformational or discontinuous epitopes are composed of amino acids sections from different regions of the polypeptide chain that are brought into close proximity upon protein folding (C. A. Janeway, Jr. and P. Travers, *Immuno Biology* 3:9 (Garland Publishing Inc., 2nd ed. 1996)). Because folded proteins have complex surfaces, the number of epitopes available is quite numerous; however, due to the conformation of the protein and steric hinderances, the number of antibodies that actually bind to the epitopes is less than the number of available epitopes (C. A. Janeway, Jr. and P. Travers, *Immuno Biology* 2:14 (Garland Publishing Inc., 2nd ed. 1996)). Epitopes may be identified by any of the methods known in the art.

Thus, one aspect of the present invention relates to the antigenic epitopes of the polypeptides of the invention. Such epitopes are useful for raising antibodies, in particular monoclonal antibodies, as described in more detail below. Additionally, epitopes from the polypeptides of the invention can be used as research reagents, in assays, and to purify specific binding antibodies from substances such as polyclonal sera or supernatants from cultured hybridomas. Such epitopes or variants thereof can be produced using techniques well known in the art such as solid-phase synthesis, chemical or enzymatic cleavage of a polypeptide, or using recombinant DNA technology.

As to the antibodies that can be elicited by the epitopes of the polypeptides of the invention, whether the epitopes have been isolated or remain part of the polypeptides, both polyclonal and monoclonal antibodies may be prepared by conventional techniques. See, for example, *Monoclonal Antibodies, Hybridomas: A New Dimension in Biological Analyses,* Kennet et al. (eds.), Plenum Press, New York (1980); and *Antibodies: A Laboratory Manual,* Harlow and Land (eds.), Cold Spring Harbor Laboratory Press, Cold Spring Harbor, N.Y., (1988).

Hybridoma cell lines that produce monoclonal antibodies specific for the polypeptides of the invention are also contemplated herein. Such hybridomas may be produced and identified by conventional techniques. One method for producing such a hybridoma cell line comprises immunizing an animal with a polypeptide; harvesting spleen cells from the immunized animal; fusing said spleen cells to a myeloma cell line, thereby generating hybridoma cells; and identifying a hybridoma cell line that produces a monoclonal antibody that binds the polypeptide. The monoclonal antibodies may be recovered by conventional techniques.

The monoclonal antibodies of the present invention include chimeric antibodies, e.g., humanized versions of murine monoclonal antibodies. Such humanized antibodies may be prepared by known techniques and offer the advantage of reduced immunogenicity when the antibodies are administered to humans. In one embodiment, a humanized monoclonal antibody comprises the variable region of a murine antibody (or just the antigen binding site thereof) and a constant region derived from a human antibody. Alternatively, a humanized antibody fragment may comprise the antigen binding site of a murine monoclonal antibody and a variable region fragment (lacking the antigen-binding site) derived from a human antibody. Procedures for the production of chimeric and further engineered monoclonal antibodies include those described in Riechmann et al. (*Nature* 332:323, 1988), Liu et al. (*PNAS* 84:3439, 1987), Larrick et al. (*Bio/Technology* 7:934, 1989), and Winter and Harris (*TIPS* 14:139, May, 1993). Procedures to generate antibodies transgenically can be found in GB 2,272,440, U.S. Pat. Nos. 5,569,825 and 5,545,806 and related patents claiming priority therefrom, all of which are incorporated by reference herein.

Antigen-binding fragments of the antibodies, which may be produced by conventional techniques, are also encompassed by the present invention. Examples of such fragments include, but are not limited to, Fab and F(ab')$_2$ fragments. Antibody fragments and derivatives produced by genetic engineering techniques are also provided.

In one embodiment, the antibodies are specific for the polypeptides of the present invention and do not cross-react with other proteins. Screening procedures by which such antibodies may be identified are well known, and may involve immunoaffinity chromatography, for example.

Uses Thereof

The antibodies of the invention can be used in assays to detect the presence of the polypeptides or fragments of the invention, either in vitro or in vivo. The antibodies also may be employed in purifying polypeptides or fragments of the invention by immunoaffinity chromatography.

Those antibodies that additionally can block binding of the polypeptides of the invention to a binding partner may be used to inhibit a biological activity that results from such binding. Such blocking antibodies may be identified using any suitable assay procedure, such as by testing antibodies for the ability to inhibit binding of kinases of the invention to the binding partner. Alternatively, blocking antibodies may be identified in assays for the ability to inhibit a biological effect that results from binding of kinases to binding partners.

Such an antibody may be employed in an in vitro procedure, or administered in vivo to inhibit a biological activity mediated by the entity that generated the antibody. Disorders caused or exacerbated (directly or indirectly) by the interaction of kinases with binding partners thus may be treated. A therapeutic method involves in vivo administration of a blocking antibody to a mammal in an amount effective in inhibiting a binding partner-mediated biological activity. Monoclonal antibodies are generally preferred for use in such therapeutic methods. In one embodiment, an antigen-binding antibody fragment is employed.

Antibodies may be screened for agonistic (i.e., ligand-mimicking) properties. Such antibodies, upon binding to a binding partner, induce biological effects (e.g., transduction of biological signals) similar to the biological effects induced when the kinases of the invention bind to binding partners.

Compositions comprising an anti-kinase antibody, and a physiologically acceptable diluent, excipient, or carrier, are provided herein. Suitable components of such compositions are as described above for compositions containing kinase proteins.

Also provided herein are conjugates comprising a detectable (e.g., diagnostic) or therapeutic agent, attached to the antibody. Examples of such agents are presented above. The conjugates find use in in vitro or in vivo procedures.

Therapeutic Activities

The polynucleotides and proteins of the present invention are expected to exhibit one or more of the therapuetic uses or biological activities (including those associated with assays cited herein) identified below. Therapeutic uses or activities described for proteins of the present invention may be provided by administration or use of such proteins or by administration or use of polynucleotides encoding such proteins (such as, for example, in gene therapies or vectors suitable for introduction of DNA).

Cytokine and Cell Proliferation/Differentiation Activity

A protein of the present invention may exhibit cytokine-inducing, cell proliferation (either inducing or inhibiting) or cell differentiation (either inducing or inhibiting) activity or may induce or inhibit production of cytokines in certain cell populations. The cell-proliferation activity of a protein of the present invention is evidenced by any one of a number of routine factor dependent cell proliferation assays for cell lines including, without limitation, 32D, DA2, DA1G, T10, B9, B9/11, BaF3, MC9/G, M+(preB M+), 2E8, RB5, DA1, 123, T1165, HT2, CTLL2, TF-1, Mo7e and CMK. The activity of a protein of the invention may, among other means, be measured by the following methods: Assays for T-cell or thymocyte proliferation include without limitation those described in: Current Protocols in Immunology, Ed by J. E. Coligan, A. M. Kruisbeek, D. H. Margulies, E. M. Shevach, W Strober, Pub. Greene Publishing Associates and Wiley-Interscience (Chapter 3, In Vitro assays for Mouse Lymphocyte Function 3.1–3.19; Chapter 7, Immunologic studies in Humans); Takai et al., J. Immunol. 137:3494–3500, 1986; Bertagnolli et al., J. Immunol. 145:1706–1712, 1990; Bertagnolli et al., Cellular Immunology 133:327–341, 1991; Bertagnolli, et al., J. Immunol. 149:3778–3783, 1992; Bowman et al., J. Immunol. 152: 1756–1761, 1994. Assays for cytokine production and/or proliferation of spleen cells, lymph node cells or thymocytes include, without limitation, those described in: Polyclonal T cell stimulation, Kruisbeek, A. M. and Shevach, E. M. In Current Protocols in Immunology. J. E. e.a. Coligan eds. Vol 1 pp. 3.12.1–3.12.14, John Wiley and Sons, Toronto. 1994; and Measurement of mouse and human Interferon gamma., Schreiber, R. D. In Current Protocols in Immunology. J. E. e.a. Coligan eds. Vol 1 pp. 6.8.1–6.8.8, John Wiley and Sons, Toronto. 1994. Assays for proliferation and differentiation of hematopoietic and lymphopoietic cells include, without limitation, those described in: Measurement of Human and Murine Interleukin 2 and Interleukin 4, Bottomly, K., Davis, L. S. and Lipsky, P. E. In Current Protocols in Immunology. J. E. e.a. Coligan eds. Vol 1 pp. 6.3.1–6.3.12, John Wiley and Sons, Toronto. 1991; deVries et al., J. Exp. Med. 173:1205–1211, 1991; Moreau et al., Nature 336:690–692, 1988; Greenberger et al., Proc. Natl. Acad. Sci. U.S.A. 80:2931–2938, 1983; Measurement of mouse and human interleukin 6-Nordan, R. In Current Protocols in Immunology. J. E. e.a. Coligan eds. Vol 1 pp. 6.6.1–6.6.5, John Wiley and Sons, Toronto. 1991; Smith et al., Proc. Natl. Acad. Sci. U.S.A. 83:1857–1861, 1986; Measurement of human Interleukin 11-Bennett, F., Giannotti, J., Clark, S. C. and Turner, K. J. In Current Protocols in Immunology. J. E. e.a. Coligan eds. Vol 1 pp. 6.15.1 John Wiley and Sons, Toronto. 1991; Measurement of mouse and human Interleukin 9-Ciarletta, A., Giannotti, J., Clark, S. C. and Turner, K. J. In Current Protocols in Immunology. J. E. e.a. Coligan eds. Vol 1 pp. 6.13.1, John Wiley and Sons, Toronto. 1991.

Immune Stimulating or Suppressing Activity

A protein of the present invention may also exhibit immune stimulating or immune suppressing activity, including without limitation the activities for which assays are described herein. A protein may be useful in the treatment of various immune deficiencies and disorders (including severe combined immunodeficiency (SCID)), e.g., in regulating (up or down) growth and proliferation of T and/or B lymphocytes, as well as effecting the cytolytic activity of NK cells and other cell populations. These immune deficiencies may be genetic or be caused by viral (e.g., HIV) as well as bacterial or fungal infections, or may result from autoimmune disorders. More specifically, infectious diseases causes by viral, bacterial, fungal or other infection may be treatable using a protein of the present invention, including infections by HIV, hepatitis viruses, herpesviruses, mycobacteria, Leishmania spp., malaria spp. and various fungal infections such as candidiasis. Of course, in this regard, a protein of the present invention may also be useful where a boost to the immune system generally may be desirable, i.e., in the treatment of cancer.

Autoimmune disorders which may be treated using a protein of the present invention include, for example, connective tissue disease, multiple sclerosis, systemic lupus erythematosus, rheumatoid arthritis, autoimmune pulmonary inflammation, Guillain-Barre syndrome, autoimmune thyroiditis, insulin dependent diabetes mellitis, myasthenia gravis, graft-versus-host disease and autoimmune inflammatory eye disease. Such a protein of the present invention may also to be useful in the treatment of allergic reactions and conditions, such as asthma (particularly allergic asthma) or other respiratory problems. Other conditions, in which immune suppression is desired (including, for example, organ transplantation), may also be treatable using a protein of the present invention.

Using the proteins of the invention it may also be possible to immune responses, in a number of ways. Down regulation may be in the form of inhibiting or blocking an immune response already in progress or may involve preventing the induction of an immune response. The functions of activated T cells may be inhibited by suppressing T cell responses or by inducing specific tolerance in T cells, or both. Immunosuppression of T cell responses is generally an active, non-antigen-specific, process which requires continuous exposure of the T cells to the suppressive agent. Tolerance, which involves inducing non-responsiveness or anergy in T cells, is distinguishable from immunosuppression in that it is generally antigen-specific and persists after exposure to the tolerizing agent has ceased. Operationally, tolerance can be demonstrated by the lack of a T cell response upon reexposure to specific antigen in the absence of the tolerizing agent.

Down regulating or preventing one or more antigen functions (including without limitation B lymphocyte antigen functions (such as, for example, B7)), e.g., preventing high level lymphokine synthesis by activated T cells, will be useful in situations of tissue, skin and organ transplantation and in graft-versus-host disease (GVHD). For example, blockage of T cell function should result in reduced tissue destruction in tissue transplantation. Typically, in tissue transplants, rejection of the transplant is initiated through its recognition as foreign by T cells, followed by an immune reaction that destroys the transplant. To achieve sufficient immunosuppression or tolerance in a subject, it may also be necessary to block the function of a combination of B lymphocyte antigens.

Upregulation of an antigen function (preferably a B lymphocyte antigen function), as a means of up regulating immune responses, may also be useful in therapy. Upregulation of immune responses may be in the form of enhancing an existing immune response or eliciting an initial immune response. For example, enhancing an immune response through stimulating B lymphocyte antigen function may be useful in cases of viral infection. In addition, systemic viral diseases such as influenza, the common cold, and encephalitis might be alleviated by the administration of stimulatory forms of B lymphocyte antigens systemically.

Alternatively, anti-viral immune responses may be enhanced in an infected patient by removing T cells from the patient, costimulating the T cells in vitro with viral antigen-pulsed APCs either expressing a peptide of the present invention or together with a stimulatory form of a soluble peptide of the present invention and reintroducing the in vitro activated T cells into the patient. Another method of enhancing anti-viral immune responses would be to isolate infected cells from a patient, transfect them with a nucleic acid encoding a protein of the present invention as described herein such that the cells express the protein, and reintroduce the transfected cells into the patient. The infected cells would now be capable of delivering a costimulatory signal to, and thereby activate, T cells in vivo.

In another application, up regulation or enhancement of antigen function (preferably B lymphocyte antigen function) may be useful in the induction of tumor immunity. Tumor cells (e.g., sarcoma, melanoma, lymphoma, leukemia, neuroblastoma, carcinoma) transfected with a nucleic acid encoding at least one peptide of the present invention can be administered to a subject to overcome tumor-specific tolerance in the subject. If desired, the tumor cell can be transfected to express a combination of peptides. The transfected tumor cells are returned to the patient to result in expression of the peptides in the transfected cell. Alternatively, gene therapy techniques can be used to target a tumor cell for transfection in vivo.

The activity of a protein of the invention may, among other means, be measured by the following methods: Suitable assays for thymocyte or splenocyte cytotoxicity include, without limitation, those described in: Current Protocols in Immunology, Ed by J. E. Coligan, A. M. Kruisbeek, D. H. Margulies, E. M. Shevach, W Strober, Pub. Greene Publishing Associates and Wiley-Interscience (Chapter 3, In Vitro assays for Mouse Lymphocyte Function 3.1–3.19; Chapter 7, Immunologic studies in Humans); Herrmann et al., Proc. Natl. Acad. Sci. U.S.A. 78:2488–2492, 1981; Herrmann et al., J. Immunol. 128:1968–1974, 1982; Handa et al., J. Immunol. 135:1564–1572, 1985; Takai et al., J. Immunol. 137:3494–3500, 1986; Takai et al., J. Immunol. 140:508–512, 1988; Herrmann et al., Proc. Natl. Acad. Sci. U.S.A. 78:2488–2492, 1981; Herrmann et al., J. Immunol. 128:1968–1974, 1982; Handa et al., J. Immunol. 135:1564–1572, 1985; Takai et al., J. Immunol. 137:3494–3500, 1986; Bowman et al., J. Virology 61:1992–1998; Takai et al., J. Immunol. 140:508–512, 1988; Bertagnolli et al., Cellular Immunology 133:327–341, 1991; Brown et al., J. Immunol. 153:3079–3092, 1994. Assays for T-cell-dependent immunoglobulin responses and isotype switching (which will identify, among others, proteins that modulate T-cell dependent antibody responses and that affect Th1/Th2 profiles) include, without limitation, those described in: Maliszewski, J. Immunol. 144:3028–3033, 1990; and Assays for B cell function: In vitro antibody production, Mond, J. J. and Brunswick, M. In Current Protocols in Immunology. J. E. e.a. Coligan eds. Vol 1 pp. 3.8.1–3.8.16, John Wiley and Sons, Toronto. 1994. Mixed lymphocyte reaction (MLR) assays (which will identify, among others, proteins that generate predominantly Th1 and CTL responses) include, without limitation, those described in: Current Protocols in Immunology, Ed by J. E. Coligan, A. M. Kruisbeek, D. H. Margulies, E. M. Shevach, W Strober, Pub. Greene Publishing Associates and Wiley-Interscience (Chapter 3, In Vitro assays for Mouse Lymphocyte Function 3.1–3.19; Chapter 7, Immunologic studies in Humans); Takai et al., J. Immunol. 137:3494–3500, 1986; Takai et al., J. Immunol. 140:508–512, 1988; Bertagnolli et al., J. Immunol. 149:3778–3783, 1992. Dendritic cell-dependent assays (which will identify, among others, proteins expressed by dendritic cells that activate naive T-cells) include, without limitation, those described in: Guery et al., J. Immunol. 134:536–544, 1995; Inaba et al., Journal of Experimental Medicine 173:549–559, 1991; Macatonia et al., Journal of Immunology 154:5071–5079, 1995; Porgador et al., Journal of Experimental Medicine 182:255–260, 1995; Nair et al., Journal of Virology 67:4062–4069, 1993; Huang et al., Science 264:961–965, 1994; Macatonia et al., Journal of Experimental Medicine 169:1255–1264, 1989; Bhardwaj et al., Journal of Clinical Investigation 94:797–807, 1994; and Inaba et al., Journal of Experimental Medicine 172:631–640, 1990.

Assays for lymphocyte survival/apoptosis (which will identify, among others, proteins that prevent apoptosis after superantigen induction and proteins that regulate lymphocyte homeostasis) include, without limitation, those described in: Darzynkiewicz et al., Cytometry 13:795–808, 1992; Gorczyca et al., Leukemia 7:659–670, 1993; Gorczyca et al., Cancer Research 53:1945–1951, 1993; Itoh et al., Cell 66:233–243, 1991; Zacharchuk, Journal of Immunology 145:4037–4045, 1990; Zamai et al., Cytometry 14:891–897, 1993; Gorczyca et al., International Journal of Oncology 1:639–648, 1992.

Assays for proteins that influence early steps of T-cell commitment and development include, without limitation, those described in: Antica et al., Blood 84:111–117, 1994; Fine et al., Cellular Immunology 155:111–122, 1994; Galy et al., Blood 85:2770–2778, 1995; Toki et al., Proc. Nat. Acad Sci. U.S.A. 88:7548–7551, 1991.

Hematopoiesis Regulating Activity

A protein of the present invention may be useful in regulation of hematopoiesis and, consequently, in the treatment of myeloid or lymphoid cell deficiencies. Even marginal biological activity in support of colony forming cells or of factor-dependent cell lines indicates involvement in regulating hematopoiesis, e.g. in supporting the growth and proliferation of erythroid progenitor cells alone or in combination with other cytokines, thereby indicating utility, for example, in treating various anemias or for use in conjunction with irradiation/chemotherapy to stimulate the production of erythroid precursors and/or erythroid cells; in supporting the growth and proliferation of myeloid cells such as granulocytes and monocytes/macrophages (i.e., traditional CSF activity) useful, for example, in conjunction with chemotherapy to prevent or treat consequent myelosuppression; in supporting the growth and proliferation of megakaryocytes and consequently of platelets thereby allowing prevention or treatment of various platelet disorders such as thrombocytopenia, and generally for use in place of or complimentary to platelet transfusions; and/or in supporting the growth and proliferation of hematopoietic stem cells which are capable of maturing to any and all of the above-mentioned hematopoietic cells and therefore find therapeutic utility in various stem cell disorders (such as those usually treated with transplantation, including, without limitation, aplastic anemia and paroxysmal nocturnal hemoglobinuria), as well as in repopulating the stem cell compartment post irradiation/chemotherapy, either in-vivo or ex-vivo (i.e., in conjunction with bone marrow transplantation or with peripheral progenitor cell transplantation (homologous or heterologous)) as normal cells or genetically manipulated for gene therapy.

The activity of a protein of the invention may, among other means, be measured by the following methods: Suitable assays for proliferation and differentiation of various hematopoietic lines are cited above. Assays for embryonic stem cell differentiation (which will identify, among others, proteins that influence embryonic differentiation hematopoiesis) include, without limitation, those described in: Johansson et al. Cellular Biology 15:141–151, 1995; Keller et al., Molecular and Cellular Biology 13:473–486, 1993; McClanahan et al., Blood 81:2903–2915, 1993. Assays for stem cell survival and differentiation (which will identify, among others, proteins that regulate lymphohematopoiesis) include, without limitation, those described in: Methylcellulose colony forming assays, Freshney, M. G. In Culture of Hematopoietic Cells. R. I. Freshney, et al. eds. Vol pp. 265–268, Wiley-Liss, Inc., New York, N.Y. 1994; Hirayama et al., Proc. Natl. Acad. Sci. U.S.A. 89:5907–5911, 1992; Primitive hematopoietic colony forming cells with high proliferative potential, McNiece, I. K. and Briddell, R. A. In Culture of Hematopoietic Cells. R. I. Freshney, et al. eds. Vol pp. 23–39, Wiley-Liss, Inc., New York, N.Y. 1994; Neben et al., Experimental Hematology 22:353–359, 1994; Cobblestone area forming cell assay, Ploemacher, R. E. In Culture of Hematopoietic Cells. R. I. Freshney, et al. eds. Vol pp. 1–21, Wiley-Liss, Inc.., New York, N.Y. 1994; Long term bone marrow cultures in the presence of stromal cells, Spooncer, E., Dexter, M. and Allen, T. In Culture of Hematopoietic Cells. R. I. Freshney, et al. eds. Vol pp. 163–179, Wiley-Liss, Inc., New York, N.Y. 1994; Long term culture initiating cell assay, Sutherland, H. J. In Culture of Hematopoietic Cells. R. I. Freshney, et al. eds. Vol pp. 139–162, Wiley-Liss, Inc., New York, N.Y. 1994.

Tissue Growth Activity

A protein of the present invention also may have utility in compositions used for bone, cartilage, tendon, ligament and/or nerve tissue growth or regeneration, as well as for wound healing and tissue repair and replacement, and in the treatment of burns, incisions and ulcers. A protein of the present invention, which induces cartilage and/or bone growth in circumstances where bone is not normally formed, has application in the healing of bone fractures and cartilage damage or defects in humans and other animals. Such a preparation employing a protein of the invention may have prophylactic use in closed as well as open fracture reduction and also in the improved fixation of artificial joints. De novo bone formation induced by an osteogenic agent contributes to the repair of congenital, trauma induced, or oncologic resection induced craniofacial defects, and also is useful in cosmetic plastic surgery. A protein of this invention may also be used in the treatment of periodontal disease, and in other tooth repair processes. Such agents may provide an environment to attract bone-forming cells, stimulate growth of bone-forming cells or induce differentiation of progenitors of bone-forming cells. A protein of the invention may also be useful in the treatment of osteoporosis or osteoarthritis, such as through stimulation of bone and/or cartilage repair or by blocking inflammation or processes of tissue destruction (collagenase activity, osteoclast activity, etc.) mediated by inflammatory processes. Another category of tissue regeneration activity that may be attributable to the protein of the present invention is tendon/ligament formation. A protein of the present invention, which induces tendon/ligament-like tissue or other tissue formation in circumstances where such tissue is not normally formed, has application in the healing of tendon or ligament tears, deformities and other tendon or ligament defects in humans and other animals. Such a preparation employing a tendon/ligament-like tissue inducing protein may have prophylactic use in preventing damage to tendon or ligament tissue, as well as use in the improved fixation of tendon or ligament to bone or other tissues, and in repairing defects to tendon or ligament tissue. De novo tendon/ligament-like tissue formation induced by a composition of the present invention contributes to the repair of congenital, trauma induced, or other tendon or ligament defects of other origin, and is also useful in cosmetic plastic surgery for attachment or repair of tendons or ligaments. The compositions of the present invention may provide an environment to attract tendon- or ligament-forming cells, stimulate growth of tendon- or ligament-forming cells, induce differentiation of progenitors of tendon- or ligament-forming cells, or induce growth of tendon/ligament cells or progenitors ex vivo for return in vivo to effect tissue repair. The compositions of the invention may also be useful in the treatment of tendinitis, carpal tunnel syndrome and other tendon or ligament defects. The compositions may also include an appropriate sequestering agent as a carrier as is well known in the art.

The protein of the present invention may also be useful for proliferation of neural cells and for regeneration of nerve and brain tissue, i.e. for the treatment of central and peripheral nervous system diseases and neuropathies, as well as mechanical and traumatic disorders, which involve degeneration, death or trauma to neural cells or nerve tissue. More specifically, a protein may be used in the treatment of diseases of the peripheral nervous system, such as peripheral nerve injuries, peripheral neuropathy and localized neuropathies, and central nervous system diseases, such as Alzheimer's, Parkinson's disease, Huntington's disease, amyotrophic lateral sclerosis, and Shy-Drager syndrome. Further conditions which may be treated in accordance with the present invention include mechanical and traumatic disorders, such as spinal cord disorders, head trauma and cerebrovascular diseases such as stroke. Peripheral neuropathies resulting from chemotherapy or other medical therapies may also be treatable using a protein of the invention.

Proteins of the invention may also be useful to promote better or faster closure of non-healing wounds, including without limitation pressure ulcers, ulcers associated with vascular insufficiency, surgical and traumatic wounds, and the like. It is expected that a protein of the present invention may also exhibit activity for generation or regeneration of other tissues, such as organs (including, for example, pancreas, liver, intestine, kidney, skin, endothelium), muscle (smooth, skeletal or cardiac) and vascular (including vascular endothelium) tissue, or for promoting the growth of cells comprising such tissues. Part of the desired effects may be by inhibition or modulation of fibrotic scarring to allow normal tissue to regenerate. A protein of the invention may also exhibit angiogenic activity. A protein of the present invention may also be useful for gut protection or regeneration and treatment of lung or liver fibrosis, reperfusion injury in various tissues, and conditions resulting from systemic cytokine damage. A protein of the present invention may also be useful for promoting or inhibiting differentiation of tissues described above from precursor tissues or cells; or for inhibiting the growth of tissues described above. The activity of a protein of the invention may, among other means, be measured by the following methods: Assays for tissue generation activity include, without limitation, those described in: International Patent Publication No. WO95/16035 (bone, cartilage, tendon); International Patent Publication No. WO95/05846 (nerve, neuronal); International Patent Publication No. WO91/07491 (skin, endothelium). Assays for wound healing activity include, without limitation, those described in: Winter, Epidermal Wound Healing pps. 71–112 (Maibach, H I and Rovee, D T, eds.), Year Book Medical Publishers, Inc., Chicago, as modified by Eaglstein and Mertz, J. Invest. Dermatol 71:382–84 (1978).

Inflammation

Proteins of the present invention may also exhibit anti-inflammatory activity. The anti-inflammatory activity may be achieved by providing a stimulus to cells involved in the inflammatory response, by inhibiting or promoting cell-cell interactions (such as, for example, cell adhesion), by inhibiting or promoting chemotaxis of cells involved in the inflammatory process, inhibiting or promoting cell extravasation, or by stimulating or suppressing production of other factors which more directly inhibit or promote an inflammatory response. Proteins exhibiting such activities can be used to treat inflammatory conditions including chronic or acute conditions), including without limitation inflammation associated with infection (such as septic shock, sepsis or systemic inflammatory response syndrome (SIRS)), ischemia-reperfusion injury, endotoxin lethality, arthritis, complement-mediated hyperacute rejection, nephritis, cytokine or chemokine-induced lung injury, inflammatory bowel disease, Crohn's disease or resulting from over production of cytokines such as TNF or IL-1. Proteins of the invention may also be useful to treat anaphylaxis and hypersensitivity to an antigenic substance or material.

Tumor Inhibition Activity

In addition to the activities described above for immunological treatment or prevention of tumors, a protein of the invention may exhibit other anti-tumor activities. A protein may inhibit tumor growth directly or indirectly (such as, for example, via ADCC). A protein may exhibit its tumor inhibitory activity by acting on tumor tissue or tumor precursor tissue, by inhibiting formation of tissues necessary to support tumor growth (such as, for example, by inhibiting angiogenesis), by causing production of other factors, agents or cell types which inhibit tumor growth, or by suppressing, eliminating or inhibiting factors, agents or cell types which promote tumor growth.

Other Activities

A protein of the invention may also exhibit one or more of the following additional activities or effects: inhibiting the growth, infection or function of, or killing, infectious agents, including, without limitation, bacteria, viruses, fungi and other parasites; effecting (suppressing or enhancing) bodily characteristics, including, without limitation, height, weight, hair color, eye color, skin, fat to lean ratio or other tissue pigmentation, or organ or body part size or shape (such as, for example, breast augmentation or diminution, change in bone form or shape); effecting biorhythms or caricadic cycles or rhythms; effecting the fertility of male or female subjects; effecting the metabolism, catabolism, anabolism, processing, utilization, storage or elimination of dietary fat, lipid, protein, carbohydrate, vitamins, minerals, cofactors or other nutritional factors or component(s); effecting behavioral characteristics, including, without limitation, appetite, libido, stress, cognition (including cognitive disorders), depression (including depressive disorders) and violent behaviors; providing analgesic effects or other pain reducing effects; promoting differentiation and growth of embryonic stem cells in lineages other than hematopoiefic lineages; hormonal or endocrine activity; in the case of enzymes, correcting deficiencies of the enzyme and treating deficiency-related diseases; treatment of hyperproliferative disorders (such as, for example, psoriasis); immunoglobulin-like activity (such as, for example, the ability to bind antigens or complement); and the ability to act as an antigen in a vaccine composition to raise an immune response against such protein or another material or entity which is cross-reactive with such protein.

Administration and Dosing

A protein of the present invention (from whatever source derived, including without limitation from recombinant and non-recombinant sources) may be used in a pharmaceutical composition when combined with a pharmaceutically acceptable carrier. Such a composition may also contain (in addition to protein and a carrier) diluents, fillers, salts, buffers, stabilizers, solubilizers, and other materials well known in the art. The term "pharmaceutically acceptable" means a non-toxic material that does not interfere with the effectiveness of the biological activity of the active ingredient(s). The characteristics of the carrier will depend on the route of administration.

The pharmaceutical composition of the invention may also contain cytokines, lymphokines, or other hematopoietic factors such as M-CSF, GM-CSF, TNF, IL-1, IL-2, IL-3, IL4, IL-5, IL-6, IL-7, IL-8, IL-9, IL-10, IL-11, IL-12, IL-13, IL-14, IL-15, IFN, TNF0, TNF1, TNF2, G-CSF, Meg-CSF, thrombopoietin, stem cell factor, and erythropoietin. The pharmaceutical composition may further contain other agents which either enhance the activity of the protein or compliment its activity or use in treatment. Such additional factors and/or agents may be included in the pharmaceutical composition to produce a synergistic effect with protein of the invention, or to minimize side effects. Conversely, protein of the present invention may be included in formulations of the particular cytokine, lymphokine, other hematopoietic factor, thrombolytic or anti-thrombotic factor, or anti-inflammatory agent to minimize side effects of the cytokine, lymphokine, other hematopoietic factor, thrombolytic or anti-thrombotic factor, or anti-inflammatory agent.

A protein of the present invention may be active in multimers (e.g., heterodimers or homodimers) or complexes with itself or other proteins. As a result, pharmaceutical compositions of the invention may comprise a protein of the invention in such multimeric or complexed form. The pharmaceutical composition of the invention may be in the form of a complex of the protein(s) of present invention along with protein or peptide antigens. The protein and/or peptide antigen will deliver a stimulatory signal to both B and T lymphocytes. B lymphocytes will respond to antigen through their surface immunoglobulin receptor. T lymphocytes will respond to antigen through the T cell receptor (TCR) following presentation of the antigen by MHC proteins. MHC and structurally related proteins including those encoded by class I and class II MHC genes on host cells will serve to present the peptide antigen(s) to T lymphocytes. The antigen components could also be supplied as purified MHC-peptide complexes alone or with co-stimulatory molecules that can directly signal T cells. Alternatively antibodies able to bind surface immunolgobulin and other molecules on B cells as well as antibodies able to bind the TCR and other molecules on T cells can be combined with the pharmaceutical composition of the invention.

The pharmaceutical composition of the invention may be in the form of a liposome in which protein of the present invention is combined, in addition to other pharmaceutically acceptable carriers, with amphipathic agents such as lipids which exist in aggregated form as micelles, insoluble monolayers, liquid crystals, or lamellar layers in aqueous solution. Suitable lipids for liposomal formulation include, without limitation, monoglycerides, diglycerides, sulfatides, lysolecithin, phospholipids, saponin, bile acids, and the like. Preparation of such liposomal formulations is within the level of skill in the art, as disclosed, for example, in U.S. Pat. No. 4,235,871; U.S. Pat. No. 4,501,728; U.S. Pat. No. 4,837,028; and U.S. Pat. No. 4,737,323, all of which are incorporated herein by reference. As used herein, the term "therapeutically effective amount" means the total amount of each active component of the pharmaceutical composition or method that is sufficient to show a meaningful patient benefit, i.e., treatment, healing, prevention or amelioration of the relevant medical condition, or an increase in rate of treatment, healing, prevention or amelioration of such conditions. When applied to an individual active ingredient, administered alone, the term refers to that ingredient alone. When applied to a combination, the term refers to combined amounts of the active ingredients that result in the therapeutic effect, whether administered in combination, serially or simultaneously.

In practicing the method of treatment or use of the present invention, a therapeutically effective amount of protein of the present invention is administered to a mammal having a condition to be treated. Protein of the present invention may be administered in accordance with the method of the invention either alone or in combination with other therapies such as treatments employing cytokines, lymphokines or other hematopoietic factors. When co-administered with one or more cytokines, lymphokines or other hematopoietic factors, protein of the present invention may be administered either simultaneously with the cytokine(s), lymphokine(s), other hematopoietic factor(s), thrombolytic or anti-thrombotic factors, or sequentially. If administered sequentially, the attending physician will decide on the appropriate sequence of administering protein of the present invention in combination with cytokine(s), lymphokine(s), other hematopoietic factor(s), thrombolytic or anti-thrombotic factors. Administration of protein of the present invention used in the pharmaceutical composition or to practice the method of the present invention can be carried out in a variety of conventional ways, such as oral ingestion, inhalation, topical application or cutaneous, subcutaneous, intraperitoneal, parenteral or intravenous injection. Intravenous administration to the patient is preferred.

When a therapeutically effective amount of protein of the present invention is administered orally, protein of the present invention will be in the form of a tablet, capsule, powder, solution or elixir. When administered in tablet form, the pharmaceutical composition of the invention may additionally contain a solid carrier such as a gelatin or an adjuvant. The tablet, capsule, and powder contain from about 5 to 95% protein of the present invention, and preferably from about 25 to 90% protein of the present invention. When administered in liquid form, a liquid carrier such as water, petroleum, oils of animal or plant origin such as peanut oil, mineral oil, soybean oil, or sesame oil, or synthetic oils may be added. The liquid form of the pharmaceutical composition may further contain physiological saline solution, dextrose or other saccharide solution, or glycols such as ethylene glycol, propylene glycol or polyethylene glycol. When administered in liquid form, the pharmaceutical composition contains from about 0.5 to 90% by weight of protein of the present invention, and preferably from about 1 to 50% protein of the present invention.

When a therapeutically effective amount of protein of the present invention is administered by intravenous, cutaneous or subcutaneous injection, protein of the present invention will be in the form of a pyrogen-free, parenterally acceptable aqueous solution. The preparation of such parenterally acceptable protein solutions, having due regard to pH, isotonicity, stability, and the like, is within the skill in the art. A preferred pharmaceutical composition for intravenous, cutaneous, or subcutaneous injection should contain, in addition to protein of the present invention, an isotonic vehicle such as Sodium Chloride Injection, Ringer's Injection, Dextrose Injection, Dextrose and Sodium Chloride Injection, Lactated Ringer's Injection, or other vehicle as known in the art. The pharmaceutical composition of the present invention may also contain stabilizers, preservatives, buffers, antioxidants, or other additives known to those of skill in the art.

The amount of protein of the present invention in the pharmaceutical composition of the present invention will depend upon the nature and severity of the condition being treated, and on the nature of prior treatments which the patient has undergone. Ultimately, the attending physician will decide the amount of protein of the present invention with which to treat each individual patient. Initially, the attending physician will administer low doses of protein of the present invention and observe the patient's response. Larger doses of protein of the present invention may be administered until the optimal therapeutic effect is obtained for the patient, and at that point the dosage is not increased further. It is contemplated that the various pharmaceutical compositions used to practice the method of the present invention should contain about 0.01 .mu.g to about 100 mg (preferably about 0.1 ng to about 10 mg, more preferably about 0.1 .mu.g to about 1 mg) of protein of the present invention per kg body weight. The duration of intravenous therapy using the pharmaceutical composition of the present invention will vary, depending on the severity of the disease being treated and the condition and potential idiosyncratic response of each individual patient. It is contemplated that the duration of each application of the protein of the present invention will be in the range of 12 to 24 hours of continuous intravenous administration. Ultimately the attending physician will decide on the appropriate duration of intravenous therapy using the pharmaceutical composition of the present invention.

Protein of the invention may also be used to immunize animals to obtain polyclonal and monoclonal antibodies which specifically react with the protein. Such antibodies may be obtained using either the entire protein or fragments thereof as an immunogen. The peptide immunogens additionally may contain a cysteine residue at the carboxyl terminus, and are conjugated to a hapten such as keyhole limpet hemocyanin (KLH). Methods for synthesizing such peptides are known in the art, for example, as in R. P. Merrifield, J. Amer.Chem.Soc. 85, 2149–2154 (1963); J. L. Krstenansky, et al., FEBS Lett. 211, 10 (1987). Monoclonal antibodies binding to the protein of the invention may be useful diagnostic agents for the immunodetection of the protein. Neutralizing monoclonal antibodies binding to the protein may also be useful therapeutics for both conditions associated with the protein and also in the treatment of some forms of cancer where abnormal expression of the protein is involved. In the case of cancerous cells or leukemic cells, neutralizing monoclonal antibodies against the protein may be useful in detecting and preventing the metastatic spread of the cancerous cells, which may be mediated by the protein.

For compositions of the present invention which are useful for bone, cartilage, tendon or ligament regeneration, the therapeutic method includes administering the composition topically, systematically, or locally as an implant or device. When administered, the therapeutic composition for use in this invention is, of course, in a pyrogen-free, physiologically acceptable form. Further, the composition may desirably be encapsulated or injected in a viscous form for delivery to the site of bone, cartilage or tissue damage. Topical administration may be suitable for wound healing and tissue repair. Therapeutically useful agents other than a protein of the invention which may also optionally be included in the composition as described above, may alternatively or additionally, be administered simultaneously or sequentially with the composition in the methods of the invention. Preferably for bone and/or cartilage formation, the composition would include a matrix capable of delivering the protein-containing composition to the site of bone and/or cartilage damage, providing a structure for the developing bone and cartilage and optimally capable of being resorbed into the body. Such matrices may be formed of materials presently in use for other implanted medical applications. The choice of matrix material is based on biocompatibility, biodegradability, mechanical properties, cosmetic appearance and interface properties. The particular application of the compositions will define the appropriate formulation. Potential matrices for the compositions may be biodegradable and chemically defined calcium sulfate, tricalciumphosphate, hydroxyapatite, polylactic acid, polyglycolic acid and polyanhydrides. Other potential materials are biodegradable and biologically well-defined, such as bone or dermal collagen. Further matrices are comprised of pure proteins or extracellular matrix components. Other potential matrices are nonbiodegradable and chemically defined, such as sintered hydroxapatite, bioglass, aluminates, or other ceramics. Matrices may be comprised of combinations of any of the above mentioned types of material, such as polylactic acid and hydroxyapatite or collagen and tricalciumphosphate. The bioceramics may be altered in composition, such as in calcium-aluminate-phosphate and processing to alter pore size, particle size, particle shape, and biodegradability. Presently preferred is a 50:50 (mole weight) copolymer of lactic acid and glycolic acid in the form of porous particles having diameters ranging from 150 to 800 microns. In some applications, it will be useful to utilize a sequestering agent, such as carboxymethyl cellulose or autologous blood clot, to prevent the protein compositions from disassociating from the matrix. A preferred family of sequestering agents is cellulosic materials such as alkylcelluloses (including hydroxyalkylcelluloses), including methylcellulose, ethylcellulose, hydroxyethylcellulose, hydroxypropylcellulose, hydroxypropylmethylcellulose, and carboxymethylcellulose, the most preferred being cationic salts of carboxymethylcellulose (CMC). Other preferred sequestering agents include hyaluronic acid, sodium alginate, poly(ethylene glycol), polyoxyethylene oxide, carboxyvinyl polymer and poly(vinyl alcohol). The amount of sequestering agent useful herein is 0.5–20 wt %, preferably 1–10 wt % based on total formulation weight, which represents the amount necessary to prevent desorbtion of the protein from the polymer matrix and to provide appropriate handling of the composition, yet not so much that the progenitor cells are prevented from infiltrating the matrix, thereby providing the protein the opportunity to assist the osteogenic activity of the progenitor cells. In further compositions, proteins of the invention may be combined with other agents beneficial to the treatment of the bone and/or cartilage defect, wound, or tissue in question. These agents include various growth factors such as epidermal growth factor (EGF), platelet derived growth factor (PDGF), transforming growth factors (TGF-.alpha. and TGF-.beta.), and insulin-like growth factor (IGF). The therapeutic compositions are also presently valuable for veterinary applications. Particularly domestic animals and thoroughbred horses, in addition to humans, are desired patients for such treatment with proteins of the present invention. The dosage regimen of a protein-containing pharmaceutical composition to be used in tissue regeneration will be determined by the attending physician considering various factors which modify the action of the proteins, e.g., amount of tissue weight desired to be formed, the site of damage, the condition of the damaged tissue, the size of a wound, type of damaged tissue (e.g., bone), the patient's age, sex, and diet, the severity of any infection, time of administration and other clinical factors. The dosage may vary with the type of matrix used in the reconstitution and with inclusion of other proteins in the pharmaceutical composition. For example, the addition of other known growth factors, such as IGF I (insulin like growth factor I), to the final composition, may also effect the dosage. Progress can be monitored by periodic assessment of tissue/bone growth and/or repair, for example, X-rays, histomorphometric determinations and tetracycline labeling. Polynucleotides of the present invention can also be used for gene therapy. Such polynucleotides can be introduced either in vivo or ex vivo into cells for expression in a mammalian subject. Polynucleotides of the invention may also be administered by other known methods for introduction of nucleic acid into a cell or organism (including, without limitation, in the form of viral vectors or naked DNA). Cells may also be cultured ex vivo in the presence of proteins of the present invention in order to proliferate or to produce a desired effect on or activity in such cells. Treated cells can then be introduced in vivo for therapeutic purposes.

The following examples are provided to further illustrate particular embodiments of the invention, and are not to be construed as limiting the scope of the present invention.

EXAMPLE 1

Isolation of Polynucleotides Encoding Novel Kinases

High through put sequencing of murine dendritic cell, murine lymph node stromal cell, and human dendritic cell libraries generated nucleotide sequences which were used to query public and private sequence databases using an alogithim designed to recognize kinase subdomains. Putative kinase clones identified in this manner were further sequenced. The resultant complete clone sequences are shown as: SEQ ID NO:1–6, and Table VIII identifies the specific library and clones for each of these sequences. In the case of SS4694 (SEQ ID NO:6), sequence information derived from SS4694 and KIAA0551 (see pp. ////26–27) enabled the cloning of LNRK-1 (SEQ ID NO:7) from a Marathon-ready human spleen cDNA library (Clontech).

TABLE VIII

| Name | SEQ ID NO | Library | Clone # |
|---|---|---|---|
| MDCK-1 | 1 | Murine dendritic cell | 990219MDCA001250HT |
| MDCK-2 | 2 | Murine dendritic cell | 990205MDCA999084HT |
| MDCK-3 | 3 | Murine dendritic cell | 990217MDCA001428HT |
| MLSK-1 | 4 | Murine lymph node stromal cell | 980906MLSA002022HT |
| MLSK-2 | 5 | Murine lymph node stromal cell | 9980905MLSA001070HT |
| LNRK-1 | 6 | Human dendritic cell | ss4694 |

EXAMPLE 2

Use of Kinase Polypeptides in an ELISA

Kinase-specific ELISA:

Serial dilutions of kinase-containing samples (in 50 mM $NaHCO_3$, brought to pH 9 with NaOH) are coated onto Linbro/Titertek 96 well flat bottom E.I.A. microtitration plates (ICN Biomedicals Inc., Aurora, Ohio) at 100:1/well. After incubation at 4° C. for 16 hours, the wells are washed six times with 200:1 PBS containing 0.05% Tween-20 (PBS-Tween). The wells are then incubated with FLAG®-binding partner at 1 mg/ml in PBS-Tween with 5% fetal calf serum (FCS) for 90 minutes (100:1 per well), followed by washing as above. Next, each well is incubated with the anti-FLAG® (monoclonal antibody M2 at 1 mg/ml in PBS-Tween containing 5% FCS for 90 minutes (100:1 per well), followed by washing as above. Subsequently, wells are incubated with a polyclonal goat anti-mIgGI-specific horseradish peroxidase-conjugated antibody (a 1:5000 dilution of the commercial stock in PBS-Tween containing 5% FCS) for 90 minutes (100:1 per well). The HRP-conjugated antibody is obtained from Southern Biotechnology Associates, Inc., Birmingham, Ala. Wells then are washed six times, as above.

For development of the ELISA, a substrate mix [100:1 per well of a 1:1 premix of the TMB Peroxidase Substrate and Peroxidase Solution B (Kirkegaard Perry Laboratories, Gaithersburg, Md.)] is added to the wells. After sufficient color reaction, the enzymatic reaction is terminated by addition of 2 N $H_2SO_4$ (50:1 per well). Color intensity (indicating kinase/binding partner binding activity) is determined by measuring extinction at 450 nm on a V Max plate reader (Molecular Devices, Sunnyvale, Calif.).

EXAMPLE 3

Monoclonal Antibodies That Bind

This example illustrates a method for preparing monoclonal antibodies that bind kinases of the invention. Suitable immunogens that may be employed in generating such antibodies include, but are not limited to, purified kinase polypeptides or an immunogenic fragment thereof, or fusion proteins containing a kinase of the invention (e.g., a soluble kinase/Fc fusion protein).

Purified kinases can be used to generate monoclonal antibodies immunoreactive therewith, using conventional techniques such as those described in U.S. Pat. No. 4,411,993. Briefly, mice are immunized with kinase immunogen emulsified in complete Freund's adjuvant, and injected in amounts ranging from 10–100 µg subcutaneously or intraperitoneally. Ten to twelve days later, the immunized animals are boosted with additional kinase immunogen emulsified in incomplete Freund's adjuvant. Mice are periodically boosted thereafter on a weekly to bi-weekly immunization schedule. Serum samples are periodically taken by retro-orbital bleeding or tail-tip excision to test for anti-kinase antibodies by dot blot assay, ELISA (Enzyme-Linked Immunosorbent Assay) or inhibition of kinase/binding partner binding.

Following detection of an appropriate antibody titer, positive animals are provided one last intravenous injection of kinase immunogen in saline. Three to four days later, the animals are sacrificed, spleen cells harvested, and spleen cells are fused to a murine myeloma cell line, e.g., NS1 or preferably P3x63Ag8.653 (ATCC CRL 1580). Fusions generate hybridoma cells, which are plated in multiple microtiter plates in a HAT (hypoxanthine, aminopterin and thymidine) selective medium to inhibit proliferation of non-fused cells, myeloma hybrids, and spleen cell hybrids.

The hybridoma cells are screened by ELISA for reactivity against purified kinase polypeptides by adaptations of the techniques disclosed in Engvall et al., *Immunochem.* 8:871, 1971 and in U.S. Pat. No. 4,703,004. A preferred screening technique is the antibody capture technique described in Beckmann et al., (*J. Immunol.* 144:4212, 1990) Positive hybridoma cells can be injected intraperitoneally into syngeneic BALB/c mice to produce ascites containing high concentrations of anti-kinase monoclonal antibodies. Alternatively, hybridoma cells can be grown in vitro in flasks or roller bottles by various techniques. Monoclonal antibodies produced in mouse ascites can be purified by ammonium sulfate precipitation, followed by gel exclusion chromatography. Alternatively, affinity chromatography based upon binding of antibody to Protein A or Protein G can also be used, as can affinity chromatography based upon binding to kinase polypeptides of the invention.

EXAMPLE 4

PCR Analysis of Tissue-Specific Kinase Expresion

The tissue distribution of MDCK-2, MDCK-3, MLSK-1, MLSK-2 and ss4694 mRNA was investigated. Using Clonetech multiple tissue cDNA panels and clone specific oligonucleotide PCR primers, we determined that expression of MDCK-2 was ubiquitous throughout the Clonetech murine cDNA panel, with highest levels in spleen, liver, skeletal muscle and seven day embryo. MDCK-3 expression was highest in heart, brain and spleen; lower level expression was seen in liver, skeletal muscle and testis, and low but detectable levels in lung and kidney. Expression of MLSK-1 was found to be highest in the heart, lung, and liver.

Lower levels of MLSK-1 were detected in the kidney and skeletal muscle, and MLSK-1 expression was absent from brain and spleen. Expression of MLSK-2 was highest in the heart and spleen while lower levels of expression were found in the lung and liver, and no expression was detectable in the brain, skeletal muscle, kidney and testis.

SS4694 and therefore LNRK-1 expression is ubiquitous throughout the human cDNA panels (Clontech human tissue panel 1, human tissue panel 2 and human immune tissue panel) with highest levels in peripheral blood lymphocyte cDNA. All other tissues had roughly equivalent levels of expression.

EXAMPLE 5

Measuring Kinase Activity

Isolated kinase polypeptides or fusion proteins containing the isolated protein kinase domain can be used in an assay of protein kinase activity.

Typically this would be carried out by combining a kinase of the invention with radiolabeled ATP ($\gamma^{32}$P-ATP) and a magnesium (or other divalent cation, such as manganese) salt in buffer solution containing a peptide or protein substrate. Peptide substrates are generally from 8–30 amino acids in length and may terminate at the N- or C-terminus with three or more lysine or arginine residues to facilitate binding of the peptide to phosphocellulose paper. The substrate may also be a protein known to be phosphorylated readily by a kinase of the invention. Many such general kinase substrates are known, such as, α or β casein, histone H1, myelin basic protein, etc. After incubation of this reaction mixture at 20–37° C. for a suitable time, the transfer of radioactive phosphate from ATP to the substrate protein or substrate peptide may be monitored, by acidifying the reaction mixture then spotting it onto phosphocellulose paper, and subsequent washing of the paper with a dilute solution of phosphoric acid, in the case of a peptide substrate, or by application of the reaction products to a gel electrophoresis system followed by autoradiographic detection in the case of proteins.

A specific example of this type of assay of kinase activiy is the PhosphoSpots™ assay (Jerini Bio Tools GMBH), in which protein or peptide substrates are attached to a solid support. In one example, the substrates may be peptides where each is known to be phosphorylated by a particular kinase. When the kinase being tested is added to the substrates in the presence of γ-$^{32}$P, any attached proteins or peptides that are suitable subtrates for that kinase will be labeled with the γ-$^{32}$P which can be quantitatively detected using a phosphoimager. (See, for example, Tegge et al., 1995, Determination of cyclic nucleotide-dependent protein kinase substrate specificity by the use of peptide libraries on cellulose paper, *Biochemistry* 34 (33): 10569–10577, which is incorporated by reference herein). The results of such an assay for MLSK-1 substrate specificity are shown in Table IX below.

TABLE IX

Phosphorylation of known kinase substrates by MLSK-1

| Protein Kinase ("PK") | Known PK Substrate Sequence | SEQ ID NO: | Phosphorylation by MLSK-1 (% of max.) |
|---|---|---|---|
| cAMP-dependent protein kinase | LRRASLG | 17 | 65.9 |
| cGMP-dependent protein kinase | RKISASEFDRPLR | 18 | 62.2 |
| protein kinase C | KKRFSFKKSFKLSGFSFK | 19 | 100.0 |
| protein kinase C | QKRPSQRSK | 20 | 75.0 |
| Ca-/calmodulin-dependent PK | KKALRRQETVDAL | 21 | 20.9 |
| Ca-/calmodulin-dependent PK | PLARTLSVAGLPGK | 22 | 10.3 |
| casein kinase II | RRRDDDSDDD | 23 | 17.6 |
| cdc2-kinase | Ac-SPGRRRRK | 24 | 94.8 |
| p34 cdc-kinase | PKTPKKAKKL | 25 | 82.0 |
| p42/p44 MAP kinase | APRTPGGRR | 26 | 88.6 |
| p42/p44 MAP kinase | EAAEAEPAEPSSPAAEAEGA | 27 | 0.0 |
| p42/p44 MAP kinase | LMECRNSPVAKT | 28 | 3.8 |
| casein kinase I | RRKDLHDDEEDEAMSITA | 29 | 14.1 |
| S6 kinase | LSSLRASTSKSGGQK | 30 | 66.6 |
| myosin light chain kinase | KKRPQRATSNVFS | 31 | 72.0 |
| insulin receptor tyrosine kinase | KKKLPATGDYMNMSPVGD | 32 | 33.7 |
| csk tyrosine kinase | KKKKEEIYFFF | 33 | 82.1 |
| raf-1 kinase | SGQLIDSMANSFVGTRS | 34 | 43.1 |
| abl tyrosine kinase | EAIYAAPFAKKK | 35 | 69.3 |
| c-src tyrosine kinase | YIYGSFK | 36 | 66.6 |

Kinase activity may also be measured, in vitro or in intact cells, using a fluorescence resonance energy transfer (FRET) assay, in which the transfer of energy between fluorescently tagged kinase and substrate molecules is detected. (For example, see Ng et al., 1999, Imaging protein kinase C alpha activation in cells, *Science* 283 (5410): 2085–2089, which is incorporated by reference herein.)

Other methods are available to conveniently measure the kinase-mediated transfer of phosphate to substrate proteins or peptides, such as the scintillation proximity assay, and the use of monoclonal antibodies that are specific for phosphorylated or non-phosphorylated forms of substrate molecules; these methods are well known to those practiced in the art.

EXAMPLE 6

Tissue- and Stge-Specific Expression of Kinase mRNAs

The expression of MDCK-2, MDCK-3, MLSK-1, MLSK-2, and ss4694 (LNRK-1) was assessed by PCR using gene-specific oligonucleotide primers directed toward these kinase-encoding polynucleotides usign Clontech multiple tissue cDNA panels as templates. Expression of MDCK-2, MDCK-3, MLSK-1, and MLSK-2 was assayed using the murine cDNA panel (see Table X below). Expression of MDCK-2 was observed in all tissues on this panel, with the highest levels in spleen, liver, skeletal muscle, and seven-day embryo. Expression of MDCK-3 was highest in heart, brain and spleen; lower-level expression was seen in liver, skeletal muscle and testis, and low but detectable levels were observed in lung and kidney; however, expression of MDCK-3 was completely absent from murine embryo. Expression of MLSK-1 was highest in the heart, lung, and liver, and is absent from the brain and spleen; MLSK-1 expression in the embryo is only seen at the 11-day stage. Expression of MLSK-2 is found to be highest in the heart and spleen. MLSK-2 is expressed at lower levels in lung, liver, and 7-day embryo, and is not detectable in brain, skeletal muscle, kidney, testis, or embryonic tissue at other stages of development. ss4694(LNRK-1) expression is ubiquitous throughout the human cDNA panels, with highest levels in PBL (peripheral blood lymphocyte) cDNA. All other tissues had roughly equivalent levels of expression.

TABLE X

| MURINE PANEL | MDCK-2 | MDCK-3 | MLSK-1 | MLSK-2 |
|---|---|---|---|---|
| Heart | ** | *** | *** | *** |
| Brain | ** | *** | | |
| Spleen | *** | *** | | ** |
| Lung | ** | * | *** | * |
| Liver | *** | ** | *** | * |
| Skeletal Muscle | *** | ** | * | |
| Kidney | ** | * | ** | |
| Testis | ** | ** | | |
| 7-day Embryo | *** | | | * |
| 11-day Embryo | ** | | ** | |
| 15-day Embryo | * | | | |
| 17-day Embryo | ** | | | |

Expression of the ss4694 clone (and therefore of LNRK-1) was assayed using the Clontech "human tissue" and "human immune" cDNA panels (see Table XI below). ss4694 (LNRK-1) expression is observed throughout the human cDNA panels, with highest levels in PBL (peripheral blood lymphocyte) cDNA. All other tissues had roughly equivalent levels of expression.

TABLE XI

| | ss4694/LNRK-1 Expression |
|---|---|
| HUMAN TISSUE PANEL I | |
| Brain | ** |
| Heart | ** |
| Kidney | * |
| Liver | ** |
| Lung | ** |
| Pancreas | ** |
| Placenta | ** |
| Skeletal Muscle | * |
| HUMAN TISSUE PANEL II | |
| Colon | ** |
| Ovary | ** |
| PBL | *** |
| Prostate | ** |
| Small Intestine | * |
| Spleen | ** |
| Testis | ** |
| Thymus | ** |
| HUMAN IMMUNE PANEL | |
| Bone Marrow | ** |
| Fetal Liver | ** |
| Lymph Node | ** |
| PBL | *** |
| Spleen | ** |
| Thymus | ** |
| Tonsil | ** |

EXAMPLE 7

Regulation of MDCK-3 Expression in Dendritic Cell Maturation

The regulation of MDCK-3 RNA expression during dendritic cell "maturation" and/or "activation" was assayed by RT (reverse transcriptase) PCR (polymerase chain reaction). Flt3 ligand ("Flt3L") is a growth factor that stimulates the proliferation of hematopoietic cells. RNA samples isolated from splenic dendritic cells purified from Flt3L-treated mice were assayed by RT PCR using primers derived from the MDCK-3 cDNA sequence. MDCK-3 RNA was undetected in the freshly isolated dendritic cells, but was present in cells following overnight culture in a defined medium, a growth procedure which causes dendritic cell "maturation". This indicates that regulation of MDCK-3 expression is correlated with the maturation state of at least one type of cell involved in immune responses.

Furthermore, RT PCR was performed on RNA isolated from a different dendritic cell system, where murine bone marrow cells are isolated and then cultured in media containing Flt3 ligand for nine days, with the addition of various dendritic cell "activators" during the final 24 hours of the incubation period. MDCK-3 mRNA levels were specifically altered by some "activators" but not others.

These assays can also be performed with a variety of cells such as peripheral blood mononuclear cells and a variety of activating substances such as IL-4, GM-CSF, TNF, IL-2, IFN, LPS, etc. to test for a correlation between changes in cell differentiation or proloferative activity and the expression of the kinases of the invention.

EXAMPLE 8

Assaying Activation of Kinase Pathways by Detecting Phosphorylation of Known Pathway Components Cell signalling pathways often involve a cascade of phosphorylation events. Over-expression of kinases in cells can activate such signalling pathways, and this activation may be detected by measuring the level of phosphorylation of molecules that are known to be 'downstream' phosphorylated recipients of 'upstream' kinase activity. Conversely, over-expression of a catalytically inactive, truncated, or otherwise mutated form of a kinase can act as a dominant negative mutation and disrupt or abolish normal signalling events 'downstream' of the kinase.

In one example, we expressed active forms of MLSK-1 and of MLSK-2 and showed that when over-expressed in COS cells each of these kinases activates the MAP kinase signaling pathway as evidenced by the generation of phosphorylated forms of ERK, a 'downstream' kinase in the MAP kinase pathway. Phosphorylation of signalling pathway molecules can be detected in a variety of ways, including incorporation of $^{32}P$ followed by immunoprecipitation, FRET assays as described in Example 5, or the use of phosphorylation-state-specific antibodies in ELISA assays or on Western blots. Additionally, kinase specificity for a particular cell signalling pathway can be assessed by comparing the phosphorylation responses of 'downstream' molecules in different pathways to over-expression of that kinase. For example, over-expression of MLSK-1 and of MLSK-2 in COS cells had no effect on the stress-activated kinase pathway, as expression of these kinases did not result in activation of either JNK or p38 kinases.

EXAMPLE 9

Reporter Gene Assays of Kinase Pathway Activation

Activation of cell signalling pathways by kinases of the invention may also be assayed using reporter gene constructs. In such constructs a reporter gene such as luciferase or β-galactosidase is placed downstream of a promoter, enhancer, or other transcriptional regulatory element that is known to bind transcription factors as a result of activation of a cell signalling pathway. This transcriptional regulatory element may be selected on the basis of its known association with a relevant transcription factor, such as AP-1 or NFκB, or on the basis of physical association with a downstream gene known to be regulated by the signalling pathway. An example of the use of such reporter constructs is described in Ling et al., 1998, NF-kappaB-inducing kinase activates IKK-alpha by phosphorylation of Ser-176, *Proc Natl Acad Sci USA* 95 (7): 3792–3797, which is incorporated by reference herein.

In one example, assays to determine whether MLSK-1 or MLSK-2 could activate the transcription factor AP-1 were performed. AP-1 is a transcription factor known to be involved in the JNK and p38 signalling pathways. MLSK-1 and MLSK-2 were each individually co-tranfected with an AP-1-luciferase construct into COS-7 cells in a standard AP-1-luciferase reporter assay. The overexpression of neither MLSK-1 nor MLSK-2 activates AP-1 using this assay system, consistent with these kinases not participating in the stress-activated JNK and p38 signalling pathways.

The specification is most thoroughly understood in light of the teachings of the references cited within the specification which are hereby incorporated by reference. The embodiments within the specification provide an illustration of embodiments of the invention and should not be construed to limit the scope of the invention. The skilled artisan readily recognizes that many other embodiments are encompassed by the invention.

What is claimed is:

1. A method for identifying compounds that inhibit kinase activity comprising:
   (a) combining a test compound with an isolated polypeptide having kinase activity and a substrate of said polypeptide; and
   (b) determining whether the test compound inhibits the kinase activity of said polypeptide;
   wherein said polypeptide comprises an amino acid sequence selected from the group consisting of SEQ ID NO:10, the amino acid sequence of SEQ ID NO:10 from which one through five amino acids have been removed from the N-terminus, the amino acid sequence of SEQ ID NO:10 from which one through five amino acids have been removed from the C-terminus, amino acids 23 through 279 of SEQ ID NO:10, and the amino acid sequence of a kinase domain that is at least 95% identical to amino acids 23 through 279 of SEQ ID NO:10.

2. The method of claim 1 where the polypeptide is produced by a process comprising culturing a recombinant host cell, said recombinant host cell comprising a nucleic acid encoding said polypeptide, under conditions promoting expression of said polypeptide.

3. The method of claim 2 wherein the nucleic acid comprises a nucleotide sequence selected from the group consisting of:
   (a) SEQ ID NO:3;
   (b) nucleotides 243 through 1307 of SEQ ID NO:3; and
   (c) a nucleotide sequence encoding an amino acid sequence selected from the group consisting of SEQ ID NO:10, the amino acid sequence of SEQ ID NO:10 from which one through five amino acids have been removed from the N-terminus, the amino acid sequence of SEQ ID NO:10 from which one through five amino acids have been removed from the C-tertminus, amino acids 23 through 279 of SEQ ID NO:10, and the amino acid sequence of a kinase domain that is at least 95% identical to amino acids 23 through 279 of SEQ ID NO:10.

4. The method of claim 1 wherein the substrate is a peptide from 8 to 30 amino acids in length.

5. The method of claim 1 wherein the test compound is combined with the polypeptide and the substrate in the presence of radiolabeled ATP.

6. A method for identifying compounds that activate kinase activity comprising:
   (a) combining a test compound with an isolated polypeptide having kinase activity and a substrate of said polypeptide; and
   (b) determining whether the test compound activates the kinase activity of said polypeptide;
   wherein said polypeptide comprises an amino acid sequence selected from the group consisting of SEQ ID NO:10, the amino acid sequence of SEQ ID NO:10 from which one through five amino acids have been removed from the N-terminus, the amino acid sequence of SEQ ID NO:10 from which one through five amino acids have been removed from the C-terminus, amino acids 23 through 279 of SEQ ID NO:10, and the amino acid sequence of a kinase domain that is at least 95% identical to amino acids 23 through 279 of SEQ ID NO:10.

7. The method of claim 6 where the polypeptide is produced by a process comprising culturing a recombinant host cell, said recombinant host cell comprising a nucleic acid encoding said polypeptide, under conditions promoting expression of said polypeptide.

8. The method of claim 7 wherein the nucleic acid comprises a nucleotide sequence selected from the group consisting of:
   (a) SEQ ID NO:3;
   (b) nucleotides 243 through 1307 of SEQ ID NO:3; and
   (c) a nucleotide sequence encoding an amino acid sequence selected from the group consisting of SEQ ID NO:10, the amino acid sequence of SEQ ID NO:10 from which one through five amino acids have been removed from the N-terminus, the amino acid sequence of SEQ ID NO:10 from which one through five amino acids have been removed from the C-terminus, amino acids 23 through 279 of SEQ ID NO:10, and the amino acid sequence of a kinase domain that is at least 95% identical to amino acids 23 through 279 of SEQ ID NO:10.

9. The method of claim 6 wherein the substrate is a peptide from 8 to 30 amino acids in length.

10. The method of claim 6 wherein the test compound is combined with the polypeptide and the substrate in the presence of radiolabeled ATP.

11. A method for identifying compounds that inhibit kinase activity comprising:
   (a) combining a test compound with a polypeptide having kinase activity and a substrate of said polypeptide; and
   (b) determining whether the test compound inhibits the kinase activity of said polypeptide;
wherein said polypeptide is produced by expression of a recombinant vector comprising a nucleic acid, said nucleic acid encoding an amino acid sequence selected from the group consisting of SEQ ID NO:10, the amino acid sequence of SEQ ID NO:10 from which one through five amino acids have been removed from the N-terminus, the amino acid sequence of SEQ ID NO:10 from which one through five amino acids have been removed from the C-terminus, amino acids 23 through 279 of SEQ ID NO:10, and the amino acid sequence of a kinase domain that is at least 95% identical to amino acids 23 through 279 of SEQ ID NO:10.

12. The method of claim 11 where the test compound is combined with the polypeptide in a mammalian cell grown in culture.

13. The method of claim 11 where the test compound is combined with the polypeptide in vitro.

14. The method of claim 11 wherein the nucleic acid comprises a nucleotide sequence selected from the group consisting of:
   (a) SEQ ID NO:3;
   (b) nucleotides 243 through 1307 of SEQ ID NO:3; and
   (c) a nucleotide sequence encoding an amino acid sequence selected from the group consisting of SEQ ID NO:10 and amino acids 23 through 279 of SEQ ID NO:10.

15. The method of claim 11 wherein the substrate is a peptide from 8 to 30 amino acids in length.

16. The method of claim 11 wherein the test compound is combined with the polypeptide and the substrate in the presence of radiolabeled ATP.

17. The method of claim 16 further comprising transferring the radioactive products onto phosphocellulose paper.

18. A method for identifying compounds that inhibit kinase activity comprising:
   (a) combining a test compound with an isolated polypeptide having kinase activity and a substrate of said polypeptide; and
   (b) determining whether the test compound inhibits the kinase activity of said polypeptide;
wherein said polypeptide comprises an amino acid sequence selected from the group consisting of SEQ ID NO:10 and amino acids 23 through 279 of SEQ ID NO:10.

19. The method of claim 18 where the polypeptide is produced by a process comprising culturing a recombinant host cell, said recombinant host cell comprising a nucleic acid encoding said polypeptide, under conditions promoting expression of said polypeptide.

20. The method of claim 19 wherein the nucleic acid comprises a nucleotide sequence selected from the group consisting of:
   (a) SEQ ID NO:3;
   (b) nucleotides 243 through 1307 of SEQ ID NO:3; and
   (c) a nucleotide sequence encoding an amino acid sequence selected from the group consisting of SEQ ID NO:10 and amino acids 23 through 279 of SEQ ID NO:10.

21. The method of claim 12 wherein the mammalian cell is selected from the group consisting of dendritic cells, COS-7 cells, CHO cells, and CV1/EBNA cells.

22. The method of claim 11 where the test compound is combined with the polypeptide in a cell selected from the group consisting of prokaryotic cells, fungal cells, and yeast cells.

* * * * *